US008987319B2

(12) United States Patent
Miller

(10) Patent No.: US 8,987,319 B2
(45) Date of Patent: Mar. 24, 2015

(54) SELECTIVE ANDROGEN RECEPTOR MODULATORS

(75) Inventor: Chris P. Miller, Lake Forest, IL (US)

(73) Assignee: Radius Health, Inc., Waltham, MA (US)

( * ) Notice: Subject to any disclaimer, the term of this patent is extended or adjusted under 35 U.S.C. 154(b) by 0 days.

(21) Appl. No.: 13/576,754

(22) PCT Filed: Feb. 4, 2011

(86) PCT No.: PCT/US2011/023768
§ 371 (c)(1),
(2), (4) Date: Oct. 22, 2012

(87) PCT Pub. No.: WO2011/097496
PCT Pub. Date: Aug. 11, 2011

(65) Prior Publication Data
US 2013/0041007 A1    Feb. 14, 2013

Related U.S. Application Data

(60) Provisional application No. 61/301,492, filed on Feb. 4, 2010.

(51) Int. Cl.
A61K 31/40    (2006.01)
C07D 209/88    (2006.01)

(52) U.S. Cl.
CPC .................................. *C07D 209/88* (2013.01)
USPC ........................................................ 514/411

(58) Field of Classification Search
None
See application file for complete search history.

(56) References Cited

U.S. PATENT DOCUMENTS

| | | | |
|---|---|---|---|
| 5,411,981 A | 5/1995 | Gaillard-Kelly et al. |
| 6,156,899 A | 12/2000 | Galey et al. |
| 6,159,959 A | 12/2000 | Miller |
| 6,960,474 B2 | 11/2005 | Salvati et al. |
| 7,446,110 B2 | 11/2008 | Kaufman et al. |
| 8,067,448 B2 | 11/2011 | Miller |
| 8,268,872 B2 | 9/2012 | Miller |
| 8,455,525 B2 | 6/2013 | Miller |
| 8,629,167 B2 | 1/2014 | Miller |
| 8,642,632 B2 | 2/2014 | Miller |
| 2005/0182105 A1 | 8/2005 | Nirschl et al. |
| 2005/0250749 A1 | 11/2005 | Labrie et al. |
| 2005/0261303 A1 | 11/2005 | Taniguchi et al. |
| 2006/0106067 A1 | 5/2006 | Shiraishi et al. |
| 2006/0116415 A1 | 6/2006 | Sui et al. |
| 2006/0142387 A1 | 6/2006 | Cadilla et al. |
| 2006/0148893 A1 | 7/2006 | Blanc et al. |
| 2006/0211756 A1 | 9/2006 | Zhang et al. |
| 2006/0287327 A1 | 12/2006 | Labrie et al. |
| 2007/0088039 A1 | 4/2007 | Balog et al. |
| 2007/0254875 A1 | 11/2007 | Zhi et al. |
| 2007/0281906 A1 | 12/2007 | Dalton et al. |
| 2008/0057068 A1 | 3/2008 | Dalton et al. |
| 2009/0042866 A1 | 2/2009 | Lennox et al. |
| 2009/0042967 A1 | 2/2009 | Hasuoka |
| 2009/0253758 A1 | 10/2009 | Miller |
| 2009/0264534 A1 | 10/2009 | Dalton et al. |
| 2010/0041721 A1 | 2/2010 | Miller |
| 2010/0152236 A1 | 6/2010 | Yamamoto et al. |
| 2011/0224267 A1 | 9/2011 | Miller |
| 2012/0004270 A1 | 1/2012 | Miller |
| 2013/0116288 A1 | 5/2013 | Miller |
| 2013/0217732 A1 | 8/2013 | Miller |

FOREIGN PATENT DOCUMENTS

| | | |
|---|---|---|
| EP | 0 916 652 | 5/1999 |
| EP | 0 580 459 B1 | 3/2001 |
| EP | 1 911 743 A1 | 4/2008 |
| GB | 1 547 758 A | 6/1979 |
| JP | 60-16957 A | 1/1985 |
| JP | 01-261381 A | 10/1989 |
| WO | WO 94/27989 A1 | 12/1994 |
| WO | WO 96/41793 A1 | 12/1996 |
| WO | WO 97/49709 A1 | 12/1997 |
| WO | WO 02/16310 A1 | 2/2002 |
| WO | WO 03/011824 A1 | 2/2003 |
| WO | WO 03/068217 A1 | 8/2003 |
| WO | WO 03/096980 A2 | 11/2003 |
| WO | WO 2004/041277 A1 | 5/2004 |
| WO | WO 2004/041782 A1 | 5/2004 |
| WO | WO 2004/045518 A2 | 6/2004 |
| WO | WO 2004/080377 A2 | 9/2004 |

(Continued)

OTHER PUBLICATIONS

Anderson (Chem and Biol 10:787-797, 2003).*
Thiel (Nature Biotechnol 2:513-519, 2004).*
Miller et al (Bioorg Med Chem Lett 20:7516-7520, 2010).*
Acevedo, S., et al., "Selective Androgen Receptor Modulators Antagonize Apolipoprotein E4-Induced Cognitive Impairments," Letters in Drug Design & Discovery, 5: 271-276 (2008).
Allan G. F., et al., "A Selective Androgen Receptor Modulator with Minimal Prostate Hypertrophic Activity Enhances Lean Body Mass in Male Rats and Stimulates Sexual Behavior in Female Rats," Endocr., 32: 41-51 (2007).
Allan, G., et al., "A Selective Androgen Receptor Modulator that Reduces Prostate Tumor Size and Prevents Orchidectomy-Induced Bone Loss in Rats," Journal of Steroid Biochemistry & Molecular Biology, 103: 76-83 (2007).

(Continued)

*Primary Examiner* — Craig Ricci
(74) *Attorney, Agent, or Firm* — Perkins Coie LLP; Yingli Wang

(57) ABSTRACT

This invention provides compounds of Formula (I), (Ia), (Ib), (Ic), (II), (IIa) or (III) and or salts thereof, pharmaceutical compositions comprising a compound of Formula (I), (Ia), (Ib), (Ic), (II), (IIa) or (III) and a pharmaceutically acceptable excipient, methods of modulating the androgen receptor, methods of treating diseases beneficially treated by an androgen receptor modulator (e.g., sarcopenia, prostate cancer, contraception, type II diabetes related disorders or diseases, anemia, depression, and renal disease) and processes for making compounds of Formula (I), (Ia), (Ib), (Ic), (II), (IIa) or (III) and intermediates useful in the preparation of same.

17 Claims, No Drawings

(56) References Cited

FOREIGN PATENT DOCUMENTS

| | | |
|---|---|---|
| WO | WO 2004/110978 A2 | 12/2004 |
| WO | WO 2005/000309 A2 | 1/2005 |
| WO | WO 2005/000794 A1 | 1/2005 |
| WO | WO 2005/000795 A2 | 1/2005 |
| WO | WO 2005/040136 A1 | 5/2005 |
| WO | WO 2005/042464 A1 | 5/2005 |
| WO | WO 2005/049574 A1 | 6/2005 |
| WO | WO 2005/049580 A1 | 6/2005 |
| WO | WO 2005/060956 A1 | 7/2005 |
| WO | WO 2005/077925 A1 | 8/2005 |
| WO | WO 2005/085185 A1 | 9/2005 |
| WO | WO 2005/086735 A2 | 9/2005 |
| WO | WO 2005/087232 A1 | 9/2005 |
| WO | WO 2005/089118 A2 | 9/2005 |
| WO | WO 2005/090282 A1 | 9/2005 |
| WO | WO 2005/090328 A1 | 9/2005 |
| WO | WO 2005/094810 A2 | 10/2005 |
| WO | WO 2005/099707 A1 | 10/2005 |
| WO | WO 2005/102998 A1 | 11/2005 |
| WO | WO 2005/108351 A1 | 11/2005 |
| WO | WO 2005/111028 A1 | 11/2005 |
| WO | WO 2005/115361 A2 | 12/2005 |
| WO | WO 2005/116001 A1 | 12/2005 |
| WO | WO 2005/120483 A2 | 12/2005 |
| WO | WO 2006/031715 A1 | 3/2006 |
| WO | WO 2006/039243 A1 | 4/2006 |
| WO | WO 2006/044359 A2 | 4/2006 |
| WO | WO 2006/044707 A1 | 4/2006 |
| WO | WO 2006/055184 A2 | 5/2006 |
| WO | WO 2006/060108 A1 | 6/2006 |
| WO | WO 2006/076317 A2 | 7/2006 |
| WO | WO 2006/113552 A2 | 10/2006 |
| WO | WO 2006/124447 A2 | 11/2006 |
| WO | WO 2006/133216 A2 | 12/2006 |
| WO | WO 2007/002181 A2 | 1/2007 |
| WO | WO 2007/005887 A2 | 1/2007 |
| WO | WO 2007/015567 A1 | 2/2007 |
| WO | WO 2007/034846 A1 | 3/2007 |
| WO | WO 2007/067490 A1 | 6/2007 |
| WO | WO 2007/087518 A2 | 8/2007 |
| WO | WO 2007/099200 A1 | 9/2007 |
| WO | WO 2007/146914 A1 | 12/2007 |
| WO | WO 2008/008433 A2 | 1/2008 |
| WO | WO 2008/011072 A2 | 1/2008 |
| WO | WO 2008/011073 A1 | 1/2008 |
| WO | WO 2008/024456 A2 | 2/2008 |
| WO | WO 2008/042571 A2 | 4/2008 |
| WO | WO 2008/044033 A1 | 4/2008 |
| WO | WO 2008/063867 A2 | 5/2008 |
| WO | WO 2008/121602 A1 | 10/2008 |
| WO | WO 2008/124000 A2 | 10/2008 |
| WO | WO 2008/124922 A1 | 10/2008 |
| WO | WO 2008/127717 A1 | 10/2008 |
| WO | WO 2008/128100 A1 | 10/2008 |
| WO | WO 2009/020234 A2 | 2/2009 |
| WO | WO 2009/065600 A2 | 5/2009 |
| WO | WO 2009/081197 A1 | 7/2009 |
| WO | WO 2009/082437 A2 | 7/2009 |
| WO | WO 2009/105214 A2 | 8/2009 |
| WO | WO 2009/133861 A1 | 11/2009 |
| WO | WO 2009/140448 A1 | 11/2009 |
| WO | WO 2010/118287 | 10/2010 |
| WO | WO 2011/097496 | 8/2011 |
| WO | WO 2012/047617 | 4/2012 |

OTHER PUBLICATIONS

Autoimmune disorders: MedlinePlus Medical Encyclopedia [online], [retrieved on Jun. 3, 2011]. Retrieved from the Internet URL: http://www.nlm.nih.gov/medlineplus/ency/article/000816.htm.

Bohl, C. E., "Structural Basis for Antagonism and Resistance of Bicalutamide in Prostate Cancer," PNAS, 102 (17): 6201-6206 (2005).

Bohl, C.E., et al., "Structural Basis for Accommodation of Nonsteroidal Ligands in the Androgen Receptors," The Journal of Biological Chemistry, 280 (45): 37747-37754 (Nov. 11, 2005).

Browne, "Chapter 2. Isotope Effect: Implications for Pharmaceutical Investigations; Stable Isotopes in Pharmaceutical Research," Elsevier; Amsterdam, 1997.

Cantin, L., et al., "Structural Characterization of the Human Androgen Receptor Ligand-Binding Domain Complexed with EM5744, a Rationally Designed Steroidal Ligand Bearing a Bulky Chain Directed Toward Helix 12," Journal of Biological Chemistry, 282 (42): 30910-30919 (Oct. 19, 2007).

"deuterium," Encyclopedia Britannica. 2009. Encyclopedia Britannica Online Feb. 18, 2009, <http://www.britannica.com/Ebchecked/topic/159684/deuterium>.

Gao, W., et al., "Comparison of the Pharmacological Effects of a Novel Selective Androgen Receptor Modulator, the 5α-Reductase Inhibitor Finasteride, and the Antiandrogen Hydroxyflutamide in Intact Rats: New Approach for Benign Prostate Hyperplasia,"Endocrinology, 145 (12): 5420-5428 (Dec. 2004).

Gao, W., et al., "Expanding the Therapeutic use of Androgens via Selective Androgen Receptor Modulators (SARMs)," Drug Discovery Today, 12: 241-248 (Mar. 2007).

Gao, W., et al., "Ockham's Razor and Selective Androgen Receptor Modulators (SARMs): Are we Overlooking the Role of 5α-Reductase?", Molecular Interventions, 7: 10-13 (Feb. 2007).

Gao, W., et al., "Selective Androgen Receptor Modulator (SARM) Treatment Improves Muscle Strength," Endocrinology, doi:10.1210/en.2005-0572, pp. 1-37 (Aug. 11, 2005).

Gao, W., et al., "Selective Androgen Receptor Modulator Treatment Improves Muscle Strength and Body Composition and Prevents Bone Loss in Orchidectomized Rats," Endocrinology, 146 (11): 4887-4897 (Nov. 2005).

Hamann, L. G., "Discovery and Preclinical Profile of a Highly Potent and Muscle Selective Androgen Receptor Modulator (SARM)," 227th National Meeting of the American Chemical Society Medicinal Chemistry Division, Mar. 28, 2004, Anaheim, CA.

Hamann, L.G., et al., "Tandem Optimization of Target Activity and Elimination of Mutagenic Potential in a Potent Series of N-aryl Bicyclic Hydantoin-Based Selective Androgen Receptor Modulators," Bioorganic & Medicinal Chemistry Letters, 17: 1860-1864 (2007).

Hanada, K., et al. "Bone Anabolic Effects of S-40503, a Novel Nonsteroidal Selective Androgen Receptor Modulator (SARM), in Rat Models of Osteoporosis," Biol. Pharm. Bull., 26(11): 1563-1569 (Nov. 2003).

Higuchi, R. I., et al., "Novel Series of Potent, Nonsteroidal, Selective Androgen Receptor Modulators Based on 7 H-[1,4]Oxazino[3,2-g]quinolin-7-ones," J. Med. Chem., 50(10): 2486-2496 (2007).

Horig, H. and Pullman, W., "From Bench to Clinic and Back: Perspective on the 1st IQPC Translational Research Conference," *Journal of Translational Medicine* 2(44):1-8 (2004).

Hwang, D. J., et al., "Arylisothiocyanato Selective Androgen Receptor Modulators (SARMs) for Prostate Cancer," Bioorganic & Medicinal Chemistry, 14: 6525-6538 (2006).

Kemppainen, J. A., et al., "Distinguishing Androgen Receptor Agonists and Antagonists: Distinct Mechanisms of Activation by Medroxyprogesterone Acetate and Dihydrotestosterone," Molecular Endocrinology, 13: 440-454 (1999).

Kilbourne, E. J., et al., "Selective Androgen Receptor Modulators for Frailty and Osteoporosis," Current Opinion in Investigational Drugs, 8(10): 821-829 (2007).

Kim, J., et al., "The 4-Para Substituent of S-3-(phenoxy)-2-hydroxy-2-methyl-N-(4-nitro-3-trifluoromethyl-phenyl)-propionamides is a Major Structural Determinant of In Vivo Disposition and Activity of Selective Androgen Receptor Modulators," JPET #88344, DOI:10.1124/jpet.105.088344, 42 pages (Jun. 29, 2005).

Kinoyama, I., et al., "(+)-(2R,5S)-4-[4-Cyano-3-(trifluoromethyl)phenyl]-2,5-dimethyl-N-[6-(trifluoromethyl)pyridin-3-yl]piperazine-1-carboxamide (YM580) as an Orally Potent and Peripherally Selective Nonsteroidal Androgen Receptor Antagonist," J. Med. Chem. 49(2): 716-726 (2006).

Lanter, J. C., et al., "The Discovery of a Potent Orally Efficacious Indole Androgen Receptor Antagonist Through in vivo Screening," Bioorganic & Medicinal Chemistry Letters, 17: 123-126 (2007).

(56) References Cited

OTHER PUBLICATIONS

Martinborough, E., et al., "Substituted 6-(1-(Pyrrolidine)quinolin-2(1H)-ones as Novel Selective Androgen Receptor Modulators," J. Med. Chem. 50(21): 5049-5052 (Oct. 18, 2007).
McGinley, P. L., et al., "Circumventing Anti-Androgen Resistance by Molecular Design," J. Am. Chem. Soc., 129: 3822-3823 (2007).
Miller, C. P., et al., "Design, Synthesis, and Preclinical Characterization of the Selective Androgen Receptor Modulator (SARM) RAD140," ACS Med. Chem. Lett., 2(2): 124-129, DOI: 10.1021/m11002508 (Dec. 2, 2010).
Mitchell, H. J., et al., Design, Synthesis, and Biological Evaluation of 16-Substituted 4-Azasteroids as Tissue-Selective Androgen Receptor Modulators (SARMs), J. Med. Chem., 52(15): 4578-81 (2009).
Mohler, M. L., et al., "Nonsteroidal Selective Androgen Receptor Modulators (SARMs): Dissociating the Anabolic and Androgenic Activities of the Androgen Receptor for Therapeutic Benefit," J. Med. Chem., 52(12): 3597-617 (Jun. 25, 2009).
Morris, J. J., et al., "Non-steroidal Antiandrogens. Design of Novel Compounds Based on an Infrared Study of the Dominant Conformation and Hydrogen-Bonding Properties of a Series of Anilide Antiandrogens," J. Med. Chem., 34: 447-455 (1991).
Ng, R. A., "Synthesis and SAR of Potent and Selective Androgen Receptor Antagonists: 5,6-Dicholoro-benzimidazole Derivatives," Bioorganic & Medicinal Chemistry Letters, 17: 784-788 (2007).
Ng, R. A., "Synthesis of Potent and Tissue-Selective Androgen Receptor Modulators (SARMs): 2-(2,2,2)-Trifluoroethyl-benzimidazole Scaffold," Bioorganic & Medicinal Chemistry Letters, 17: 1784-1787 (2007).
Obinata, R, et al., "Stereodivergent Construction of Aminidiols with a CF3 Group," *Organic Letters* 12(19):4316-4319 (2010).
Ostrowski, J., et al., "Pharmacological and X-Ray Structural Characterization of a Novel Selective Androgen Receptor Modulator: Potent Hyperanabolic Stimulation of Skeletal Muscle with Hypostimulation of Prostate in Rats," Endocrinology, 148(1): 4-12 (Jan. 2007).
Piu, F., et al., "Pharmacological Characterization of AC-262536, a Novel Selective Androgen Receptor Modulator," Journal of Steroid Biochemistry & Molecular Biology, 109: 129-137 (2008).
Riedmaier, et al., "Influence of Testosterone and a Novel SARM on Gene Expression in Whole Blood of *Macaca fascicularis*," *Journal of Steroid Biochemistry and Molecular Biology*, 114:167-173 (2009).
Salvati, M. E., et al., "Identification and Optimization of a Novel Series of [2.2.1]-oxabicyclo imide-based Androgen Receptor Antagonists," Bioorganic & Medicinal Chemistry Letters, 18: 1910-1915 (2008).
Schafer, S. and Kolkhof, P., "Failure is an Option: Learning From Unsuccessful Proof-of-Concept Trials," *Drug Discovery Today*, 13(21/22):913-916 (2008).
Sun, C., et al. "Discovery of Potent, Orally-Active, and Muscle-Selective Androgen Receptor Modulators Based on an N-Aryl-hydroxybicyclohydantoin Scaffold," J. Med. Chem. 49(26): 7596-7599 (2006).
Sundar et al., BMJ Case Rep. Feb. 25, 2012, Abstract.
Tucker, H., et al., "Nonsterodial Antiandrogens, Synthesis and Structure-Activity Relationships of 3-Substituted Derivatives of 2-Hydroxypropionanilides," J. Med. Chem., 31: 954-959 (1988).
Vajda, E. G., et al., Pharmacokinetics and Pharmacodynamics of LGD-3303 [9-Cholor-2-ethyl-1-methyl-3-(2,2,2-trifluoroethyl)-3H-pyrrolo-[3,2-f]quinolin-7(6H)-one], an Orally Available Nonsteroidal-Selective Androgen Receptor Modulator, The Journal of Pharmacology and Experimental Therapeutics, 328(2): 663-670 (2009).
Van Oeveren, A., et al., "Novel Selective Androgen Receptor Modulators: SAR Studies on 6-bisalkylamino-2-quinolinones," Bioorganic & Medicinal Chemistry Letters, 17: 1527-1531 (2007).

Wang, Z. et al., "Anti-Inflammatory Properties and Regulatory Mechanism of a Novel Derivative of Artemisinin in Experimental Autoimmune Encephalomyelitis," The Journal of Immunology, J Immunol 179;5958-5965 (2007).
Zeng, C., et al., "Efficient Synthesis of (2R,3S)-2-amino-3-(benzyloxy)-4,4,4-trifluorobutanoic acid (4,4,4-trifluoro-OBn-D-allothreonine)," Tetrahedron Letters, 51: 5361-5363 (2010).
Zhang, X., et al., "Design, Synthesis, and in Vivo SAR of a Novel Series of Pyrazolines as Potent Selective Androgen Receptor Modulators," J. Med. Chem, 50(16): 3857-3869 (2007).
Zhang, X., et al., "Synthesis and SAR of Novel Hydantoin Derivatives as Selective Androgen Receptor Modulators," Bioorganic & Medicinal Chemistry Letters, 16: 5763-5766 (2006).
International Search Report and Written Opinion for Int'l Application No. PCT/US2009/001035 entitled: Selective Androgen Receptor Modulators; Dated: Aug. 7, 2009.
International Preliminary Report on Patentability for Int'l Application No. PCT/US2009/001035 entitled: Selective Androgen Receptor Modulators; Dated: Aug. 24, 2010.
International Search Report and Written Opinion for Int'l Application No. PCT/US2010/30480 entitled: Selective Androgen Receptor Modulators; Dated: Jun. 9, 2010.
International Preliminary Report on Patentability for Int'l Application No. PCT/US2010/030480 entitled: Selective Androgen Receptor Modulators; Dated: Oct. 11, 2011.
International Search Report and Written Opinion for Int'l Application No. PCT/US2011/023768 entitled: Selective Androgen Receptor Modulators; Dated: Mar. 25, 2011.
International Preliminary Report on Patentability for Int'l Application No. PCT/US2011/023768 entitled: Selective Androgen Receptor Modulators; Dated: Aug. 7, 2012.
European Search Report for European Application No. 11740437.6 entitled: Selective Androgen Receptor Modulators; Dated: Apr. 26, 2013.
International Search Report and Written Opinion for International Application No. PCT/US2011/053375 entitled: Selective Androgen Receptor Modulators; Dated: Jan. 16, 2012.
International Preliminary Report on Patentability for International Application No. PCT/US2011/053375 entitled: Selective Androgen Receptor Modulators; Dated: Apr. 2, 2013.
Notice of Allowance and Fees Due for U.S. Appl. No. 12/378,812, entitled: Selective Androgen Receptor Modulators; Date Mailed: Jul. 21, 2011.
Non-Final Office Action for U.S. Appl. No. 12/541,489, entitled: Selective Androgen Receptor Modulators; Mailing Date: Aug. 4, 2011.
Non-Final Office Action for U.S. Appl. No. 12/541,489, entitled: Selective Androgen Receptor Modulators; Mailing Date: Oct. 25, 2011.
Notice of Allowance for U.S. Appl. No. 12/541,489, entitled: Selective Androgen Receptor Modulators; Date Mailed: May 10, 2012.
Office Action for U.S. Appl. No. 12/806,636, entitled: Selective Androgen Receptor Modulators; Date Mailed: Sep. 12, 2012.
Notice of Allowance for U.S. Appl. No. 12/806,636, entitled: Selective Androgen Receptor Modulators; Date Mailed: Feb. 1, 2013.
Non-Final Office Action for U.S. Appl. No. 13/570,417, entitled: Selective Androgen Receptor Modulators; Date Mailed: Apr. 24, 2013.
Notice of Allowance for U.S. Appl. No. 13/570,417, entitled: Selective Androgen Receptor Modulators; Date Mailed: Sep. 17, 2013.
Non-Final Office Action for U.S. Appl. No. 13/175,306, entitled: Selective Androgen Receptor Modulators; Date Mailed: Oct. 31, 2012.
Final Office Action for U.S. Appl. No. 13/175,306, entitled: Selective Androgen Receptor Modulators; Date Mailed: Apr. 5, 2013.
Notice of Allowance and Fees Due for U.S. Appl. No. 13/175,306, entitled: Selective Androgen Receptor Modulators; Date Mailed: Sep. 18, 2013.

\* cited by examiner

SELECTIVE ANDROGEN RECEPTOR MODULATORS

RELATED APPLICATION

This application is the U.S. National Stage of International Application No. PCT/US2011/023768, filed Feb. 4, 2011, which designates the U.S., published in English, and claims the benefit of U.S. Provisional Application No. 61/301,492, filed Feb. 4, 2010. The entire teachings of the above applications are incorporated herein by reference.

BACKGROUND OF THE INVENTION

Androgen signaling is mediated through the androgen receptor (AR) and is a nuclear signaling pathway of tremendous importance in mammals. In addition to its primary role in sexual development, maturation and maintenance of sexual function in both males and females, this critical hormone signaling pathway affects a large number of non-sexual tissues including, bone, muscle, CNS, liver, etc. In humans, testosterone and dihydrotestosterone are the primary ligands that mediate AR-signaling. Both are high affinity ligands for AR, with dihydrotestosterone having somewhat higher affinity. Testosterone is converted to dihydrotestosterone through the action of 5α-reductase enzymes and is converted to 17β-estradiol (potent endogenous estrogen) through the action of P-450 aromatase enzymes. AR signaling is mediated by binding of an AR ligand to AR in the cellular cytosol, homodimerization of two AR receptors and nuclear location of the ligand bound dimer to the cell nucleus where the complex associates with various coactivators as well as Androgen Response Elements (palindrome-like sequences of DNA) which serve as activation sites for certain AR-mediated genes. Due to the very large number of AR target tissues, both sexual and non-sexual, androgens such as testosterone and dihydrotestosterone have a number of potentially desirable actions as well as non-desirable actions depending on the particular individual's age, sex, therapeutic need, etc. In the adult male and female, certain positive consequences of AR-agonist signaling can be generalized as including increased bone mineral density and a corresponding reduction of risk of bone fractures. Accordingly, androgen supplementation can be very valuable in the prevention or treatment of osteoporosis where the osteoporosis might originate from any number of different causes, such as corticosteroid induced osteoporosis and age-related osteoporosis (e.g. postmenopausal). Likewise, males and females respond to agonist supplementation with an increase in muscle mass and very often a decrease in fat mass. This is beneficial in a very large number of treatment modalities. For example, there are many wasting syndromes associated with different disease states where the therapeutic goal is for a patient to maintain weight and function, such as the treatment of cancer associated cachexia, AIDs-related cachexia, anorexia and many more. Other muscle-wasting disorders such as muscular dystrophy in its many forms as well as related disorders might be treated to advantage with androgens. The increase in muscle mass with concomitant reduction in fat mass associated with anabolic androgen action has additional health benefits for many men and women including potentially increased sensitivity to insulin. Androgen supplementation is also associated with reduction of high triglycerides, though there is a general correlation with androgen use and decreased HDL levels and in some cases, increased LDL levels. In the CNS, numerous laudatory benefits have been associated with androgen supplementation including improved sexual desire and functioning, increased cognition, memory, sense of well being and possible decrease in risk of Alzheimer's disease.

Androgen antagonists have been used in treating prostate cancer, where blockade of androgen signaling is desired whereas some androgens agonists (e.g. dihydrotestosterone) stimulate the hypertrophy of prostate tissue and may be a causative factor in prostate cancer. Androgen agonist activity is often associated with stimulation of benign prostate hyperplasia, a disease characterized by an enlarged prostate often accompanied by discomfort and difficulty in urination due to blockage of the urethra. As a result, androgen antagonists have efficacy in the reduction of the size of the prostate and the corresponding symptoms of benign prostate hyperplasia, though it is much more common to use a 5α-reductase inhibitor (e.g. finasteride) as such inhibitors do not decrease androgen signaling systemically to the same extent as a typical anti-androgen (e.g. bicalutamide), but rather reduce androgen drive more site specifically to where testosterone to DHT conversion occurs such as the prostate and scalp. Androgen antagonists also find utility in the treatment of hirsutism in women as well as the treatment of acne. Androgens are generally contraindicated in conditions that are treated with androgen antagonists since they can exacerbate the symptoms that are being treated.

Ideally, an androgen would retain the benefits of androgen agonists while minimizing the stimulatory effects on the prostate in males as well as some of the other untoward effects of androgens including masculinization of women and increase in acne in both sexes. Androgens that demonstrate tissue selective effects compared to the benchmarks testosterone and/or dihydrotestosterone are typically referred to as androgen receptor modulators or more often, selective androgen receptor modulators (SARMs). At the far end of potential selectivity, an ideal SARM would demonstrate no prostate stimulation while maintaining or growing muscle sufficient to effectively mimic the effects of testosterone or dihydrotestosterone. The growing appreciation of the positive contribution that SARMs can make in the many therapeutic areas where androgen activity is desirable has led to a large amount of research into this important area. Due to a compelling need for novel and effective androgen therapies with potentially reduced side effects, novel and effective SARM compounds are urgently needed.

SUMMARY OF THE INVENTION

In certain embodiments, this invention describes a compound of Formula (I) or a pharmaceutically acceptable salt thereof:

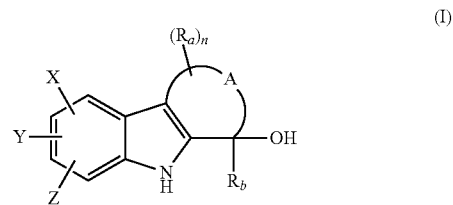

wherein:

X, Y and Z are independently selected from the group consisting of hydrogen, halogen, CN, $C_{1-4}$ alkyl, $C_{1-3}$ hydroxyalkyl, $C_{1-3}$ haloalkyl, $NO_2$, $NH_2$, $OC_{1-3}$alkyl and OH; with the proviso that at least one of X, Y and Z is not hydrogen;

each $R_a$ is independently selected from the group consisting of halogen, OH, NH(CO)$C_{1-6}$ alkyl, $C_{1-4}$ alkyl (wherein said $C_{1-4}$ alkyl is optionally substituted with from 1-2 substituents each independently selected from the group consisting of CN, OH and O$C_{1-3}$ alkyl), $C_{1-5}$ haloalkyl, monocyclic aryl (wherein said monocyclic aryl is optionally substituted with from 1-3 substituents each independently selected from the group consisting of $C_{1-3}$ alkyl, $C_{1-5}$ haloalkyl, CN, halogen, OH and O$C_{1-3}$ alkyl), benzyl (wherein the phenyl group of said benzyl is optionally substituted with from 1-3 substituents each independently selected from the group consisting of halogen, $C_{1-3}$ alkyl, S(O)$_{0-2}C_{1-3}$ alkyl, S(O)$_{0-2}$-phenyl, O—$C_{1-6}$ alkyl, and OCF$_3$), C(O)—$C_{1-10}$ alkyl, SO$_3$—, PO$_3$—, SO$_2$NR$_b$R$_b$, and C(O)phenyl;

$R_b$ is independently selected from the group consisting of $C_{1-4}$ alkyl (wherein said $C_{1-4}$ alkyl is optionally substituted with from 1-2 substituents each independently selected from the group consisting of CN, OH and OPh (wherein said Ph is optionally substituted with 1-2 substituents each independently selected from the group consisting of halogen, OH, CN and O$C_{1-3}$ alkyl)), $C_{1-5}$ haloalkyl, monocyclic aryl (wherein said monocyclic aryl is optionally substituted with from 1-3 substituents each independently selected from the group consisting of $C_{1-3}$ alkyl, $C_{1-5}$ haloalkyl, CN, halogen, OH and O$C_{1-3}$ alkyl), and benzyl (wherein the phenyl group of said benzyl is optionally substituted with from 1-3 substituents each independently selected from the group consisting of halogen, $C_{1-3}$ alkyl, CN, S(O)$_{0-2}C_{1-3}$ alkyl, S(O)$_{0-2}$-phenyl, O—$C_{1-6}$ alkyl, and OCF$_3$);

A is a 2-5 membered carbon alkyl linker selected from the group consisting of

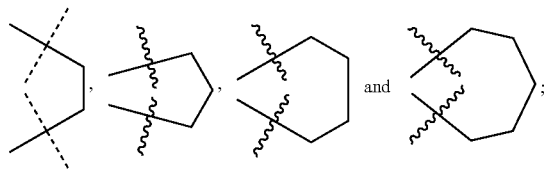

and n is 0, 1, 2 or 3.

In certain embodiments, this invention describes a compound of Formula (II) or a pharmaceutically acceptable salt thereof:

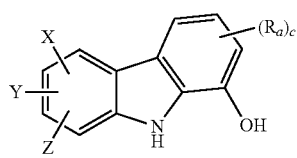

wherein:
c is 0, 1, 2, or 3; and
$R_a$, X, Y and Z are as defined herein;
with the proviso that at least two of X, Y and Z are each independently halogen, NO$_2$ or CN; provided that two of X, Y and Z are not both Br.

This invention also provides methods of treating a disease, syndrome, illness, or symptom associated with insufficient androgen levels in a mammal in need thereof, wherein said method comprises the administration to said mammal of an effective amount of a compound of the invention or a pharmaceutically acceptable salt thereof.

These and other aspects of the invention are described in detail herein.

DETAILED DESCRIPTION OF THE INVENTION

In certain embodiments, this invention describes a compound of Formula (I) or a pharmaceutically acceptable salt thereof:

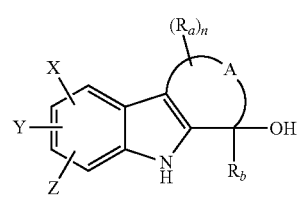

wherein:
X, Y and Z are independently selected from hydrogen, halogen, CN, $C_{1-4}$ alkyl, $C_{1-3}$ hydroxyalkyl, $C_{1-3}$ haloalkyl, NO$_2$, NH$_2$, $C_{1-3}$alkyl and OH; with the proviso that at least one of X, Y and Z is not hydrogen;

each $R_a$ is independently selected from halogen, OH, NH(CO)$C_{1-6}$ alkyl, $C_{1-4}$ alkyl (wherein said $C_{1-4}$ alkyl is optionally substituted with from 1-2 substituents each independently selected from CN, OH and O$C_{1-3}$ alkyl), $C_{1-5}$ haloalkyl, monocyclic aryl (wherein said monocyclic aryl is optionally substituted with from 1-3 substituents each independently selected from $C_{1-3}$ alkyl, $C_{1-5}$ haloalkyl, CN, halogen, OH and O$C_{1-3}$ alkyl), benzyl (wherein the phenyl group of said benzyl is optionally substituted with from 1-3 substituents each independently selected from halogen, $C_{1-3}$ alkyl, S(O)$_{0-2}C_{1-3}$ alkyl, S(O)$_{0-2}$-phenyl, O—$C_{1-6}$ alkyl, and OCF$_3$), C(O)—$C_{1-10}$ alkyl, SO$_3$—, PO$_3$—, SO$_2$NR$_b$R$_b$, and C(O)phenyl;

$R_b$ is independently selected from $C_{1-4}$ alkyl (wherein said $C_{1-4}$ alkyl is optionally substituted with from 1-2 substituents each independently selected from CN, OH, OPh (wherein said Ph is optionally substituted with 1-2 substituents each independently selected from the group consisting of halogen, OH, CN and O$C_{1-3}$ alkyl), $C_{1-5}$ haloalkyl, monocyclic aryl (wherein said monocyclic aryl is optionally substituted with from 1-3 substituents each independently selected from the group consisting of $C_{1-3}$ alkyl, $C_{1-5}$ haloalkyl, CN, halogen, OH and O$C_{1-3}$ alkyl), and benzyl (wherein the phenyl group of said benzyl is optionally substituted with from 1-3 substituents each independently selected from the group consisting of halogen, $C_{1-3}$ alkyl, CN, S(O)$_{0-2}C_{1-3}$ alkyl, S(O)$_{0-2}$-phenyl, O—$C_{1-6}$ alkyl, and OCF$_3$);

A is a 2-5 membered carbon alkyl linker selected from the group consisting of

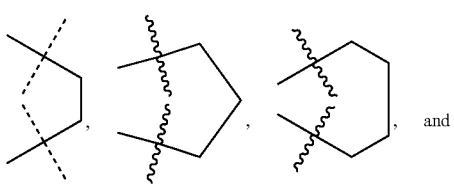

and

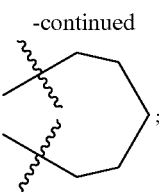

and n is 0, 1, 2 or 3.

In certain embodiments of this invention, for the compound of Formula (I), X, Y and Z are independently selected from hydrogen, halogen, $C_{1-3}$ haloalkyl and CN; with the proviso that at least one of X, Y and Z is not hydrogen.

In some embodiments of this invention, for the compound of Formula (I), X, Y and Z are independently selected from hydrogen, chlorine, fluorine, $CF_3$ and CN; with the proviso that at least one of X, Y and Z is not hydrogen.

In certain embodiments of this invention, for the compound of Formula (I), each $R_a$ is independently selected from halogen, $C_{1-4}$ alkyl and $C_{1-5}$ haloalkyl.

In some embodiments of this invention, for the compound of Formula (I), each $R_a$ is independently selected from halogen, $C_{1-2}$ alkyl and $C_{1-2}$ haloalkyl.

In other embodiments of this invention, for the compound of Formula (I), each $R_a$ is independently selected from chlorine, fluorine, $CH_3$, $CH_3CH_2$, $CF_3$, and $CF_3CF_2$.

In other embodiments of this invention, for the compound of Formula (I), each $R_a$ is independently selected from fluorine, $CH_3$, and $CF_3$.

In certain embodiments of this invention, for the compound of Formula (I), $R_b$ is $C_{1-2}$ alkyl or $C_{1-2}$ haloalkyl.

In some embodiments of this invention, for the compound of Formula (I), $R_b$ is $CH_3$, $CH_3CH_2$, $CF_3$, or $CF_3CF_2$.

In some embodiments of this invention, for the compound of Formula (I), $R_b$ is $CH_3$, $CF_3$, or $CF_3CF_2$.

In certain embodiments of this invention, for the compound of Formula (I), A is a carbon linker selected from the group consisting of:

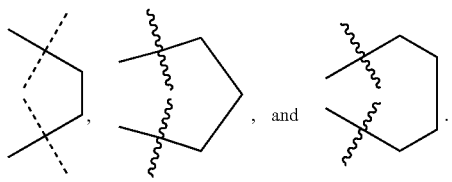

In certain embodiments of this invention, for the compound of Formula (I), n is 0, 1 or 2.

In some embodiments of the invention, for the compounds of Formula (I), X and Y are hydrogen; Z is CN; each $R_a$ is independently selected from the group consisting of fluorine, $CH_3$ and $CF_3$; $R_b$ is $CH_3$, $CF_3$, or $CF_3CF_2$;
A is a carbon linker selected from the group consisting of:

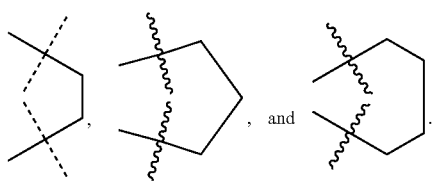

n is 0, 1 or 2.

In some embodiments of the invention, for the compounds of Formula (I), X is hydrogen; Y is $CF_3$; Z is CN; each $R_a$ is independently selected from the group consisting of fluorine, $CH_3$ and $CF_3$; $R_b$ is selected from the group consisting of $CH_3$, $CF_3$, and $CF_3CF_2$;
A is:

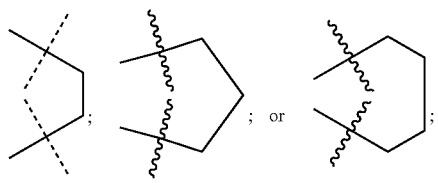

and
n is 0, 1 or 2.

In some embodiments of the invention, for the compounds of Formula (I), X is hydrogen; Y and Z are chlorine; each $R_a$ is independently selected from the group consisting of fluorine, $CH_3$ and $CF_3$; $R_b$ is selected from the group consisting of $CH_3$, $CF_3$, and $CF_3CF_2$;
A is:

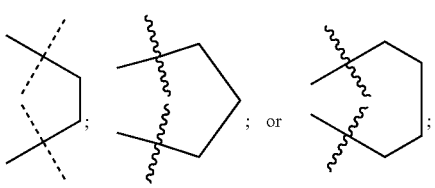

and
n is 0, 1 or 2.

In some embodiments of the invention, for the compounds of Formula (I), X is hydrogen; Y is chlorine; Z is fluorine; each $R_a$ is independently selected from fluorine, $CH_3$ or $CF_3$; $R_b$ is $CH_3$, $CF_3$, and $CF_3CF_2$; A is:

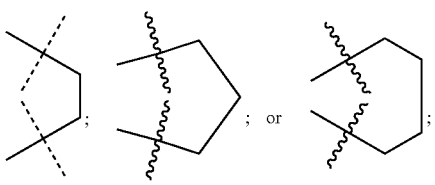

and
n is 0, 1 or 2.

In some embodiments of the invention, for the compounds of Formula (I), X, Y and Z are chlorine; each $R_a$ is independently selected from fluorine, $CH_3$ or $CF_3$; $R_b$ is $CH_3$, $CF_3$, and $CF_3CF_2$; A is:

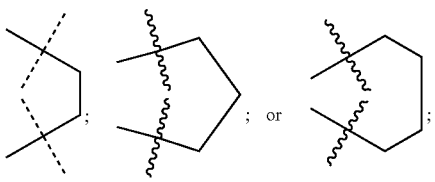

and
n is 0, 1 or 2.

In some embodiments, this invention describes a compound of Formula (Ia) or a pharmaceutically acceptable salt thereof:

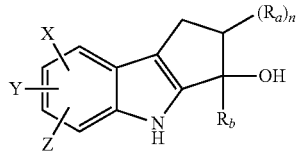

(Ia)

wherein:

X, Y, Z, $R_a$, $R_b$ and n are as defined for formula I.

In certain embodiments of this invention, for the compound of Formula (Ia), X, Y and Z are independently selected from hydrogen, halogen, $C_{1-3}$ haloalkyl and CN; with the proviso that at least one of X, Y and Z is not hydrogen.

In some embodiments of this invention, for the compound of Formula (Ia), X, Y and Z are independently selected from hydrogen, chlorine, fluorine, $CF_3$ and CN; with the proviso that at least one of X, Y and Z is not hydrogen.

In certain embodiments of this invention, for the compound of Formula (Ia), each $R_a$ is independently selected from halogen, $C_{1-4}$ alkyl and $C_{1-5}$ haloalkyl.

In some embodiments of this invention, for the compound of Formula (Ia), each $R_a$ is independently selected from halogen, $C_{1-2}$ alkyl and $C_{1-2}$ haloalkyl.

In other embodiments of this invention, for the compound of Formula (Ia), each $R_a$ is independently selected from chlorine, fluorine, $CH_3$, $CH_3CH_2$, $CF_3$, and $CF_3CF_2$.

In other embodiments of this invention, for the compound of Formula (Ia), each $R_a$ is independently selected from fluorine, $CH_3$, and $CF_3$.

In certain embodiments of this invention, for the compound of Formula (Ia), $R_b$ is $C_{1-2}$ alkyl or $C_{1-2}$ haloalkyl.

In some embodiments of this invention, for the compound of Formula (Ia), $R_b$ is $CH_3$, $CH_3CH_2$, $CF_3$, or $CF_3CF_2$.

In some embodiments of this invention, for the compound of Formula (Ia), $R_b$ is $CH_3$, $CF_3$, or $CF_3CF_2$.

In certain embodiments of this invention, for the compound of Formula (Ia), n is 0, 1 or 2.

In some embodiments of the invention, for the compounds of Formula (Ia), X and Y are hydrogen; Z is CN; each $R_a$ is independently selected from fluorine, $CH_3$ and $CF_3$; $R_b$ is $CH_3$, $CF_3$, or $CF_3CF_2$; and n is 0, 1 or 2.

In some embodiments of the invention, for the compounds of Formula (Ia), X is hydrogen; Y is $CF_3$; Z is CN; each $R_a$ is independently selected from fluorine, $CH_3$ and $CF_3$; $R_b$ is $CH_3$, $CF_3$, or $CF_3CF_2$; and n is 0, 1 or 2.

In some embodiments of the invention, for the compounds of Formula (Ia), X is hydrogen; Y and Z are chlorine; each $R_a$ is independently selected from fluorine, $CH_3$ or $CF_3$; $R_b$ is $CH_3$, $CF_3$, or $CF_3CF_2$; and n is 0, 1 or 2.

In some embodiments of the invention, for the compounds of Formula (Ia), X is hydrogen; Y is chlorine; Z is fluorine; each $R_a$ is independently selected from fluorine, $CH_3$ and $CF_3$; $R_b$ is $CH_3$, $CF_3$, or $CF_3CF_2$; and n is 0, 1 or 2.

In some embodiments of the invention, for the compounds of Formula (Ia), X, Y and Z are chlorine; each $R_a$ is independently selected from fluorine, $CH_3$ or $CF_3$; $R_b$ is $CH_3$, $CF_3$, and $CF_3CF_2$; and n is 0, 1 or 2.

In some embodiments, this invention describes a compound of Formula (Ib) or a pharmaceutically acceptable salt thereof:

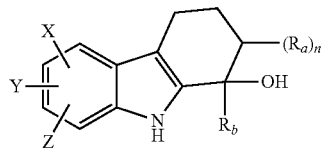

(Ib)

wherein:

X, Y, Z, $R_a$, $R_b$ and n are as defined for formula I.

In certain embodiments of this invention, for the compound of Formula (Ib), X, Y and Z are independently selected from hydrogen, halogen, $C_{1-3}$ haloalkyl and CN; with the proviso that at least one of X, Y and Z is not hydrogen.

In some embodiments of this invention, for the compound of Formula (Ib), X, Y and Z are independently selected from hydrogen, chlorine, fluorine, $CF_3$ and CN; with the proviso that at least one of X, Y and Z is not hydrogen.

In certain embodiments of this invention, for the compound of Formula (Ib), each $R_a$ is independently selected from halogen, $C_{1-4}$ alkyl and $C_{1-5}$ haloalkyl.

In some embodiments of this invention, for the compound of Formula (Ib), each $R_a$ is independently selected from halogen, $C_{1-2}$ alkyl and $C_{1-2}$ haloalkyl.

In other embodiments of this invention, for the compound of Formula (Ib), h each $R_a$ is independently selected from chlorine, fluorine, $CH_3$, $CH_3CH_2$, $CF_3$, and $CF_3CF_2$.

In other embodiments of this invention, for the compound of Formula (Ib), each $R_a$ is independently selected from fluorine, $CH_3$, and $CF_3$.

In certain embodiments of this invention, for the compound of Formula (Ib), $R_b$ is $C_{1-2}$ alkyl or $C_{1-2}$ haloalkyl.

In some embodiments of this invention, for the compound of Formula (Ib), $R_b$ is $CH_3$, $CH_3CH_2$, $CF_3$, or $CF_3CF_2$.

In some embodiments of this invention, for the compound of Formula (Ib), $R_b$ is $CH_3$, $CF_3$, or $CF_3CF_2$.

In certain embodiments of this invention, for the compound of Formula (Ib), n is 0, 1 or 2.

In some embodiments of the invention, for the compounds of Formula (Ib), X and Y are hydrogen; Z is CN; each $R_a$ is independently selected from fluorine, $CH_3$ or $CF_3$; $R_b$ is $CH_3$, $CF_3$, and $CF_3CF_2$; and n is 0, 1 or 2.

In some embodiments of the invention, for the compounds of Formula (Ib), X is hydrogen; Y is $CF_3$; Z is CN; each $R_a$ is independently selected from fluorine, $CH_3$ and $CF_3$; $R_b$ is $CH_3$, $CF_3$, or $CF_3CF_2$; and n is 0, 1 or 2.

In some embodiments of the invention, for the compounds of Formula (Ib), X is hydrogen; Y and Z are chlorine; each $R_a$ is independently selected from fluorine, $CH_3$ and $CF_3$; $R_b$ is $CH_3$, $CF_3$, or $CF_3CF_2$; and n is 0, 1 or 2.

In some embodiments of the invention, for the compounds of Formula (Ib), X is hydrogen; Y is chlorine; Z is fluorine; each $R_a$ is independently selected from fluorine, $CH_3$ and $CF_3$; $R_b$ is $CH_3$, $CF_3$, or $CF_3CF_2$; and n is 0, 1 or 2.

In some embodiments of the invention, for the compounds of Formula Ib, X, Y and Z are chlorine; each $R_a$ is independently selected from fluorine, $CH_3$ and $CF_3$; $R_b$ is $CH_3$, $CF_3$, or $CF_3CF_2$; and n is 0, 1 or 2.

In some embodiments, this invention describes a compound of Formula (Ic) or a pharmaceutically acceptable salt thereof:

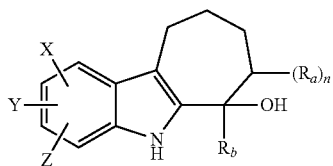

(Ic)

wherein:

X, Y, Z, $R_a$, $R_b$ and n are as defined for formula I.

In certain embodiments of this invention, for the compound of Formula (Ic), X, Y and Z are independently selected from hydrogen, halogen, $C_{1-3}$ haloalkyl and CN; with the proviso that at least one of X, Y and Z is not hydrogen.

In some embodiments of this invention, for the compound of Formula (Ic), X, Y and Z are independently selected from hydrogen, chlorine, fluorine, $CF_3$ and CN; with the proviso that at least one of X, Y and Z is not hydrogen.

In certain embodiments of this invention, for the compound of Formula (Ic), each $R_a$ is independently selected from halogen, $C_{1-4}$ alkyl and $C_{1-5}$ haloalkyl.

In some embodiments of this invention, for the compound of Formula (Ic), each $R_a$ is independently selected from halogen, $C_{1-2}$ alkyl and $C_{1-2}$ haloalkyl.

In other embodiments of this invention, for the compound of Formula (Ic), each $R_a$ is independently selected from chlorine, fluorine, $CH_3$, $CH_3CH_2$, $CF_3$, and $CF_3CF_2$.

In other embodiments of this invention, for the compound of Formula (Ic), each $R_a$ is independently selected from fluorine, $CH_3$, and $CF_3$.

In certain embodiments of this invention, for the compound of Formula (Ic), $R_b$ is $C_{1-2}$ alkyl or $C_{1-2}$ haloalkyl.

In some embodiments of this invention, for the compound of Formula (Ic), $R_b$ is $CH_3$, $CH_3CH_2$, $CF_3$, or $CF_3CF_2$.

In some embodiments of this invention, for the compound of Formula (Ic), $R_b$ is $CH_3$, $CF_3$, or $CF_3CF_2$.

In certain embodiments of this invention, for the compound of Formula (Ic), n is 0, 1 or 2.

In some embodiments of the invention, for the compounds of Formula (Ic), X and Y are hydrogen; Z is CN; each $R_a$ is independently selected from fluorine, $CH_3$ and $CF_3$; $R_b$ is $CH_3$, $CF_3$, or $CF_3CF_2$; and n is 0, 1 or 2.

In some embodiments of the invention, for the compounds of Formula (Ic), X is hydrogen; Y is $CF_3$; Z is CN; each $R_a$ is independently selected from fluorine, $CH_3$ and $CF_3$; $R_b$ is $CH_3$, $CF_3$, or $CF_3CF_2$; and n is 0, 1 or 2.

In some embodiments of the invention, for the compounds of Formula (Ic), X is hydrogen; Y and Z are chlorine; each $R_a$ is independently selected from fluorine, $CH_3$ or $CF_3$; $R_b$ is $CH_3$, $CF_3$, and $CF_3CF_2$; and n is 0, 1 or 2.

In some embodiments of the invention, for the compounds of Formula (Ic), X is hydrogen; Y is chlorine; Z is fluorine; each $R_a$ is independently selected from fluorine, $CH_3$ and $CF_3$; $R_b$ is $CH_3$, $CF_3$, or $CF_3CF_2$; and n is 0, 1 or 2.

In some embodiments of the invention, for the compounds of Formula (Ic), X, Y and Z are chlorine; each $R_a$ is independently selected from fluorine, $CH_3$ and $CF_3$; $R_b$ is $CH_3$, $CF_3$, or $CF_3CF_2$; and n is 0, 1 or 2.

In some embodiments of this invention, selected compound of this invention is selected from the following list. (The compound names in the list were generated with the assistance of ChemDraw® versions 8.0, 9.0 and/or 11.0 (CambridgeSoft Corporation, 100 CambridgePark Drive, Cambridge, Mass. 02140 USA)). When the stereochemistry at a chiral center is not defined in the compound name this indicates that the sample prepared contained a mixture of isomers at this center.

6,7-Dichloro-1-methyl-2,3,4,9-tetrahydro-1H-carbazol-1-ol;
1-Hydroxy-1-methyl-2,3,4,9-tetrahydro-1H-carbazole-6-carbonitrile;
6,7-Dichloro-1-(trifluoromethyl)-2,3,4,9-tetrahydro-1H-carbazol-1-ol;
1-Hydroxy-1-(trifluoromethyl)-2,3,4,9-tetrahydro-1H-carbazole-6-carbonitrile;
5,6-Dichloro-1(trifluoromethyl)-2,3,4,9-tetrahydro-1H-carbazol-1ol;
6,7-Dichloro-1-(perfluoroethyl)-2,3,4,9-tetrahydro-1H-carbazol-1-ol;
1-Hydroxy-1-(perfluoroethyl)-2,3,4,9-tetrahydro-1H-carbazole-6-carbonitrile;
6,8-Dichloro-1-(trifluoromethyl)-2,3,4,9-tetrahydro-1H-carbazol-1-ol;
(S)-6,7-Dichloro-1-(trifluoromethyl)-2,3,4,9-tetrahydro-1H-carbazol-1-01;
(R)-6,7-dichloro-1-(trifluoromethyl)-2,3,4,9-tetrahydro-1H-carbazol-1-ol;
(R)-6,8-Dichloro-1-(trifluoromethyl)-2,3,4,9-tetrahydro-1H-carbazol-1-ol;
2,4-Dichloro-6-(trifluoromethyl)-5,6,7,8,9,10-hexahydrocyclohept[b]indol-6-ol;
6,7-Dichloro-2-fluoro-1-(trifluoromethyl)-2,3,4,9-tetrahydro-1H-carbazol-1-ol;
5,8-Dichloro-1-(trifluoromethyl)-2,3,4,9-tetrahydro-1H-carbazol-1-ol;
5-Chloro-6-fluoro-1-(trifluoromethyl)-2,3,4,9-tetrahydro-1H-carbazol-1-ol;
5,6-Dichloro-2-fluoro-1-(trifluoromethyl)-2,3,4,9-tetrahydro-1H-carbazol-1-ol;
7-Chloro-6-fluoro-1-(trifluoromethyl)-2,3,4,9-tetrahydro-1H-carbazol-1-ol;
8-Chloro-6-fluoro-1-(trifluoromethyl)-2,3,4,9-tetrahydro-1H-carbazol-1-ol;
8-Chloro-6-fluoro-1,2-bis(trifluoromethyl)-2,3,4,9-tetrahydro-1H-carbazol-1-ol;
6,7-Dichloro-2,2-difluoro-1-(trifluoromethyl)-2,3,4,9-tetrahydro-1H-carbazol-1-ol;
6,8-Dichloro-2,2-difluoro-1-(trifluoromethyl)-2,3,4,9-tetrahydro-1H-carbazol-1-ol;
5,6,8-Trichloro-1-(trifluoromethyl)-2,3,4,9-tetrahydro-1H-carbazol-1-ol;
5,7-Dichloro-3-(trifluoromethyl)-1,2,3,4-tetrahydrocyclopenta[b]indol-3-ol;
5,6-Dichloro-2-methyl-1-(trifluoromethyl)-2,3,4,9-tetrahydro-1H-carbazol-1-ol;
5,6,7-Trichloro-1-(trifluoromethyl)-2,3,4,9-tetrahydro-1H-carbazol-1-ol;
7,8-Dichloro-1-(trifluoromethyl)-2,3,4,9-tetrahydro-1H-carbazol-1-ol;
6,7-Dichloro-2-methyl-1-(trifluoromethyl)-2,3,4,9-tetrahydro-1H-carbazol-1-ol;
6,7-Dichloro-3-(trifluoromethyl)-1,2,3,4-tetrahydrocyclopenta[b]indol-3-ol;
6-Chloro-8-fluoro-1-(trifluoromethyl)-2,3,4,9-tetrahydro-1H-carbazol-1-ol;
7,8-Dichloro-3-(trifluoromethyl)-1,2,3,4-tetrahydrocyclopenta[b]indol-3-ol; and
1-Hydroxy-1,8-bis(trifluoromethyl)-2,3,4,9-tetrahydro-1H-carbazole-6-carbonitrile,
or a pharmaceutically acceptable salt of any of the foregoing.

In certain embodiments, this invention describes a compound of Formula (II), or a pharmaceutically acceptable salt thereof:

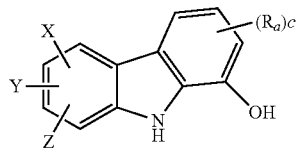

(II)

wherein:
c is 0, 1, 2, or 3; and
$R_a$, X, Y and Z are as defined for formula I;
with the proviso that at least two of X, Y and Z are each independently halogen, $NO_2$ or CN; and provided that two of X, Y and Z are not both Br.

In certain embodiments of this invention, for the compound of Formula (II), X, Y and Z are independently selected from hydrogen, halogen, $C_{1-3}$ haloalkyl and CN; with the proviso that at least two of X, Y and Z are each independently halogen or CN; and provided that two of X, Y and Z are not both Br.

In some embodiments of this invention, for the compound of Formula (II), X, Y and Z are independently selected from hydrogen, chlorine, bromine, $CF_3$ and CN; with the proviso that at least two of X, Y and Z are each independently halogen, or CN; and provided that two of X, Y and Z are not both Br.

In certain embodiments of this invention, for the compound of Formula (II), each $R_a$ is independently selected from halogen, $C_{1-4}$ alkyl, $C_{1-5}$ haloalkyl and benzyl.

In some embodiments of this invention, for the compound of Formula (II), each $R_a$ is independently selected from halogen, $C_{1-2}$ alkyl, $C_{1-2}$ haloalkyl and benzyl.

In other embodiments of this invention, for the compound of Formula (II), each $R_a$ is independently selected from chlorine, fluorine, bromine, $CH_3$ and benzyl.

In other embodiments of this invention, for the compound of Formula (II), each $R_a$ is independently selected from bromine, $CH_3$ and benzyl.

In certain embodiments of this invention, for the compound of Formula (II), c is 0, or 1.

In some embodiments, this invention describes a compound of Formula (IIa), or a pharmaceutically acceptable salt thereof:

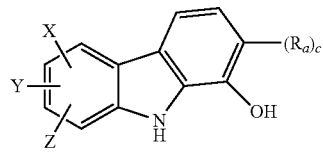

(IIa)

wherein:
c is 0, 1, 2, or 3; and
$R_a$, X, Y and Z are as defined for formula I;
with the proviso that at least two of X, Y and Z are each independently halogen, $NO_2$ or CN; and provided that two of X, Y and Z are not both Br.

In certain embodiments of this invention, for the compound of Formula (IIa), X, Y and Z are independently selected from hydrogen, halogen, $C_{1-3}$ haloalkyl and CN; with the proviso that at least two of X, Y and Z are each independently halogen or CN; and provided that two of X, Y and Z are not both Br.

In some embodiments of this invention, for the compound of Formula (IIa), X, Y and Z are independently selected from hydrogen, chlorine, bromine, $CF_3$ and CN; with the proviso that at least two of X, Y and Z are each independently halogen, or CN; and provided that two of X, Y and Z are not both Br;

In certain embodiments of this invention, for the compound of Formula (IIa), each $R_a$ is independently selected from halogen, $C_{1-4}$ alkyl, $C_{1-5}$ haloalkyl and benzyl.

In some embodiments of this invention, for the compound of Formula (IIa), each $R_a$ is independently selected from halogen, $C_{1-2}$ alkyl, $C_{1-2}$ haloalkyl and benzyl.

In other embodiments of this invention, for the compound of Formula (IIa), each $R_a$ is independently selected from chlorine, fluorine, bromine, $CH_3$ and benzyl.

In other embodiments of this invention, for the compound of Formula (IIa), each $R_a$ is independently selected from bromine, $CH_3$ and benzyl.

In certain embodiments of this invention, for the compound of Formula (IIa), c is 0, or 1.

In some embodiments of the invention, for the compounds of Formula (IIa), X and Y are hydrogen; Z is CN; each $R_a$ is independently selected from bromine and benzyl; c is 0 or 1.

In some embodiments of the invention, for the compounds of Formula (IIa), X and Y are hydrogen; Z is bromine; each $R_a$ is independently selected from bromine and benzyl; c is 0 or 1.

In some embodiments of the invention, for the compounds of Formula (IIa), X and Y are chlorine; Z is hydrogen; each $R_a$ is independently selected from bromine and benzyl; c is 0 or 1.

In some embodiments of the invention, a compound of Formula (III) or pharmaceutically acceptable salt is described,

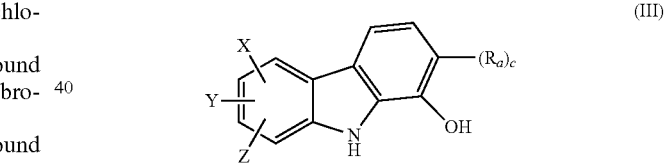

(III)

X and Y are hydrogen; Z is CN; each $R_a$ is independently selected from bromine and benzyl; and c is 0 or 1.

In some embodiments of the invention, for the compounds of Formula (III), X and Y are hydrogen; Z is bromine; each $R_a$ is independently selected from bromine and benzyl; and c is 0 or 1.

In some embodiments of the invention, for the compounds of Formula (III), X and Y are chlorine; Z is hydrogen; each $R_a$ is independently selected from bromine and benzyl; and c is 0 or 1.

In some embodiments of this invention, a compound of this invention is selected from the group below. (The compound names in the list were generated with the assistance of ChemDraw® versions 8.0, 9.0 and/or 11.0 (CambridgeSoft Corporation, 100 CambridgePark Drive, Cambridge, Mass. 02140 USA)).

6-Bromo-9H-carbzol-1-ol;
8-Hydroxy-9H-carbazole-3-carbonitrile;
5,6-Dichloro-9H-carbazol-1-ol;
2-Bromo-6,7-dichloro-9H-carbazol-1-ol;
2-Benzyl-5,6-dichloro-9H-carbazol-1-ol;
2-Benzyl-6,7-dichloro-9H-carbazol-1-ol;
or a pharmaceutically acceptable salt of any of the following.

The invention also relates to pharmaceutical compositions comprising a compound of Formula (I), (Ia), (Ib), (Ic), (II), (IIa) or (III) or any of the structural embodiments described herein and at least one pharmaceutically acceptable excipient.

The invention also provides a method of modulating an androgen receptor in a cell, comprising the administration of a compound to said cell wherein said compound has structural Formula (I), (Ia), (Ib), (Ic), (II), (IIa) or (III) or any of the structural embodiments described herein, or a pharmaceutically acceptable salt thereof.

This invention provides a method of identifying a compound capable of modulating an androgen receptor comprising contacting a cell expressing an androgen receptor with a compound according to Formula (I), (Ia), (Ib), (Ic), (II), (IIa) or (III) and monitoring the effect of the compound on the cell.

This invention also provides a method of treating (e.g., preventing, or ameliorating the symptoms associated with, or reducing the incidence of, reducing the pathogenesis of, facilitating the recovery from or delaying the onset of) a disease, syndrome, illness, or symptom associated with insufficient androgen levels in a mammal in need thereof, wherein said method comprises the administration to said mammal of an effective amount of a compound of Formula (I), (Ia), (Ib), (Ic), (II), (IIa) or (III), or any one of the structural embodiments described herein or a pharmaceutically acceptable salt thereof, or a pharmaceutical composition comprising a compound of Formula (I), (Ia), (Ib), (Ic), (II), (IIa) or (III), or one of the structural embodiments described herein, or a pharmaceutically acceptable salt thereof and a pharmaceutically acceptable excipient. In a particular embodiment, the mammal is a human.

In some embodiments, this invention provides a method of treating (e.g., preventing, or ameliorating the symptoms associated with, or reducing the incidence of, reducing the pathogenesis of, facilitating the recovery from or delaying the onset of) sarcopenia, frailty, multiple sclerosis, osteoporosis, anemia, cognitive impairment, cachexia, muscular dystrophy, weak appetite, low body weight, anorexia nervosa, acne, seborrhea, polycystic ovarian syndrome, hair loss, AIDs wasting, chronic fatigue syndrome, short stature, low testosterone levels, diminished libido, benign prostate hypertrophy, infertility, erectile dysfunction, vaginal dryness, premenstrual syndrome, postmenopausal symptoms, female hormone replacement therapy, male hormone replacement therapy, depression, Type II diabetes, mood disorders, sleep disorders, memory disorders, neurodegenerative disorders, Alzheimer's dementia, attention deficit disorder, senile dementia, coronary artery disease, hirsutism, pain, myalgia, myocardial infarction, stroke, clotting disorders, thromboembolisms, congestive heart disorder, low insulin sensitivity, low glucose utilization, high blood sugar, organ transplant, metabolic syndrome, diabetes, glucose intolerance, hyperinsulinemia, insulin resistance, tooth injury, tooth disease, periodontal disease, liver disease, thrombocytopenia, fatty liver conditions, endometriosis, hot flushes, hot flashes, vasomotor disturbance, stress disorders, dwarfism, dyslipidemia, cardiovascular disease, coronary artery disease, renal disease, thin skin disorders, lethargy, osteopenia, dialysis, irritable bowel syndrome, Crohn's disease, Paget's disease, osteoarthritis, connective tissue disease or disorders, injury, burns, trauma, wounds, bone fracture, atherosclerosis, cachexia, cancer cachexia, and obesity, in a mammal in need thereof comprising the administration to said mammal of an effective amount of a compound according to a structure of Formula (I), (Ia), (Ib), (Ic), (II), (IIa) or (III), or one of the structural embodiments described herein, or a pharmaceutically acceptable salt thereof, or a pharmaceutical composition comprising a compound of structural Formula (I), (Ia), (Ib), (Ic), (II), (IIa) or (III) or one of the structural embodiments described herein including pharmaceutically acceptable salts thereof and a pharmaceutically acceptable excipient. In a particular embodiment, the mammal is a human.

In certain aspects, this invention describes a method of treating (e.g., preventing, or ameliorating the symptoms associated with, or reducing the incidence of, reducing the pathogenesis of, facilitating the recovery from or delaying the onset of) prostate cancer, breast cancer, endometrial cancer, hepatocellular cancer, lymphoma, multiple endocrine neoplasia, vaginal cancer, renal cancer, thyroid cancer, testicular cancer, leukemia, and ovarian cancer in a mammal in need thereof comprising the administration to said mammal of a compound according to a structure of Formula (I), (Ia), (Ib), (Ic), (II), (IIa) or (III), or one of the structural embodiments described herein, or a pharmaceutically acceptable salt thereof, or a pharmaceutical composition comprising a compound of structural Formula (I), (Ia), (Ib), (Ic), (II), (IIa) or (III), or one of the structural embodiments described herein including pharmaceutically acceptable salts thereof and a pharmaceutically acceptable excipient. In a particular embodiment, the mammal is a human.

The term "alkyl" as used herein refers to both straight and branch chain hydrocarbon radicals, having the number of carbon atoms falling within the specified range. For example, $C_{1-4}$ alkyl means that a hydrocarbon radical is attached that may contain anywhere from 1 to 4 carbon atoms with the remaining valence filled in by hydrogen atoms. The definition also includes separately each permutation as though it were separately listed. Thus, $C_{1-2}$ alkyl includes methyl and ethyl. The term $C_{1-3}$ alkyl includes methyl, ethyl, propyl and 2-propyl. The term $C_{1-4}$ alkyl includes methyl, ethyl, n-propyl, 2-propyl, n-butyl, 2-butyl, iso-butyl and tert-butyl. The term $C_{1-5}$ alkyl includes methyl, ethyl, 2-propyl, n-butyl, 2-methylbutyl, tert-butyl, n-pentyl, pentan-2-yl, pentan-3-yl, and tert-pentyl, iso-pentyl.

The term "halogen" as used herein refers to a fluorine, chlorine, bromine or iodine radical.

The term "haloalkyl" refers to an alkyl radical wherein said alkyl radical is the same as defined for the term "alkyl" except that the alkyl radical additionally has from 1 to 5 halogen atoms attached to the alkyl chain. For example, $C_1$ haloalkyl includes
—$CH_2F$, —$CHF_2$, —$CF_3$ and the like, $C_{1-2}$ haloalkyl includes —$CH_2F$, $CHF_2$, $CF_3$, —$CH_2CH_2F$, —$CH_2CHF_2$, —$CH_2CF_3$, —$CF_2CHF_2$, —$CF_2CF_3$ and the like. $C_{1-3}$ haloalkyl is defined to include —$CH_2F$, —$CHF_2$, —$CF_3$, —$CH_2CF_3$, —$CHFCF_3$, —$CF_2CF_3$, —$CHClCH_3$, —$CH_2CH_2Cl$, —$CH_2CH_2CF_3$, and the like. $C_{1-4}$ haloalkyl is defined to include —$CH_2F$, —$CHF_2$, —$CF_3$, —$CH_2CF_3$, —$CHFCF_3$, —$CF_2CF_3$, —$CHClCH_3$, —$CH_2CH_2Cl$, —$CH_2CH_2CF_3$, —$CH_2CH_2CH_2CF_3$, $CHClCF_2CH_2CH_3$, $CF_2CH_2CH_2CHF_2$, $CH_2CH_2CH_2CH_2F$, $CH_2CH_2CH_2CH_2Cl$, and the like.

The term "hydroxyalkyl" refers to an alkyl radical wherein said alkyl radical is the same as defined for the term "alkyl" except that the alkyl radical additionally has from 1 or 2 hydroxyl groups attached to the alkyl chain. For example, $C_{2-4}$ hydroxyalkyl includes 2-hydroxyethyl, 2-hydroxypropyl, 2,4-dihydroxybutyl and the like.

The compounds of this invention may be present as solids and when so present, may be in an amorphous form or they may be crystalline. When the compounds of this invention are in the crystalline form, they might be present as a single polymorph or a mixture of polymorphs or even as a mixture of amorphous material together with one or more distinct polymorphs—the invention is not limited according to any particular solid or liquid state form.

The compounds of this invention contain at least one stereocenter and therefore, exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms. Thus, "R" and "S" denote the relative configurations of substituents around one or more chiral carbon atoms. When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

The compounds of the invention may be prepared as individual isomers by incorporating or starting with a specific isomer, isomer-specific synthesis or resolution from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

Where compounds of this invention include one or more basic sites such as amines, acid addition salts can be made and this invention includes such acid addition salts. Some representative (non-limiting) acid addition salts include hydrochloride, hydrobromide, hydroiodide, acetate, benzenesulfonate, mesylate, besylate, benzoate, tosylate, citrate, tartrate, sulfate, bisulfate, lactate, maleate, mandelate, valerate, laurate, caprylate, propionate, succinate, phosphate, salicylate, napsylate, nitrate, tannate, resorcinate and the like, including multiprotic salts as well as mixtures of the acid addition salts. In cases where an amine is present, this invention also embraces quaternized ammonium salts of those amines. It should be appreciated that N-oxides of amines are also embraced within the definition of the compounds of this invention. Likewise, where compounds of this invention include one or more acid sites such as carboxylic acids, phenols and the like, basic addition salts can be made and this invention includes such basic addition salts. For example, some representative (non-limiting) acidic compounds of this invention may be present as their lithium, sodium, potassium, ammonium, trialkylammonium, calcium, magnesium, barium and the like.

The compounds of this invention can also be present as solvates and such solvates are embraced within the scope of this invention even where not explicitly described. Such solvates are preferably hydrates but can be solvates comprised of other solvents, preferably where those solvents are considered to be non-toxic or at least acceptable for administration to mammals, preferably humans. The solvates can be stoichiometric or non-stoichiometric, singular or in combination. Some exemplary solvates include water, ethanol, acetic acid and the like.

It should be understood that where hydrogen is specifically described or implied, deuterium is optionally included—either at the normal hydrogen to deuterium isotope ratio or, possibly enriched in deuterium up to 100% deuterium at any given position. In particular, some embodiments of this invention can be prepared so as to include high levels of deuterium (>90%) at one or more positions. In a particular embodiment of this invention, a structure of Formula (I) is provided wherein A is defined as including cyclohexyl. In many embodiments of this invention, when A is a cyclohexyl ring, the cyclohexyl will have one or more specified "hydrogens". In accordance, with the explanation in this paragraph, one or more of the hydrogens may be optionally substituted by deuterium and that substitution may range from a very low incorporation to >90% depending on the method used for incorporating the deuterium if a specific method was used.

The therapeutic utility of these compounds includes "treating" a mammal, preferably a human where treating is understood to include treating, preventing, or ameliorating the symptoms associated with, or reducing the incidence of, reducing the pathogenesis of, facilitating the recovery from or delaying the onset of the syndrome, illness, malady or condition being considered. The compounds of this invention can also be useful in states or conditions where no clear deficit, illness or malady per se is perceived but rather, where a preferred condition, sensation, performance, capability or state is obtainable through therapeutic intervention with a compound of this invention.

The compounds of this invention, when used as therapeutics can be administered by any method known to one of skill in the art such as orally, bucally, intravenously, subcutaneously, intramuscularly, transdermally, intradermally, intravascularly, intranasally, sublingually, intracranially, rectally, intratumorally, intravaginally, intraperitonealy, pulmonary, ocularly and intratumorally.

As used herein, the term "effective amount" refers to an amount which, when administered in a proper dosing regimen, is sufficient to treat (therapeutically or prophylactically) the target disorder. For example, and effective amount is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

When administered, the compounds and compositions of this invention maybe given once daily or with multiple daily doses such as twice per day, three times per day and four times per day.

In some embodiments of this invention, a Pharmaceutical composition is referred to and such a Pharmaceutical composition refers to one or more of the compounds of this invention with one or more pharmaceutically acceptable excipients.

In one embodiment of this invention, the compound is administered orally where it can be Formulated for solid dosage administration or liquid dosage administration. Solid dosage administration can be in the form of a tablet, granule, capsule, pill, pellet, powder and the like. Liquid dosage Formulations include syrups, solutions, gels, suspensions, elixirs, emulsions, colloids, oils, and the like.

As mentioned previously, the compounds of this invention may be solids and when present as solids, they maybe of defined particle size. Where the compound of this invention is not particularly water soluble, it is sometimes preferable to administer the compound with a certain particle size—a particle size with a preferred range where the average mean particle size diameter is under 100 microns, or 75 microns, or 50 microns, or 35 microns, or 10 microns or 5 microns.

Solid dosage Formulations will comprise at least one compound of this invention together with one or more pharmaceutical excipients. Those excipients are known to one of skill in the art and include, by way of non-limiting example diluents (monosaccharides, disaccharides and polyhydric alcohols including starch, mannitol, dextrose, sucrose, microcrystalline cellulose, maltodextrin, sorbitol, xylitol, fructose and the like), binders (starch, gelatin, natural sugars, gums, waxes and the like), disintegrants (alginic acid, carboxymethylcellulose (calcium or sodium), cellulose, crocarmellose, crospovidone, microcrystalline cellulose, sodium starch glycolate, agar and the like), acidic or basic buffering agents (citrates, phosphates, gluconates, acetates, carbonates, bicarbonates and the like), chelating agents (edetic acid, dentate calcium, dentate disodium and the like), preservatives (benzoic acid, chlorhexidine gluconate, potassium benzoate, potassium sorbate, sorbic acid, sodium benzoate and the like), glidants and lubricants (calcium stearate, oils, magnesium stearate, magnesium trisilicate, sodium fumarate, colloidal silica, zinc stearate, sodium oleate, stearic acid, and the like), antioxidants and/or preservatives (tocopherols, ascorbates, phenols, and the like) and acidifying agents (citric acid, fumaric acid, malic acid, tartaric acid and the like) as well as coloring agents, coating agents, flavoring agents, suspending agents, desiccants, humectants and other excipients known to those of skill in the art.

The solid dosage Formulations of this invention can be prepared in different forms including most commonly, tablets and capsules. The tablets can be Formulated by a wide variety of methods known to one of skill in the art including, for example, preparing a dry powder mixture of the drug substance in combination with one or more of the excipients granulating the mixture and pressing to together into a tablet and optionally coating the tablet with an enteric or non-enteric coating. The final coat typically includes a light protective pigment such as titanium oxide and a shellac or wax to keep the tablet dry and stable. While not intending to be limited by theory or example, in some instances it might be preferred to prepare the tablets by wet granulating the drug with one or more of the excipients and then extruding the granulated material.

The solid dosage forms of this invention also include capsules wherein the drug is enclosed inside the capsule either as a powder together with optional excipients or as granules containing usually including one or more excipients together with the drug and wherein the granule in turn can be optionally coated, for example, enterically or non-enterically.

In certain embodiments of this invention, the solid dosage Formulations of this invention are Formulated in a sustained release Formulation. Such Formulations are known to those of skill in the art and generally rely on the co-Formulation of the drug with one or more matrix forming substances that slow the release of the androgen receptor modulator thus extending the compound's lifetime in the digestive track and thereby extend the compounds half-life. Some non-limiting matrix forming substances include hydroxypropyl methylcellulose, carbopol, sodium carboxymethylcellulose and the like.

In some embodiments of this invention, the compounds are Formulated for delivery other than via a solid oral dosage form. For example, in certain instances it might be preferable to deliver a compound of this invention by a pulmonary route. A pulmonary route of administration typically means that the compound of this invention is inhaled into the lung where it is absorbed into the circulation. Such a route of administration has the advantage of avoiding a first pass liver effect thereby possibly increasing bioavailability as well as decreasing or eliminating undesirable androgen agonist effects on the liver such as increasing liver enzymes and/or decreasing HDL. Formulating a compound of the invention for pulmonary delivery can be accomplished by micronizing the compound of the invention to a very fine size particle, typically with a mean average diameter of less than 20 microns, or less than 10 microns or between 2 and 5 microns. The powder may then be inhaled by itself or more likely mixed with one or more excipients such as lactose or maltose. The powder can then be inhaled in a dry powder inhaling device either once or multiple times per day depending on the particular compound and the patients need. Other types of pulmonary dosage forms are also embraced by this invention. In an alternative to the dry powder delivery, the compound of this invention may be suspended in an aerosolizing medium and inhaled as a suspension through a meter dosed inhaler or a nebulizer.

The compounds of this invention can be Formulated for transdermal delivery. Effective advantage of these compounds can be taken through a wide variety of transdermal options. For example, the compounds of this invention maybe Formulated for passive diffusion patches where they are preferably embedded in a matrix that allows for slow diffusion of the compound into the treated subject's circulation. For this purpose, the compound is preferably dissolved or suspended in solvents including by way of non-limiting examples one or more of ethanol, water, propylene glycol, and Klucel HF. In some instances, a polymer matrix (e.g. acrylate adhesive) will comprise the bulk of the transdermal Formulation. In some instances, the transdermal Formulations maybe designed to be compatible with alternate transdermal delivery technologies. For example, some transdermal technologies achieve greater and/or more consistent delivery by creating micropores in the skin using radio frequency, heat, ultrasound or electricity. In some cases, the compounds of this invention can be used with microneedle technology wherein the compound is loaded into very small needles which due not need to penetrate the dermis to be effective.

The compounds of this invention may be employed alone or in combination with other therapeutic agents. By way of non-limiting example, the compounds of this invention can be used in combination with anti-lipidemics (statins, fibrates, omega-3 oils, niacinates and the like), bone anti-resorptives (bisphosphonates, estrogens, selective estrogen receptor modulators (SERMs), calcitonin, and the like), bone anabolic agents (PTH and fragments e.g. teriparatide, PTHRP and analogues e.g. BaO58), anti-diabetics (e.g. insulin sensitizers, glucose absorption and synthesis inhibitors (e.g. metformin)), anti-anxiety agents, antidepressants, anti-obesity agents, contraceptive agents, anti-cancer agents, PPARγ agonists (e.g. pioglitazone), and the like. When used in combination, the compounds of this invention may be co-Formulated or co-administered wherein said co-administration does not require dosing at exactly the same time but rather indicates that the patient is undergoing treatment with one or more of the additional agents during the timeframe of treatment with the selective androgen modulators of this invention. Thus, the additional drug(s) for combination treatment can be administered concomitantly, sequentially or separately from the compounds of this invention.

The compounds of this invention may be administered according to different dosage scheduling and the dosage may be adjusted as deemed necessary by the subject or preferably by the subject in consultation with a qualified practitioner of medicine. Dosing of the compounds of this invention can take place by multiple routes and consequently, the dosing schedule and amounts are dependent not only on the particular subject's weight, sex, age, therapy contemplated, etc but also by the route of the drug chosen.

By way of non-limiting example, the compounds of this invention may be dosed by the oral route in a once daily, twice daily, three times daily or more than three times per day depending on the particular needs of that subject, the Formulation of the drug, etc. The dosage will typically be from about 0.01 mg to 500 mg of drug per daily dosage, for example from about 0.1 mg to about 10 mg, such as from about 0.1 mg to about 3 mg, or from about 0.1 mg to about 250 mg of drug per daily dosage, or from about 1 mg to about 150 mg of drug per daily dosage, or from about 5 mg to about 100 mg of drug per daily dosage, or from about 0.1 mg to about 5 mg of drug per daily dosage.

It is understood that the amount of compound dosed per day can be administered every day, every other day, every 2 days, every 3 days, every 4 days, every 5 days, etc. For example, with every other day administration, a 5 mg per day dose can be initiated on Monday with a first subsequent 5 mg per day dose administered on Wednesday, a second subsequent 5 mg per day dose administered on Friday, etc. In one embodiment, a compound of this invention is dosed once every seven days.

The compounds of this invention can also be dosed on a monthly basis meaning that administration is done once per month. In addition, the compounds of this invention can be dosed on a weekly basis (once a week), every other week, every three weeks or every four weeks for a single day or multiple days.

The compounds of this invention can also be dosed on an as needed or "pro re nata" "prn" schedule, and "on demand". In this type of dosing, the compounds of this invention are administered in a therapeutically effective dose at some time prior to commencement of an activity wherein the therapeutic effect of the compounds of this invention is desirable. Administration can be immediately prior to such an activity, including about 0 minutes, about 10 minutes, about 20 minutes, about 30 minutes, about 1 hour, about 2 hours, about 3 hours, about 4 hours, about 5 hours, about 6 hours, about 7 hours, about 8 hours, about 9 hours, or about 10 hours prior to such an activity, depending on the Formulation.

The compounds of this invention can be prepared by a variety of synthetic routes and techniques known to those of skill in the art. The processes disclosed herein should not be construed as limiting the examples or scope of the invention in any way but rather are provided as just some of the representative ways that the compounds of this invention can be or were prepared.

In some cases, protective groups are employed in the synthesis of the compounds of this invention and it should be appreciated that there are a diverse array of protective groups and strategies that can be employed in organic synthesis (T. W. Green and P. G. M. Wuts (2006) Greene's Protective Groups in Organic Synthesis, herein incorporated by reference in its entirety) and that where a protective group is referred to generically, any appropriate protective group should be considered.

In some instances, leaving groups are employed in the synthesis of compounds of this invention. Where a specific leaving group is referred to, it should be appreciated that other leaving groups might also be used. Leaving groups typically include those groups that can stabilize an anion. In the case of nucleophilic aromatic substitutions, the leaving group may be an anion or a neutrally charged group. In some cases, the leaving group for nucleophilic aromatic substitution may be a group that is not typically considered to be a stabilized anion (e.g. fluoride or hydride). While not intending to be bound by theory or the examples, some typical nucleophilic leaving groups include halogens, sulfonates (O-mesylates, O-tosylates, etc), hydrides, quaternized amines, nitro, and the like. Additional discussion and examples can be found in leading textbooks on organic chemistry including, for example, March's Advanced Organic Chemistry: Reactions, Mechanisms, and Structure, $5^{th}$ Edition, which is herein incorporated in its entirety.

Scheme 1 gives one embodiment of a general method for preparing compounds of this invention, such as, for example, the mono-substituted compound of Formula E, wherein X, Y, Z and $R_b$ are as defined herein and m is 1, 2 or 3. The starting material, an aryl hydrazine of Formula A, is coupled with a 1,2,cyclodione of Formula B to give the tricyclic keto compound of Formula C using standard coupling reaction conditions known to those of skill in the art. Normally, a solvent is chosen that can dissolve at least some of each of the components of the reaction. EtOH or MeOH can be a very good solvent for these reactions but other solvents such as DMSO, DMF, HMPA, etc, should be considered as well. The product C is isolated and carried to the next step. Isolation techniques are well-known to those of skill in the art and include chromatography and/or crystallization. The keto product C is converted to the alcohol F using a number of potential reagents well-known to those of skill in the art. In one embodiment the keto compound C is converted directly to the product F by reduction of the ketone, such as for example, by reaction with a Grignard reagent, $CF_3TMS$ or $CF_3CF_3TMS$. In another embodiment it might be preferable to protect the carbazole amine prior to the reduction of the ketone to form the compound of Formula D, wherein $P_1$ is any amine protecting group, known to one skilled in the art, such as, for example a trialkyl silyl groups or a tosyl group, but other protecting groups could be useful as well. The compound D is converted to the substituted alcohol E, wherein $P_2$ is any alcohol protecting group, known to one skilled in the art, such as, for example, a silyl ether, such as, trimethylsilyl group, a tert-butyldimethylsilyl ether, or a tert-butyldiphenylsilyl ether, but other protecting groups could be useful as well. Removal of the protecting groups $P_1$ and $P_2$ results in the product F.

Scheme 1

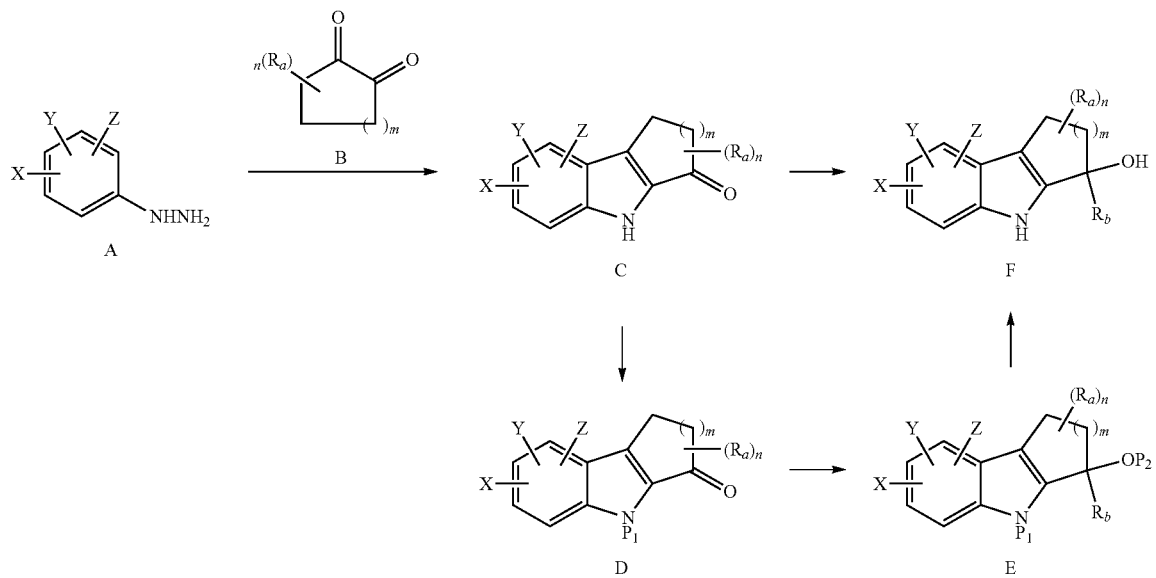

Alternatively the compound of Formula C can be prepared as shown in Scheme 2. The monosubstituted aniline compound of Formula G, wherein X, Y and Z are as defined herein and m is as defined for Scheme I, is converted in to the corresponding diazonium salt of Formula H using a number of potential reagents well-known to those of skill in the art. In one embodiment the compound G is converted to H by reaction with $NaNO_2$ in HCl at reduced temperatures. The product H is typically not isolated and converted directly to the compound of Formula C by reaction with a cyclic beta keto acid. The keto product C can then be taken onto the final product F as demonstrated previously in Scheme 1.

Scheme 2

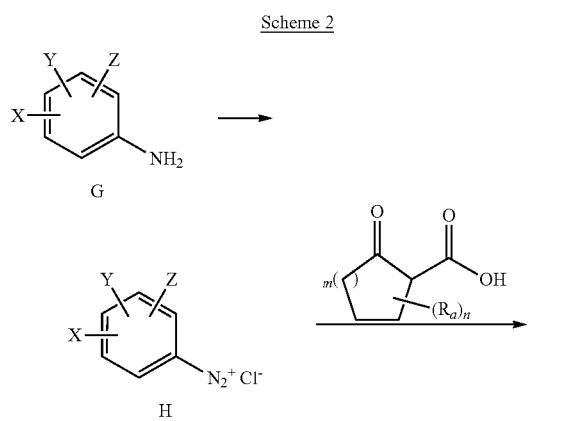

Scheme 3 shows the modification of Scheme 1 for the preparation of the di-substituted compounds of Formula L wherein X, Y, $R_b$ and m are as defined herein. The regioisomers for the keto compound of Formula K (corresponding to the compound of Formula C in Scheme 1) are separated using a number of potential methods well-known to those of skill in the art. In one embodiment the carbazole amine is converted to the t-butyl carbamate followed by chromatography. Each regioisomer is then separately converted to the compound of Formula L as described in Scheme 1

Scheme 3

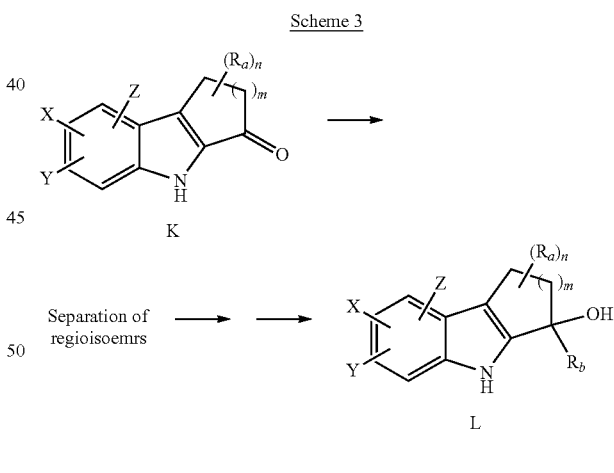

DETERMINATION OF BIOLOGICAL ACTIVITY

In order to demonstrate the utility of the compounds of this invention, an androgen receptor binding assay was performed wherein many of the compounds of this invention are shown to demonstrate significant affinity for the androgen receptor. The assay was performed as specified by the manufacturer (Invitrogen, Madison, Wis.). Briefly, 1 μl of 10 mM compound was added to 500 μl of AR screening buffer in a 1.5 ml eppendorf tube to make a $2 \times 10^{-5}$ M stock. 10-fold serial dilutions of the test compounds were prepared ranging in concentration from $10^{-5}$ M to $10^{-12}$ M. Each dilution was added in triplicate to a black 384-microtiter plate. The test compounds will be diluted 2-fold in the final reaction. 2×AR-Fluormone™ complex was prepared with 2 nM Flourmone AL Green™ and 30 nM AR. 25 µl of 2× complex was aliquoted to each reaction well, such that the final reaction volume was 50 µl per well. The plate was sealed with a foil cover and incubated in the dark at room temperature for 4 h. Polarization values for each well were measured. The polarization values were plotted against the concentration of the test compound. The concentration of the test compound that results in half-maximum shift equals the $IC_{50}$ of the test compound. As a control, a competition curve for R1881 (methyltrienolone) was performed for each assay. Curve Fitting was performed using GraphPad Prism® software from GraphPad™ Software Inc. Binding data are reported as a single determination if the experiment was run once only and as the average of experiments if the binding experiment was performed two or more times with that compound. Results are set forth in Table 1.

COMPOUND CHARACTERIZATION

All solvents were commercially available and used without further purification. Reactions were monitored by thin-layer chromatography (TLC) on silica gel plates (60 $F_{254}$; MERCK) which were visualized using ultraviolet light, iodine vapor, or ninhydrin stain. Column chromatography was performed on silica gel (60-120 mesh, ACME Synthetic Chemicals, Mumbai) using commercially available high purity solvents. $^1$H and $^{13}$C NMR spectra were typically determined in CDCl$_3$ or DMSO-d$_6$, using either a Varian Inova 500 MHz spectrometer or a Varian Gemini 2000 200 MHz spectrometer. Proton chemical shifts (δ) are relative to the residual solvent peaks for each deuterated solvent and expressed in ppm. Coupling constants (J) are expressed in hertz. Infra red spectra were obtained in Jasco 460 plus using KBr pellets. Mass Spectra was recorded in ESI & APCI source using AGILENT 6310 Iontrap or Shimadzu LCMS-2010 EV. Chemical reagents were generally commercially available and were used without further purification unless stated otherwise. Chemical reagents were generally commercially available and were used without further purification unless stated otherwise.

Example 1

6,7-Dichloro-1-methyl-2,3,4,9-tetrahydro-1H-carbazol-1-ol

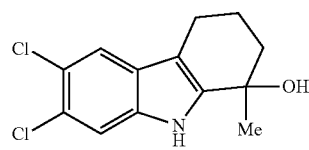 [SMILES: CC1(O)CCCc2c1[nH]c1cc(Cl)c(Cl)cc21]

Intermediate 1a 6,7-Dichloro-2,3,4,9-tetrahydro-1H-carbazol-1-one and 5,6-dichloro-2,3,4,9-tetrahydro-1H-carbazol-1-one

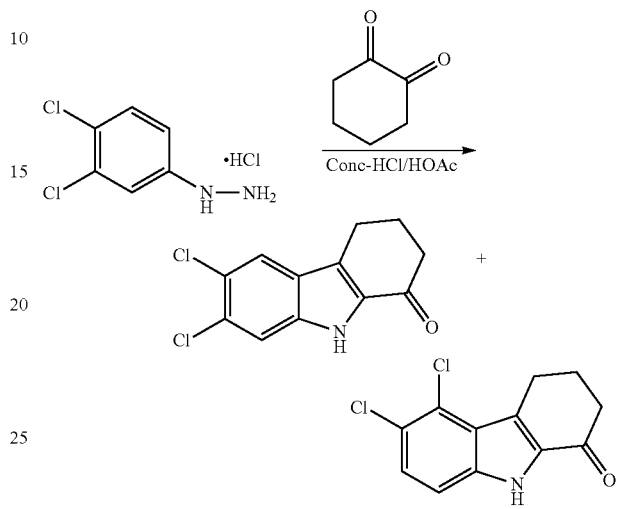

To a solution of (3,4-dichlorophenyl)hydrazine hydrochloride (2 g, 9.3 mmol) in EtOH (20 mL), heated to 60° C., was added cyclohexane-1,2-dione (1.1 g, 9.8 mmol) in AcOH (21 mL) and conc. HCl (9 mL). The reaction mixture was stirred at 60° C. for 16 h, then neutralized with saturated NaHCO$_3$ (20 mL) and extracted with EtOAc (2×20 mL). The combined organic extracts were dried over Na$_2$SO$_4$ and concentrated under reduced pressure to give the crude title compound (1.2 g, 60%, mixture of regioisomers) which was passed through a short silica column [EtOAc-hexane (1:9) as eluant] and used directly in the next step.

Intermediate 1b tert-Butyl 6,7-dichloro-1-oxo-3,4-dihydro-1H-carbazole-9(2H)-carboxylate and tert-butyl 5,6-dichloro-1-oxo-3,4 dihydro-1H-carbazole-9(2H)-carboxylate

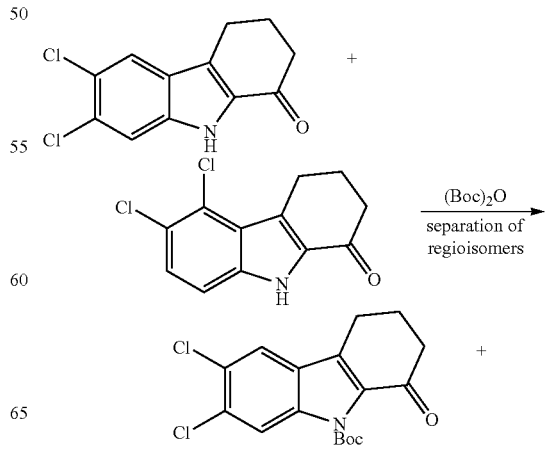

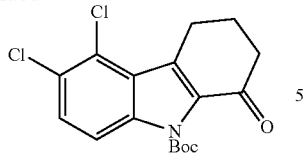

The mixture of 6,7-dichloro-2,3,4,9-tetrahydro-1H-carbazol-1-one and 5,6-dichloro-2,3,4,9-tetrahydro-1H-carbazol-1-one (7.5 g, 29.7 mmol) was dissolved in THF (130 mL), cooled to 0° C., and DMAP (5.4 g, 44.2 mmol) followed by Boc anhydride (7.7 g, 35.3 mmol) were added. After 1 h at 0° C., the volatiles were removed under reduced pressure and the crude residue was diluted with water (50 mL) and extracted with EtOAc (3×30 mL). The combined organic extracts were concentrated under reduced pressure to give the crude compound which was purified by chromatography using EtOAc-hexane (1:49) as eluant to give tert-butyl 5,6-dichloro-1-oxo-3,4 dihydro-1H-carbazole-9(2H)-carboxylate (2 g) and EtOAc-hexane (1:19) as eluant to give tert-butyl 6,7-dichloro-1-oxo-3,4-dihydro-1H-carbazole-9(2H)-carboxylate (1.7 g) both as white solids. $^1$H NMR (500 MHz, CDCl$_3$, δ in ppm) (tert-butyl 5,6-dichloro-1-oxo-3,4 dihydro-1H-carbazole-9(2H)-carboxylate) 7.91 (d, J=8.5 Hz, 1H), 7.48 (d, J=9.5 Hz, 1H), 3.34 (t, J=5.5 Hz, 2H), 2.66 (t, J=6.5 Hz, 2H), 2.27-2.22 (m, 2H), 1.62 (s, 9H). $^1$H NMR (500 MHz, CDCl$_3$, δ in ppm) (tert-butyl 6,7-dichloro-1-oxo-3,4-dihydro-1H-carbazole-9(2H)-carboxylate) 8.24 (s, 1H), 7.68 (s, 1H), 2.93 (t, J=7.0 Hz, 2H), 2.69 (t, J=7.0 Hz, 2H), 2.27-2.25 (m, 2H), 1.63 (s, 9H).

Intermediate 1c 6,7-Dichloro-2,3,4,9-tetrahydro-1H-carbazol-1-one

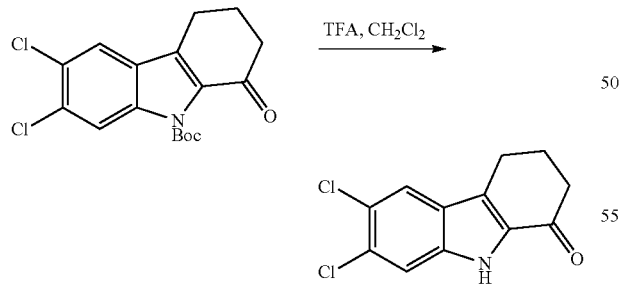

To a solution of tert-butyl 6,7-dichloro-1-oxo-3,4-dihydro-1H-carbazole-9(2H)-carboxylate (1.4 g, 3.9 mmol) in DCM (20 mL), cooled to 0° C., was added TFA (2 mL). The reaction mixture was stirred at 0° C. for 1 h, neutralized with saturated NaHCO$_3$ (15 mL) and extracted with DCM (2×15 mL). The combined organic extracts were dried over Na$_2$SO$_4$ and concentrated under reduced pressure to afford the title compound as a white solid (850 mg, 85%). $^1$H NMR (500 MHz, CDCl$_3$, δ in ppm) 8.87 (bs, 1H), 7.75 (s, 1H), 7.55 (s, 1H), 2.98 (t, J=6.0 Hz, 2H), 2.68 (t, J=6.0 Hz, 2H), 2.30-2.25 (m, 2H).

Example 1

6,7-Dichloro-1-methyl-2,3,4,9-tetrahydro-1H-carbazol-1-ol

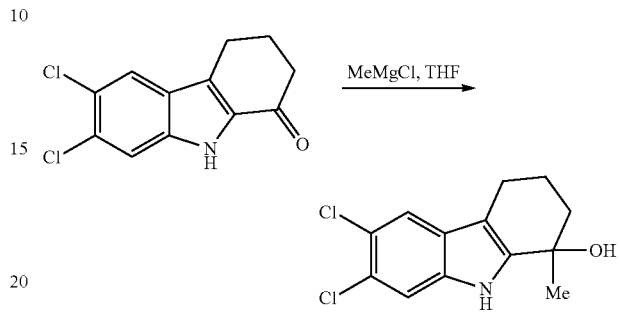

To a solution of 6,7-dichloro-2,3,4,9-tetrahydro-1H-carbazol-1-one (0.1 g, 0.4 mmol) in anhydrous THF (5 mL) cooled to 0° C., MeMgCl (1.3 mL, 3.95 mmol, 3M in THF) was added dropwise. The reaction mixture was slowly warmed to room temperature and stirred for 5 h, cooled to 0° C., and then quenched with saturated NH$_4$Cl (10 mL) and extracted with EtOAc (3×20 mL). The combined organic extracts were dried over Na$_2$SO$_4$ and the solvent was removed under reduced pressure to give the crude material which was purified by column chromatography [EtOAc-hexane (1:9) as eluant] to give the title compound as a pale brown solid (0.01 g, 10%). $^1$H NMR (500 MHz. DMSO-d$_6$, δ in ppm) 7.75 (s, 1H), 7.60 (s, 1H), 5.96 (s, 1H), 5.15 (s, 1H), 2.19-2.17 (m, 1H), 2.0-1.82 (m, 2H), 1.62-1.59 (m, 1H), 1.45 (s, 3H), 1.43-1.41 (m, 1H), 0.98-1.11 (m, 1H).

Example 2

1-Hydroxy-1-methyl-2,3,4,9-tetrahydro-1H-carbazole-6-carbonitrile

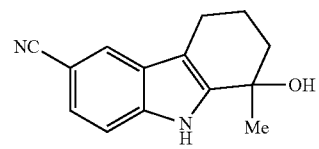 [SMILES: CC1(O)CCCc2c1[nH]c1ccc(C#N)cc21]

Intermediate 2a

1-Oxo-2,3,4,9-tetrahydro-1H-carbazole-6-carbonitrile

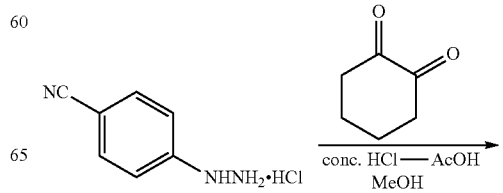

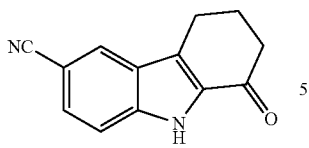

4-Hydrazinylbenzonitrile hydrochloride (3 g, 17.6 mmol) dissolved in MeOH (30 mL), was heated to 60° C., and 1,2-cyclo hexadione (1.98 g, 17.6 mmol) in AcOH (30 mL) and HCl (12 mL) were added while maintaining the temperature at 60° C. The reaction mixture was stirred at 60° C. for 12 h and then cooled to room temperature. The volatiles were removed in vacuo and the residue was diluted with water, neutralized with saturated NaHCO₃ solution and extracted with EtOAc (2×40 mL). The combined organic extracts were concentrated under reduced pressure to give the crude product which was purified by silica gel chromatography [EtOAc-hexane (1:3) as eluant] to provide the title compound (3.3 g, 89%). $^1$H NMR (200 MHz, CDCl₃, δ in ppm) 8.80 (bs, 1H), 7.80 (d, J=2.0 Hz, 1H), 7.45 (dd, J=12.0, 2.0 Hz, 1H), 7.30 (d, J=12.5 Hz, 1H), 2.90 (t, J=9.0 Hz, 2H), 2.62 (t, J=9.0 Hz, 2H), 2.25 (m, 2H).

Example 2

1-Hydroxy-1-methyl-2,3,4,9-tetrahydro-1H-carbazole-6-carbonitrile

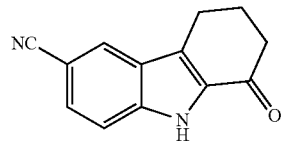

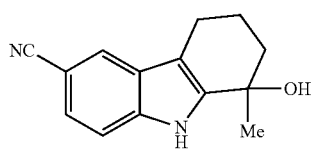

1-Oxo-2,3,4,9-tetrahydro-1H-carbazole-6-carbonitrile (0.12 g, 0.57 mmol) was dissolved in anhydrous THF (5 mL), cooled to 0° C., and methyl magnesium chloride (0.12 g, 1.71 mmol, 3M in THF) was added dropwise. The reaction mixture was warmed to room temperature and stirred for 3 h at room temperature then cooled to 0° C., saturated NH₄Cl (10 mL) was added and then extracted with EtOAc (4×25 mL). The combined organic extracts were dried over Na₂SO₄ concentrated under reduced pressure to give the crude material which was purified by column chromatography [EtOAc-hexane (3:7) as eluant] to obtain the title compound (0.03 g, 23%). $^1$H NMR (500 MHz, DMSO-d₆, δ in ppm) 11.4 (s, 1H), 7.9 (s, 1H), 7.42 (d, J=12.0 Hz, 1H), 7.39 (d, J=12.0 Hz, 1H), 5.0 (s, 1H), 2.64-2.61 (m, 2H), 2.0-1.7 (m, 4H), 1.4 (s, 3H). IR cm$^{-1}$ 2216 (CN).

Example 3

6,7-Dichloro-1-(trifluoromethyl)-2,3,4,9-tetrahydro-1H-carbazol-1-ol

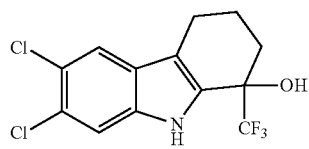 [SMILES: OC1(C(F)(F)F)CCCc2c1[nH]c1cc(Cl)c(Cl)cc21]

Intermediate 3a 6,7-Dichloro-9-tosyl-2,3,4,9-tetrahydro-1H-carbazol-1-one

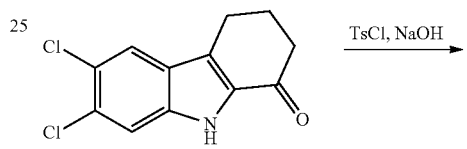

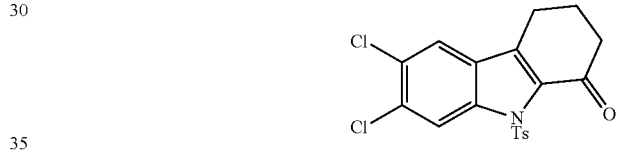

6,7-Dichloro-2,3,4,9-tetrahydro-1H-carbazol-1-one (intermediate 1c) (600 mg, 2.3 mmol) in DCM (30 mL), was cooled to 0° C., then 5N NaOH (2 mL) followed by a catalytic amount of benzene triethyl ammonium chloride and p-TSCl (1.8 g, 9.4 mmol) were added. The reaction mixture was stirred at room temperature for 6 h, diluted with water (30 mL) and then extracted with EtOAc (4×50 mL). The combined organic extracts were dried over Na₂SO₄ and concentrated under reduced pressure to provide the crude material which was purified by column chromatography [EtOAc-hexane (3:17)] to afford the title compound (500 mg, 52%). $^1$H NMR (200 MHz, CDCl₃, δ in ppm) 8.54 (s, 1H), 8.03 (d, J=8.4 Hz, 2H), 7.71 (s, 1H), 7.35 (d, J=8.0 Hz, 2H), 2.93 (t, J=5.8 Hz, 2H), 2.64 (t, J=6.0 Hz, 2H), 2.42 (s, 3H), 2.21-2.15 (m, 2H).

Intermediate 3b 6,7-Dichloro-9-tosyl-1-(trifluoromethyl)-1-(trimethylsilyloxy)-2,3,4,9-tetrahydro-1H-carbazole

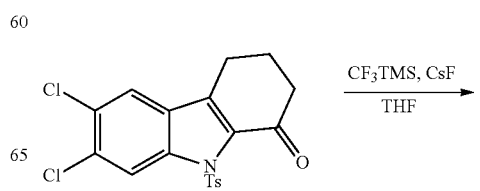

-continued

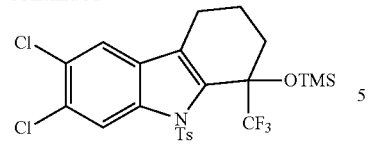

To a solution of 6,7-dichloro-9-tosyl-2,3,4,9-tetrahydro-1H-carbazol-1-one (0.3 g, 0.73 mmol) in anhydrous THF (10 mL), cooled to 0° C., CF$_3$TMS (1.16 mL, 7.4 mmol) and CsF (0.05 g, 0.37 mmol) were added. The reaction mixture was slowly warmed to room temperature, stirred for 30 min. and then quenched with saturated aqueous NH$_4$Cl (10 mL) and extracted with EtOAc (3×30 mL). The combined organic extracts were dried over Na$_2$SO$_4$ and concentrated in vacuo to obtain the crude compound which was quickly passed through a short pad of silica gel [EtOAc-hexanes (1:49) as eluant] to give the title compound (390 mg, 56%) that was used immediately in the next step without any spectroscopic analysis.

Example 3

6,7-Dichloro-1-(trifluoromethyl)-2,3,4,9-tetrahydro-1H-carbazol-1-ol

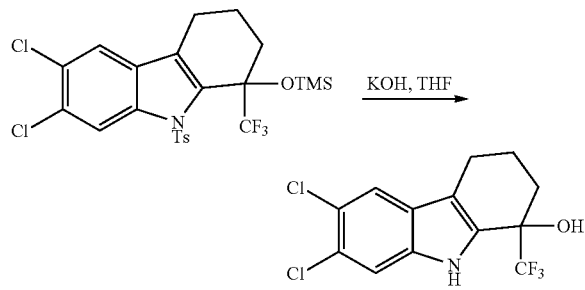

6,7-Dichloro-9-tosyl-1-(trifluoromethyl)-1-(trimethylsilyloxy)-2,3,4,9-tetrahydro-1H-carbazole (220 mg, 0.41 mmol) was dissolved in anhydrous THF-EtOH (10 mL, 1:1). KOH (117 mg, 2.06 mmol) in H$_2$O (7 mL) was added and then stirred at room temperature for 30 min. and then at 55° C. for 20 h. The reaction mixture was diluted with water (30 mL) and extracted with EtOAc (3×20 mL). The combined organic extracts were dried over Na$_2$SO$_4$ and the solvent was removed under reduced pressure to provide the crude compound which was purified by column chromatography [EtOAc-hexane (1:9) as eluant] to afford the title compound as a white solid (130 mg, 76%). $^1$H NMR (500 MHz. DMSO-d$_6$, δ in ppm) 8.17 (bs, 1H), 7.61 (s, 1H), 7.48 (s, 1H), 2.82-2.78 (m, 1H), 2.70-2.64 (m, 1H), 2.42 (s, 1H), 2.28-2.20 (m, 1H), 2.12-2.01 (m, 3H).

Example 4

1-Hydroxy-1-(trifluoromethyl)-2,3,4,9-tetrahydro-1H-carbazole-6-carbonitrile

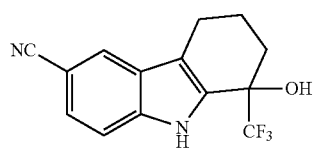 [SMILES: N#Cc1ccc2[nH]c3c(c2c1)CCCC3(O)C(F)(F)F]

Intermediate 4a

1-Oxo-9-tosyl-2,3,4,9-tetrahydro-1H-carbazole-6-carbonitrile

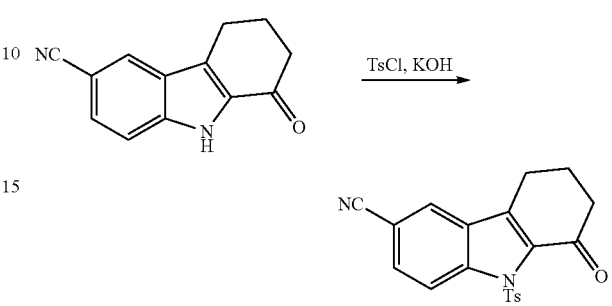

To a solution of 1-oxo-2,3,4,9-tetrahydro-1H-carbazole-6-carbonitrile (intermediate 2a) (0.20 g, 0.95 mmol) in THF (2.0 mL), KOH (0.27 g, 4.8 mmol) in water was added followed by TsCl (0.27 g, 1.4 mmol). The reaction mixture was stirred at room temperature for 12 h and then extracted with EtOAc (3×15 mL). The combined organic extracts were dried over Na$_2$SO$_4$ and concentrated in vacuo to give the crude compound which was purified by column chromatography [EtOAc-hexane (1:4) as eluant] to obtain the title compound as an off-white solid (0.23 g, 65%). $^1$H NMR (200 MHz, CDCl$_3$, δ in ppm) 8.0 (d, J=8.4 Hz, 2H), 7.82 (d, J=2.0 Hz, 1H), 7.43 (dd, J=12.0, 2.0 Hz, 1H), 7.39 (d, J=8.4 Hz, 2H), 7.30 (d, J=12.5 Hz, 1H), 2.95 (t, J=9.0 Hz, 2H), 2.66 (t, J=9.0 Hz, 2H), 2.40 (s, 3H), 2.30 (m, 2H).

Intermediate 4b

9-Tosyl-1-(trifluoromethyl)-1-(trimethylsilyloxy)-2,3,4,9-tetrahydro-1H-carbazole-6-carbonitrile

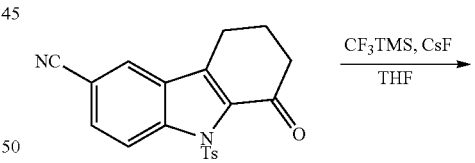

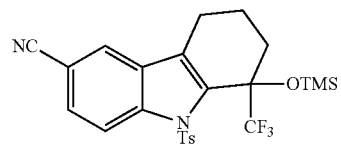

1-Oxo-9-tosyl-2,3,4,9-tetrahydro-1H-carbazole-6-carbonitrile (0.2 g, 0.5 mmol) was dissolved in anhydrous THF (5 mL), cooled to 0° C. and CF$_3$TMS (0.87 mL, 5.5 mmol) followed by CsF (0.41 g, 0.2 mmol) were added. The reaction mixture was stirred at 0° C. for 10 min., quenched with saturated NH$_4$Cl (10 mL) and extracted with EtOAc (3×20 mL). The combined organic extracts were dried over Na$_2$SO$_4$ concentrated in vacuo to afford the crude title compound as a white solid (250 mg, 92%) which was used directly in the next step.

Example 4

1-Hydroxy-1-(trifluoromethyl)-2,3,4,9-tetrahydro-1H-carbazole-6-carbonitrile

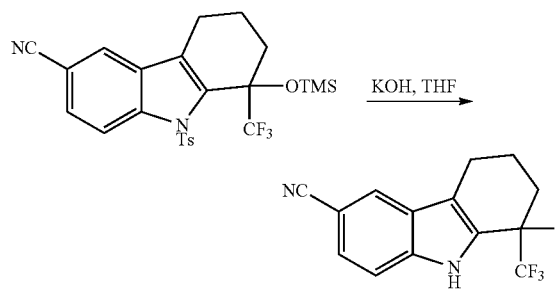

9-Tosyl-1-(trifluoromethyl)-1-(trimethylsilyloxy)-2,3,4,9-tetrahydro-1H-carbazole-6-carbonitrile (0.03 g, 0.06 mmol) was dissolved in THF (2 mL) and KOH (11 mg, 0.2 mmol), in H$_2$O (2 mL) was added. The reaction mixture was heated to 55° C. for 24 h, then cooled to room temperature, diluted with water (5 mL) and extracted with EtOAc (3×5 mL). The combined organic extracts were dried over Na$_2$SO$_4$ and concentrated under reduced pressure to give the crude compound which was purified by column chromatography [EtOAc-hexane (1:9) as eluant] to afford the title compound as a white solid (15 mg, 79%). $^1$H NMR (500 MHz, CDCl$_3$, δ in ppm) 8.4 (bs, 1H), 7.9 (s, 1H), 7.49 (d, J=9.0 Hz, 1H), 7.44 (d, J=8.0 Hz, 1H), 2.89-2.85 (m, 1H), 2.76-2.74 (m, 1H), 2.45 (s, 1H), 2.32-2.28 (m, 1H), 2.14-2.12 (m, 2H), 2.05-2.03 (m, 1H).

Example 5

5,6-Dichloro-1(trifluoromethyl)-2,3,4,9-tetrahydro-1H-carbazol-1ol

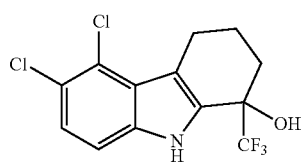 [SMILES: OC1(C(F)(F)F)CCCc2c1[nH]c1ccc(Cl)c(Cl)c21]

Intermediate 5a 5,6-Dichloro-2,3,4,9-tetrahydro-1H-carbazol-1-one

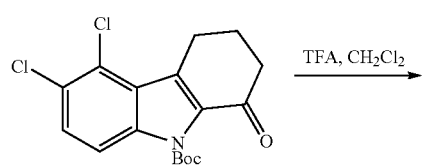

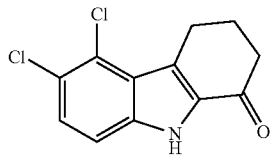

tert-Butyl 5,6-dichloro-1-oxo-3,4-dihydro-1H-carbazole-9(2H)-carboxylate (intermediate 1b) (0.9 g, 2.5 mmol) was dissolved in DCM (15 mL), cooled to 0° C., and TFA (1.6 mL) was added. The reaction mixture was stirred at 0° C. for 1 h, neutralized with saturated NaHCO$_3$ (20 mL) and extracted with DCM (2×20 mL). The combined organic extracts were dried over Na$_2$SO$_4$ and concentrated in vacuo to give the title compound as a white solid (450 mg, 70%) which was directly in the next step without further purification. $^1$H NMR (500 MHz, CDCl$_3$, δ in ppm) 9.18 (bs, 1H), 7.38 (d, J=9.0 Hz, 1H), 7.28 (d, J=9.5 Hz, 1H), 3.37 (t, J=6.0 Hz, 2H), 2.67 (t, J=7.0 Hz, 2H), 2.30-2.25 (m, 2H).

Intermediate 5b 5,6-Dichloro-9-tosyl-2,3,4,9-tetrahydro-1H-carbazol-1-one

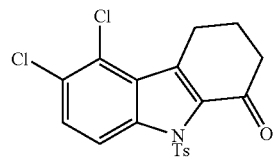

To a solution of 5,6-dichloro-2,3,4,9-tetrahydro-1H-carbazol-1-one (600 mg, 2.3 mmol) in DCM (10 mL), cooled to 0° C., 5N NaOH (5 mL) followed by a catalytic amount of benzene triethyl ammonium chloride and p-TSCl (1.8 g, 9.4 mmol) were added. The reaction mixture was slowly warmed to room temperature, stirred for 4 h, then quenched with NH$_4$Cl and extracted with EtOAc (2×100 mL). The combined organic extracts were dried over Na$_2$SO$_4$ and concentrated under reduced pressure to obtain the crude material which was purified by column chromatography [EtOAc-hexane (3:17) as eluant] to afford the title compound (800 mg, 88%). $^1$H NMR (200 MHz, CDCl$_3$, δ in ppm) 8.54 (s, 1H), 8.03 (d, J=8.4 Hz, 2H), 7.71 (s, 1H), 7.35 (d, J=8.0 Hz, 2H), 2.93 (t, J=5.8 Hz, 2H), 2.64 (t, J=6.0 Hz, 2H), 2.42 (s, 3H), 2.21-2.15 (m, 2H).

Intermediate 5c 5,6-Dichloro-9-tosyl-1(trifluoromethyl)-1-(trimethylsilyloxy)-2,3,4,9-tetrahydro-1H-carbazol

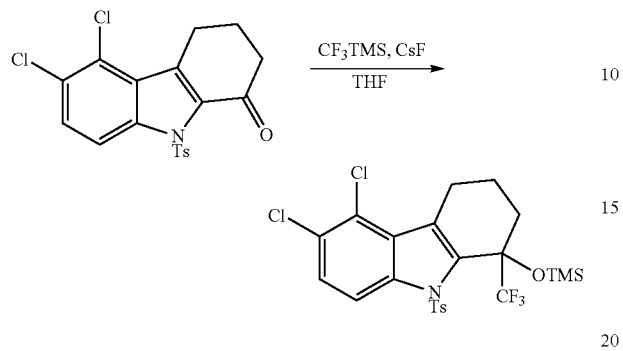

5,6-Dichloro-9-tosyl-2,3,4,9-tetrahydro-1H-carbazol-1-one (0.1 g, 0.24 mmol) was dissolved in dry THF (10 mL), cooled to 0° C. and CsF (0.037 g, 0.24 mmol) followed by CF$_3$TMS (0.39 mL, 2.45 mmol) was added dropwise. The resulting mixture was stirred at 0° C. for 1 h, then quenched with saturated NH$_4$Cl (20 mL) and extracted with EtOAc (2×25 mL). The combined organic extracts were dried over Na$_2$SO$_4$, concentrated in vacuo to obtain the crude product which was purified by column chromatography [EtOAc-hexane (1:19) as eluant] to give the title compound (0.110 g, 82%). $^1$H NMR (500 MHz, CDCl$_3$, δ in ppm) 8.08-8.06 (d, J=9.5 Hz, 1H), 7.52-7.50 (d, J=8.0 Hz, 2H), 7.34-7.32 (d, J=9.5 Hz, 1H), 7.06-7.04 (d, J=8.0 Hz, 2H) 3.11-3.07 (m, 1H), 2.97-2.90 (m, 1H), 2.29 (s, 3H), 2.26 (bs, 1H), 2.03-1.98 (m, 2H), 1.94-1.92 (m, 1H), 0.30 (s, 9H).

Example 5

5,6-Dichloro-1(trifluoromethyl)-2,3,4,9-tetrahydro-1H-carbazol-1ol

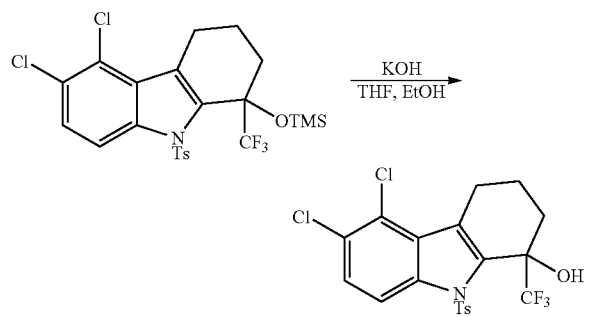

To a solution of 5,6-dichloro-9-tosyl-1(trifluoromethyl)-1-(trimethylsilyloxy)-2,3,4,9-tetrahydro-H-carbazole (0.110 g, 0.2 mmol) in a mixture of THF (10 mL) and EtOH (2 mL), KOH (0.125 g, 2.2 mmol) dissolved in water (2 mL) was added. The reaction mixture was stirred at room temperature for 1 h and then for an additional 3 h at 60° C. The reaction mixture was diluted with water (20 mL) and extracted with EtOAc (2×25 mL). The combined organic extracts were dried over Na$_2$SO$_4$ and concentrated under reduced pressure. The crude product was purified by column chromatography [EtOAc-hexane (1:9) as eluant] to afford the title compound as a white solid (0.040 g, 62%) (HPLC 99.6%). $^1$H NMR (500 MHz, CDCl$_3$, δ in ppm) 8.30 (bs, 1H), 7.27-7.26 (d, J=8.5 Hz, 1H), 7.20-7.18 (d, J=8.5 Hz, 1H), 3.32-3.27 (m, 1H), 3.04-2.97 (m, 1H), 2.42 (s, 1H), 2.27-2.2 (m, 1H), 2.09-2.06 (m, 2H), 2.02-1.98 (m, 1H).

Example 6

6,7-Dichloro-1-(perfluoroethyl)-2,3,4,9-tetrahydro-1H-carbazol-1-ol

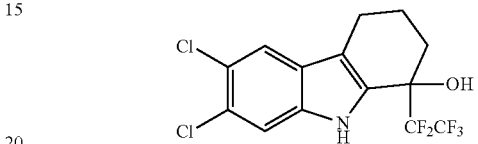

Intermediate 6a 6,7-Dichloro-1-(perfluoroethyl)-9-tosyl-1-(trimethylsilyloxy)-2,3,4,9-tetrahydro-1H-carbazole

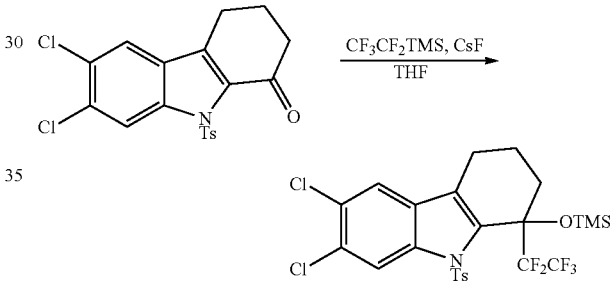

To a solution of 6,7-dichloro-9-tosyl-2,3,4,9-tetrahydro-1H-carbazol-1-one (intermediate 3a) (0.05 g, 0.12 mmol) in anhydrous THF (3 mL), cooled to 0° C., CsF (9 mg, 0.06 mmol) and (pentafluoro ethyl)trimethyl silane (0.25 g, 1.30 mmol) were added. The reaction mixture was stirred at 0° C. for 15 min., quenched with saturated NH$_4$Cl and extracted with EtOAc (2×20 mL). The combined organic extracts were dried over Na$_2$SO$_4$ and concentrated in vacuo to provide the residue which was quickly passed through a short pad of silica [EtOAc-hexane (1:9) as eluant] to give the title compound as a light yellow solid (0.06 g, 81%), which was used immediately in the next step without any spectroscopic analysis.

Example 6

6,7-Dichloro-(perfluoroethyl)-2,3,4,9-tetrahydro-1H-carbazol-1-ol

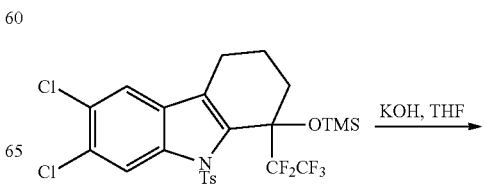

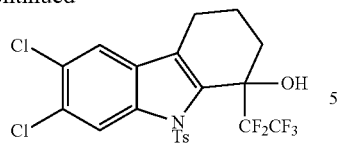

To 6,7-Dichloro-1-(perfluoroethyl)-9-tosyl-1-(trimethylsilyloxy)-2,3,4,9-tetrahydro-1H-carbazole (0.25 g, 0.47 mmol) in THF (5 mL) was added 6N KOH (6 mL). The reaction mixture was stirred at room temperature for 10 min. and then refluxed for 36 h, diluted with water and extracted with EtOAc (3×20 mL). The combined organic extracts were dried over $Na_2SO_4$ and concentrated under reduced pressure to give the crude product which was purified by silica gel chromatography [EtOAc-hexane (3:22) as eluant] to give the title compound as a white solid (0.06 g, 34%). $^1$H NMR (500 MHz, $CDCl_3$, δ in ppm) 8.21 (bs, 1H), 7.62 (s, 1H), 7.49 (s, 1H), 2.82-2.80 (m, 1H), 2.68-2.62 (m, 1H), 2.45 (s, 1H), 2.28-2.23 (m, 1H), 2.18-2.15 (m, 1H), 2.12-2.06 (m 1H), 2.03-2.0 (m, 1H).

Example 7

1-Hydroxy-1-(perfluoroethyl)-2,3,4,9-tetrahydro-1H-carbazole-6-carbonitrile

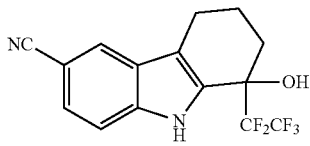

Intermediate 7a 1-(Perfluoroethyl)-9-tosyl-1-(trimethylsilyloxy)-2,3,4,9-tetrahydro-1H-carbazole-6-carbonitrile

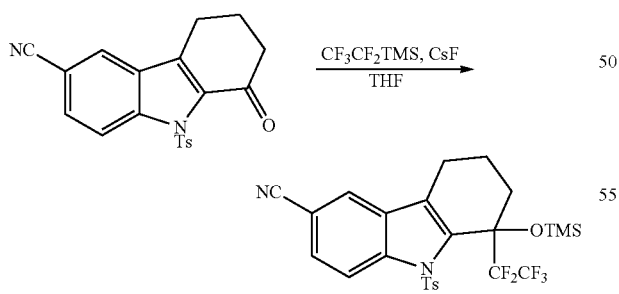

To 1-oxo-9-tosyl-2,3,4,9-tetrahydro-1H-carbazole-6-carbonitrile (intermediate 2a) (0.2 g, 0.5 mmol) in anhydrous THF (10 mL), cooled to 0° C., $CF_3CF_2TMS$ (1.05 g, 5.5 mmol) followed by CsF (0.04 g, 0.2 mmol) were added. The reaction mixture was stirred at 0° C. for 30 min., then quenched with saturated $NH_4Cl$ (10 mL) and extracted with EtOAc (3×10 mL). The combined organic extracts were dried over $Na_2SO_4$, concentrated in vacuo to obtain the crude compound (180 mg) which was used immediately in the next step without further purification.

Example 7

1-Hydroxy-1-(perfluoroethyl)-2,3,4,9-tetrahydro-1H-carbazole-6-carbonitrile

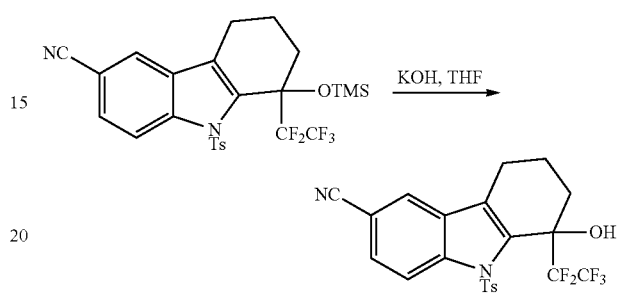

To a solution of 1-(perfluoroethyl)-9-tosyl-1-(trimethylsilyloxy)-2,3,4,9-tetrahydro-1H-carbazole-6-carbonitrile (180 mg, 0.3 mmol) in THF (5 mL), KOH (90 mg, 1.6 mmol) in $H_2O$ (1 mL) was added. The reaction mixture was refluxed for 20 h, diluted with water and extracted with EtOAc (3×20 mL). The combined organic extracts were dried over $Na_2SO_4$ and concentrated under reduced pressure to give the crude residue which was purified by column chromatography [EtOAc-hexane (1:19) as eluant] to afford the title compound as a white solid (40 mg, 40%). $^1$H NMR (500 MHz, $CDCl_3$, δ in ppm) 8.5 (bs, 1H), 7.9 (s, 1H), 7.49 (d, J=7.5 Hz, 1H), 7.44 (d, J=7.5 Hz, 1H), 2.90-2.86 (m, 1H), 2.74-2.56 (m, 1H), 2.56 (s, 1H), 2.33-2.29 (m, 1H), 2.20-2.12 (m, 2H), 2.04-2.03 (m, 1H).

Example 8

6,8-Dichloro-1-(trifluoromethyl)-2,3,4,9-tetrahydro-1H-carbazol-1-ol

Intermediate 8a 6,8-Dichloro-2,3,4,9-tetrahydro-1H-carbazol-1-one

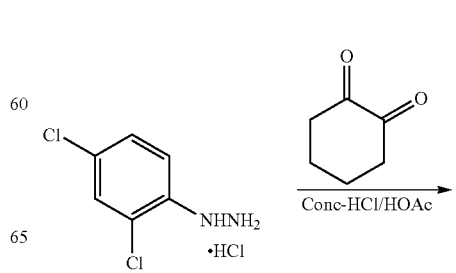

37

-continued

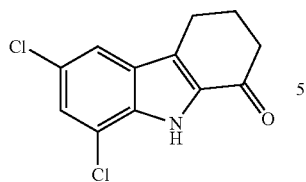

To a solution of 2,4-Dichlorophenyl)hydrazine (4 g, 18.7 mmol) in MeOH (40 mL) at 60° C., was added cyclohexane-1,2-dione (2 g, 18.7 mmol) in AcOH (56 mL) and HCl (18 mL) while maintaining the temperature at 60° C. The reaction mixture was stirred for 18 h at 60° C. then allowed to cool to room temperature. MeOH was removed in vacuo and the reaction mixture basified with saturated NaHCO$_3$ (pH-8) and extracted with EtOAc (3×100 mL). The combined organic extracts were dried over Na$_2$SO$_4$ and concentrated under reduced pressure to give the crude product which was purified by silica gel chromatograph [EtOAc-hexane (3:17) as eluant] to provide the title compound (0.6 g, 13%). $^1$H NMR (200 MHz, CDCl$_3$, δ in ppm) 8.86 (bs, 1H), 7.56 (d, J=1.8 Hz, 1H), 7.37 (d, J=1.6 Hz, 1H), 2.99 (t, J=6.0 Hz, 2H), 2.71 (dd, J=7.6, 6.0 Hz, 2H), 2.34-2.22 (m, 2H).

Intermediate 8b 6,8-Dichloro-1-(trifluoromethyl)-1-(trimethylsilyloxy)-2,3,4,9-tetrahydro-1H-carbazole

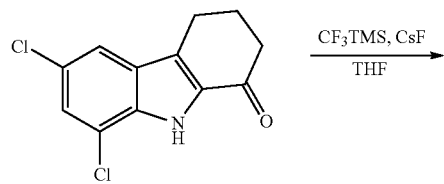

To a solution of 6,8-dichloro-9-tosyl-2,3,4,9-tetrahydro-1H-carbazol-1-one (0.3 g, 1.1 mmol) in anhydrous THF (10 mL), cooled to 0° C., CF$_3$TMS (1.87 mL, 11.8 mmol) and CsF (0.36 g, 2.3 mmol) were added. The reaction mixture was stirred at 0° C. for 45 min. and then quenched with saturated NH$_4$Cl (20 mL) and extracted with EtOAc (3×50 mL). The combined organic extracts were dried over Na$_2$SO$_4$ and the solvent removed under reduced pressure to provide the crude compound which was passed through a short silica pad [EtOAc-hexane (1:19) as eluant] to give the title compound (400 mg) that was immediately in the next step without any characterization.

38

Example 8

6,8-Dichloro-1-(trifluoromethyl)-2,3,4,9-tetrahydro-1H-carbazol-1-ol

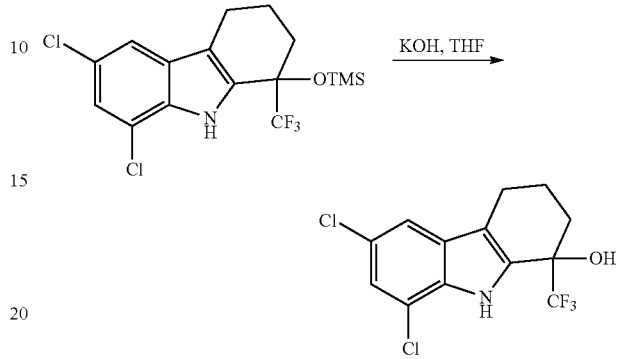

6,8-Dichloro-1-(trifluoromethyl)-1-(trimethylsilyloxy)-2,3,4,9-tetrahydro-1H-carbazole (0.4 g, 1.0 mmol) was dissolved in THF (5 mL) and KOH (280 mg, 5.0 mmol) in H$_2$O (5 mL), was added. The resulting mixture stirred at room temperature for 2 h, diluted with water (20 mL) and extracted with EtOAc (3×20 mL). The combined organic extracts were then dried over Na$_2$SO$_4$ and concentrated under reduced pressure to give the crude residue which was purified by column chromatography [EtOAc-hexane (1:19) as eluant] to provide the title compound as a white solid (100 mg, 26%). $^1$H NMR (500 MHz, DMSO-d$_6$, δ in ppm) 11.03 (s, 1H), 7.57 (d, J=1.5 Hz, 1H), 7.32 (d, J=1.5 Hz, 1H), 6.6 (s, 1H), 2.72-2.64 (m, 2H), 2.23-2.19 (m, 1H), 2.0-1.9 (m, 3H).

Example 9

(S)-6,7-Dichloro-1-(trifluoromethyl)-2,3,4,9-tetrahydro-1H-carbazol-1-ol and (R)-6,7-dichloro-1-(trifluoromethyl)-2,3,4,9-tetrahydro-1H-carbazol-1-ol

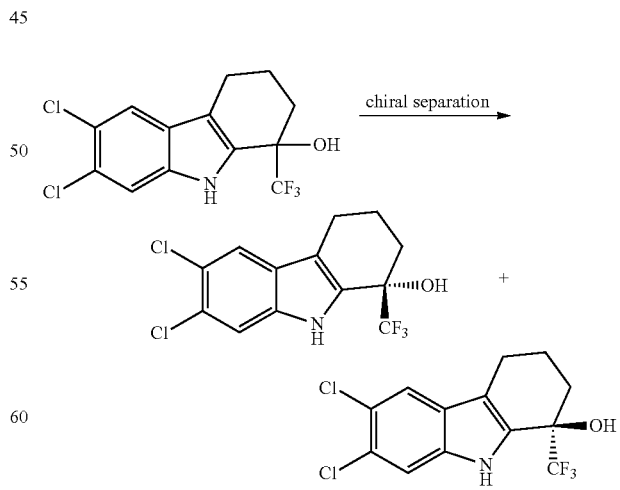

A racemic mixture of 6,7-dichloro-1-(trifluoromethyl)-2,3,4,9-tetrahydro-1H-carbazol-1-ol (Example 3) was separated by chiral HPLC using the following conditions:

Chiral HPLC Method:
Chiral column: Chiralpak AD-H, 250×4.6 mm, 5μ
Mobile phase A: 0.1% TFA n-Hexane
Mobile phase B: Ethanol
Isocratic A:B (70:30)
Flow rate: 1.00 mL/min.
Detection: λ 225 nm The retention times for the two chiral isomers, (S)-6,7-dichloro-1-(trifluoromethyl)-2,3,4,9-tetrahydro-1H-carbazol-1-ol and (R)-6,7-dichloro-1-(trifluoromethyl)-2,3,4,9-tetrahydro-1H-carbazol-1-ol were 5.36 min. and 11.69 min respectively. The ee for each enantiomer was greater than 99%. The absolute stereochemistry for each enantiomer was not determined Example 10

(R)-6,8-Dichloro-1-(trifluoromethyl)-2,3,4,9-tetrahydro-1H-carbazol-1-ol

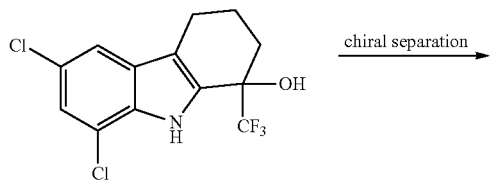

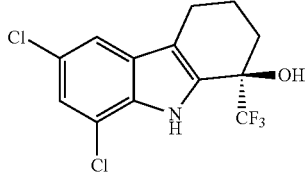

A racemic mixture of 6,8-dichloro-1-(trifluoromethyl)-2,3,4,9-tetrahydro-1H-carbazol-1-ol (Example 8) was separated by chiral HPLC using the following conditions:
Chiral HPLC Method:
Chiral column: CHIRALPAK IA 250×4.6 mm, 5μ
Mobile phase A: n-Heptane
Mobile phase B: Isopropanol
Isocratic: A:B (95:5)
Flow rate: 1.00 mL/min
Detection: λ 230 nm
Retention time: 9.49 min.

The ee was >98%; the absolute stereochemistry was not determined.

Example 11

2,4-Dichloro-6-(trifluoromethyl)-5,6,7,8,9,10-hexahydrocyclohept[b]indol-6-ol

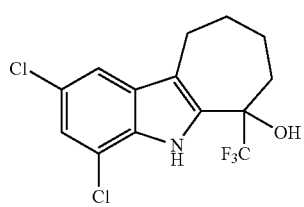 [SMILES: OC1(C(F)(F)F)CCCCc2c1[nH]c1c(Cl)cc(Cl)cc21]

Intermediate 11a

Cycloheptane-1,2-dione

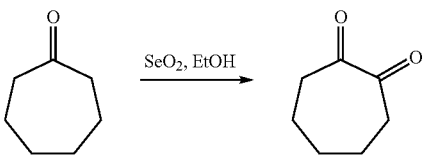 [SMILES: O=C1CCCCCC1 ; O=C1CCCCCC1=O]

To cyclohepatanone (10 g, 89.1 mmol) in EtOH (20 mL) mixed $SeO_2$ (9.88 g, 89.15 mmol) was added. The resulting mixture was stirred at 88° C. for 5 h and then cooled to room temperature. The volatiles were removed in vacuo to give the crude compound which was purified by silica gel chromatography (2% EtOAc-hexane) to give the title compound (1.2 g, 10.6%). $^1$H NMR (200 MHz, $CDCl_3$, δ in ppm) 3.60-3.36 (m, 2H), 2.61 (t, J=13.6 Hz, 1H), 1.82-1.70 (m, 2H), 1.54-1.50 (m, 2H), 1.26 (t, J=14.0 Hz, 3H).

Intermediate 11b 2,4-Dichloro-7,8,9,10-tetrahydrocyclohepta[b]indol-6(5H)-one

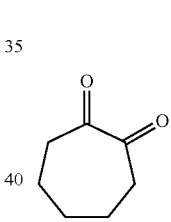

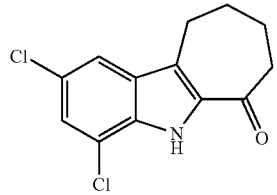

Cycloheptane-1,2-dione (1 g, 7.9 mmol) was dissolved in MeOH (25 mL) and (2,4-dichlorophenyl)hydrazine hydrochloride (1.86 g, 8.7 mmol) in AcOH—HCl (3.5:1, 45 mL) was added and heated to 60° C. for 18 h. MeOH was removed in vacuo, the reaction mixture was basified with aqueous $NaHCO_3$ (pH-8) and then extracted with EtOAc (3×25 mL), The combined organic extracts were dried over $Na_2SO_4$ and concentrated under reduced pressure to give the crude product which was purified by silica gel chromatograph [EtOAc-hexane (9:1) as eluant] to give the title compound (0.2 g, 9.4%). $^1$H NMR (200 MHz, $CDCl_3$, δ in ppm) 9.0 (br s, 1H), 7.54 (d, J=1.6 Hz, 1H), 7.33 (d, J=1.8 Hz, 1H), 3.11 (t, J=12.0 Hz, 2H), 2.90 (t, J=11.8 Hz, 2H), 2.13-2.20 (m, 4H).

Intermediate 11c 2,4-Dichloro-6-(trifluoromethyl)-6-(trimethylsilyloxy)-5,6,7,8,9,10-hexahydrocyclohepta[b]indole

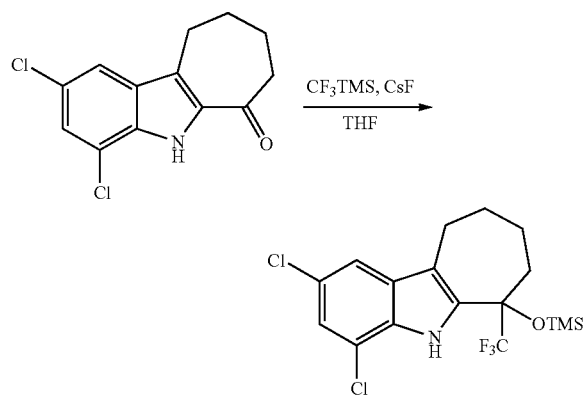

2,4-Dichloro-7,8,9,10-tetrahydrocyclohepta[b]indol-6 (5H)-one (0.24 g, 0.8 mmol) was dissolved in THF (10 mL), cooled to 0° C. and CF₃TMS (1.41 mL, 8.9 mmol) followed by CsF (0.4 g, 2.6 mmol) were added. The reaction mixture was stirred at 0° C. for 2 h and then quenched with saturated NH₄Cl (20 mL) and extracted with EtOAc (3×25 mL). The combined organic extracts were dried over Na₂SO₄ and concentrated under reduced pressure to give the crude product which was passed through a short silica pad [EtOAc-hexane (1:49) as eluant] to give the purified product (0.3 g) which was immediately in the next step.

Example 11

2,4-Dichloro-6-(trifluoromethyl)-5,6,7,8,9,10-hexahydrocyclohepta[b]indol-6-ol

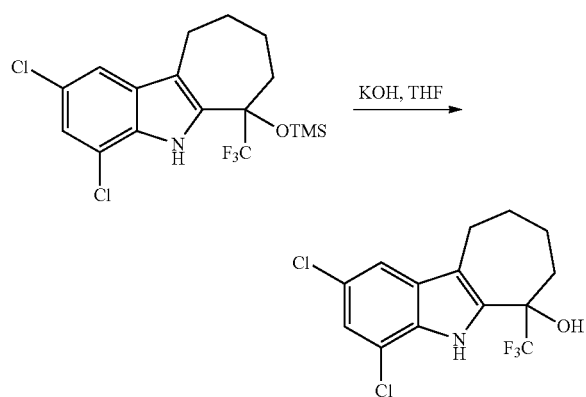

2,4-Dichloro-6-(trifluoromethyl)-6-(trimethylsilyloxy)-5,6,7,8,9,10-hexahydrocyclohepta[b]indole (0.3 g, 7.0 mmol) was dissolved in THF (5 mL) and KOH (0.2 g, 3.6 mmol) in water (5 mL) was added to the mixture. The reaction mixture was refluxed for 1 h and then cooled to room temperature, diluted with water and extracted with EtOAc (3×20 mL). The combined organic extracts were dried over Na₂SO₄ and concentrated under reduced pressure. The crude residue was purified by silica gel chromatography [EtOAc-hexane (1:17) as eluant] to furnish the title compound as a pale yellow solid (0.05 g, 21%). ¹H NMR (500 MHz, CDCl₃, δ in ppm) 8.67 (br s, 1H), 7.43 (d, J=1.5 Hz, 1H), 7.41 (d, J=1.5 Hz, 1H), 2.9 (m, 1H), 2.73 (m, 1H), 2.49 (s, 1H) 2.43-2.4 (m, 1H), 2.08-2.03 (m, 4H), 1.16-1.54 (m, 1H)

Example 12

6,7-Dichloro-2-fluoro-1-(trifluoromethyl)-2,3,4,9-tetrahydro-1H-carbazol-1-ol

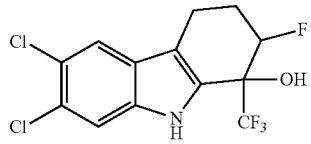 [SMILES: OC1(C(F)(F)F)c2[nH]c3cc(Cl)c(Cl)cc3c2CCC1F]

Intermediate 12a 6,7-Dichloro-2-fluoro-9-tosyl-2,3,4,9-tetrahydro-1H-carbazol-1-one

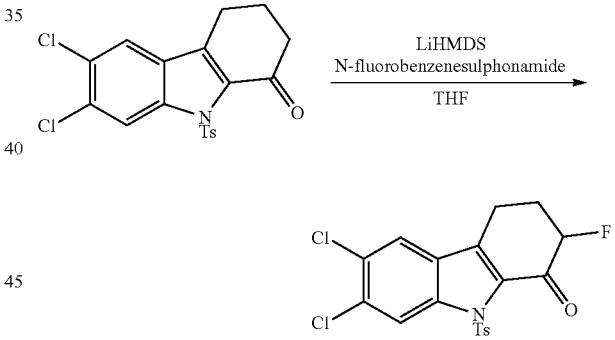

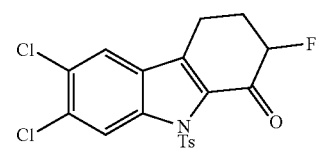

6,7-Dichloro-9-tosyl-2,3,4,9-tetrahydro-1H-carbazol-1-one (intermediate 1c) (420 mg, 1.02 mmol) dissolved in anhydrous THF (10 mL) and cooled to −78° C. was mixed with LiHMDS (1.13 mL, 1.1 mmol, 1M solution in THF). The reaction mixture was slowly warmed to 0° C., stirred for an additional 30 min. at 0° C., then cooled to −78° C. and N-fluoro benzene sulfonamide (0.31 g, 1.3 mmol) was added. The resulting mixture was slowly warmed to room temperature and stirred for 15 min., quenched with saturated NH₄Cl and extracted with EtOAc (3×20 mL). The combined organic extracts were dried over Na₂SO₄, the solvent was removed under reduced pressure to give the crude compound which was purified by column chromatography [EtOAc-hexane (7:93) as eluant] to obtain the title compound (160 mg, 37%). ¹H NMR (500 MHz, CDCl₃, δ in ppm) 8.53 (s, 1H), 8.082 (d, J=8.0 Hz, 2H), 7.69 (s, 1H), 7.35 (d, J=8.5 Hz, 2H), 5.26-5.13

(m, 1H), 3.14-3.11 (m, 1H), 3.01-2.95 (m, 1H), 2.62-2.55 (m, 1H), 2.42 (s, 3H), 2.38-2.41 (m, 1H).

Intermediate 12b 6,7-Dichloro-2-fluoro-9-tosyl-1-(trifluoromethyl)-1-(trimethylsilyloxy)-2,3,4,9-tetrahydro-1H-carbazole

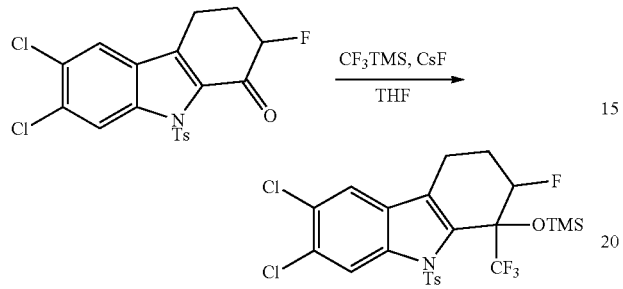

To a solution of 6,7-dichloro-2-fluoro-9-tosyl-2,3,4,9-tetrahydro-1H-carbazol-1-one (0.13 g, 0.3 mmol) in dry THF (10 mL), cooled to 0° C., CF$_3$TMS (0.46 mL, 2.9 mmol) followed by CsF (0.04 g, 0.2 mmol) were added. The reaction mixture was stirred at 0° C. for 2 h and then quenched with saturated NH$_4$Cl (20 mL) and extracted with EtOAc (3×20 mL). The combined organic extracts were dried over Na$_2$SO$_4$ and concentrated under reduced pressure to give the crude residue that was purified by passing it through a short silica pad [EtOAc-hexane (1:19) as eluant] to give the title compound (140 mg, 84%) which was used immediately in the next step without any characterization.

Example 12

6,7-Dichloro-2-fluoro-1-(trifluoromethyl)-2,3,4,9-tetrahydro-1H-carbazol-1-ol

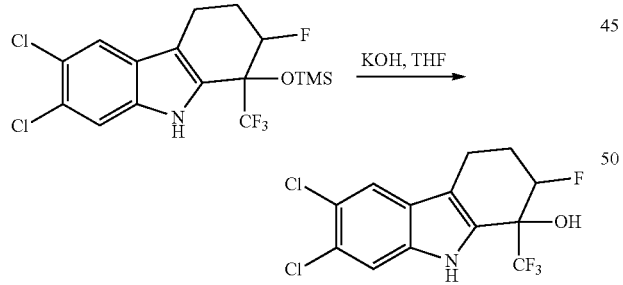

To 6,7-dichloro-2-fluoro-9-tosyl-1-(trifluoromethyl)-1-(trimethylsilyloxy)-2,3,4,9-tetrahydro-1H-carbazole (0.2 g, 0.35 mmol) in THF (10 mL), KOH (98 mg, 1.7 mmol) in H$_2$O (10 mL) was added and the resulting mixture was refluxed for 6 h. The reaction mixture was diluted with water (20 mL) and extracted with EtOAc (3×30 mL). The combined organic extracts were dried over Na$_2$SO$_4$ and concentrated in vacuo. The crude residue was purified by column chromatography [EtOAc-hexane (1:9) as eluant] and the solid obtained was washed with cold pentane to give the title compound (58 mg, 40%). $^1$H NMR (500 MHz, CDCl$_3$, δ in ppm) 8.25 (bs, 1H), 7.62 (s, 1H), 7.5 (s, 1H), 5.25-5.14 (m, 1H), 3.25 (d, J=6.5 Hz, 1H), 2.94-2.89 (m, 1H), 2.80-2.74 (m, 1H), 2.44-2.39 (m, 1H), 2.35-2.29 (m, 1H).

Example 13

5,8-Dichloro-1-(trifluoromethyl)-2,3,4,9-tetrahydro-1H-carbazol-1-ol

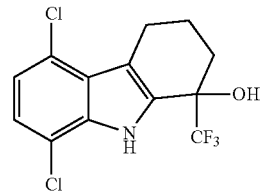 [SMILES: OC1(C(F)(F)F)CCCc2c1[nH]c1c(Cl)ccc(Cl)c21]

Intermediate 13a 5,8-Dichloro-2,3,4,9-tetrahydro-1H-carbazol-1-one

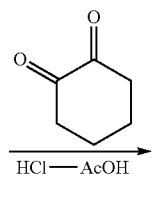

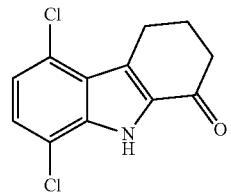

(2,5-Dichlorophenyl)hydrazine hydrochloride (0.3 g, 1.40 mmol) was dissolved in MeOH (3 mL) and 1,2-cyclo hexadione (0.15 g, 1.40 mmol) was added and the mixture heated to 60° C. for 24 h. The reaction mixture was cooled to room temperature and the volatiles were removed in vacuo. The residue was diluted with water, neutralized with NaHCO$_3$ solution and extracted with EtOAc (3×15 mL). The combined organic extracts were concentrated in vacuo to give the crude compound which was purified by silica gel chromatography [EtOAc-hexane (3:17) as eluant] to provide the title compound (0.35 g, 11.8%). $^1$H NMR (200 MHz, CDCl$_3$, δ in ppm) 8.92 (bs, 1H), 7.26 (d, J=8.2 Hz, 1H), 7.06 (d, J=8.0 Hz, 1H), 3.36 (t, J=6.2 Hz, 2H), 2.69 (t, J=6.0 Hz, 2H), 2.34-2.21 (m, 2H).

Example 13

5,8-Dichloro-4-(trifluoromethyl)-2,3,4,9-tetrahydro-1H-carbazol-1-ol

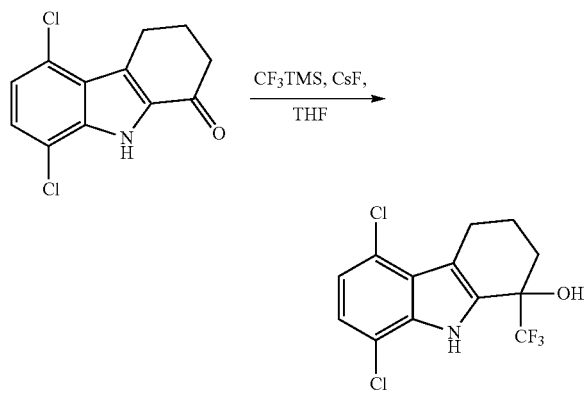

To a solution of 5,8-dichloro-2,3,4,9-tetrahydro-1H-carbazol-1-one (0.1 g, 0.39 mmol) in anhydrous THF (8 mL) at 0° C., CsF (59 mg, 0.39 mmol) and CF$_3$TMS (0.56 g, 3.93 mmol) were added. The reaction mixture was slowly warmed to room temperature and stirred for 18 h. After the volatiles were removed in vacuo, the residue was diluted with water and extracted with EtOAc (2×15 mL) to give the crude compound which was purified by silica gel chromatography [EtOAc-hexane (1:4) as eluant] to give the title compound (0.127 g, 16%). $^1$H NMR (500 MHz, DMSO-d$_6$, δ in ppm) 11.07 (s, 1H), 7.21 (d, J=8.0 Hz, 1H), 7.06 (d, J=8.5 Hz, 1H), 6.62 (s, 1H), 3.01-3.0 (m, 2H), 2.22-2.19 (m, 1H), 1.97-1.92 (m, 3H).

Example 14

5-Chloro-6-fluoro-1-(trifluoromethyl)-2,3,4,9-tetrahydro-1H-carbazol-1-ol

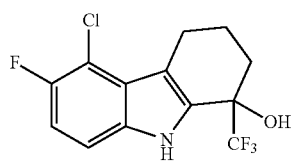 [SMILES: OC1(C(F)(F)F)CCCc2c1[nH]c1ccc(F)c(Cl)c21]

Intermediate 14a

5-Chloro-6-fluoro-2,3,4,9-tetrahydro-1H-carbazol-1-one

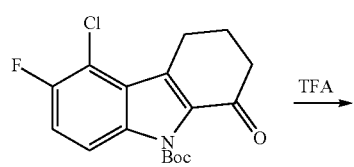

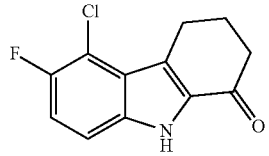

To tert-butyl 5-chloro-6-fluoro-1-oxo-3,4-dihydro-1H-carbazole-9(2H)-carboxylate (0.4 g, 1.1 mmol) in DCM (10 mL), cooled to 0° C., was added TFA (1 mL). The reaction mixture was stirred at room temperature for 4 h, quenched with saturated NaHCO$_3$ (pH-8) and then extracted with DCM (4×40 mL). The combined organic extracts were dried over Na$_2$SO$_4$ and concentrated in vacuo to give the crude compound which was washed with hexane (2×5 mL) to provide the title compound (0.20 g, 71%). $^1$H NMR (200 MHz, DMSO-d$_6$, δ in ppm) 12.04 (bs, 1H), 7.41-7.26 (m, 2H), 3.33 (t, J=6.0 Hz, 2H), 2.60 (t, J=5.8 Hz, 2H), 2.22-2.13 (m, 2H).

Intermediate 14b

5-Chloro-6-fluoro-9-tosyl-2,3,4,9-tetrahydro-1H-carbazol-1-one

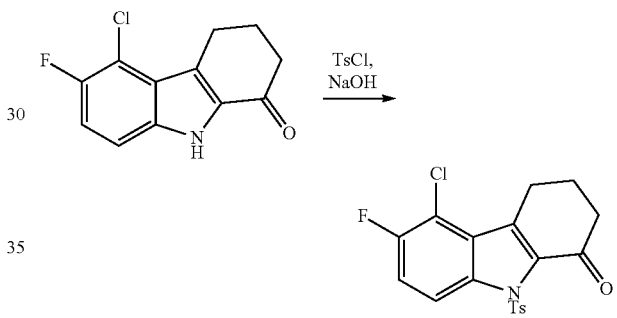

To a solution of 5-chloro-6-fluoro-2,3,4,9-tetrahydro-1H-carbazol-1-one (0.2 g, 0.8 mmol) in DCM (15 mL), cooled to 0° C., 5N NaOH (1 mL) followed by benzyl triethyl ammonium chloride (0.020 g) were added. The reaction mixture was stirred at 0° C. for 10 min. and p-TsCl (0.64 g, 3.3 mmol) was added. The reaction mixture was warmed to room temperature, stirred for 24 h at room temperature, diluted with water (10 mL) and extracted with DCM (4×30 mL). The combined organic extracts were dried over Na$_2$SO$_4$ and concentrated in vacuo to give the crude compound which was purified by chromatography [EtOAc-hexane (1:9) as eluant] to provide the title compound (0.27 g, 84%). $^1$H NMR (200 MHz, CDCl$_3$, δ in ppm) 8.29 (dd, J=9.6, 4.0 Hz, 1H), 8.02 (d, J=8.4 Hz, 2H), 7.36-7.27 (m, 3H), 3.35-3.29 (m, 2H), 2.62-2.55 (m, 2H), 2.42 (s, 3H), 2.24-2.14 (m, 2H).

Intermediate 14c

5-Chloro-6-fluoro-9-tosyl-1-(trifluoromethyl)-1-(trimethylsilyloxy)-2,3,4,9-tetrahydro-1H-carbazole

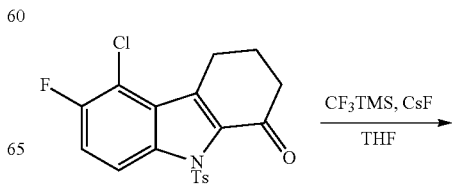

-continued

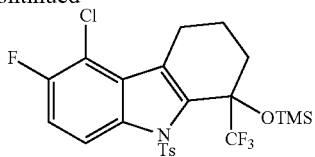

To 5-chloro-6-fluoro-9-tosyl-2,3,4,9-tetrahydro-1H-carbazol-1-one (0.12 g, 0.3 mmol) dissolved in THF (5 mL), cooled to 0° C., CF$_3$TMS (0.43 g, 3.0 mmol) and CsF (0.023 g, 0.16 mmol) were added. The reaction mixture was slowly warmed to room temperature and then stirred for 1 h at room temperature, quenched with saturated NH$_4$Cl (10 mL) and extracted with EtOAc (3×10 mL). The combined organic extracts were dried over Na$_2$SO$_4$ and concentrated under reduced pressure to obtain the crude compound which was quickly purified by column chromatography [EtOAc-hexane (1:9) as eluant] to give the title compound (0.080 mg, 50%) that was used immediately in the next step.

Example 14

5-Chloro-6-fluoro-1-(trifluoromethyl)-2,3,4,9-tetrahydro-1H-carbazol-1-ol

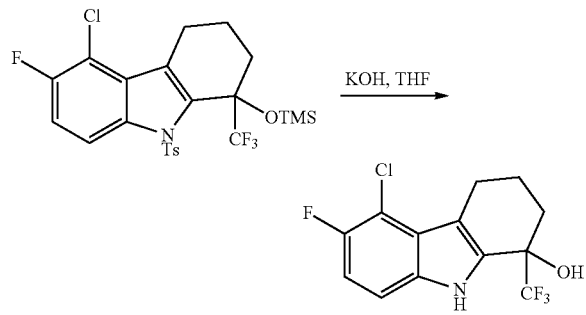

To a solution of 5-chloro-6-fluoro-9-tosyl-1-(trifluoromethyl)-1-(trimethylsilyloxy)-2,3,4,9-tetrahydro-1H-carbazole (0.08 g, 0.15 mmol) in THF (5 mL), cooled to 0° C., KOH (0.042 g, 0.7 mmol) in H$_2$O (1 mL) was added and the resulting mixture was stirred for 30 min. EtOH (4 mL) was added to the reaction mixture and heated to 60° C. for 3 h, diluted with water (10 mL) and extracted with EtOAc (4×15 mL). The combined organic extracts were dried over Na$_2$SO$_4$ and concentrated under reduced pressure to obtain the crude compound which was purified by column chromatography [EtOAc-hexane (3:17) as eluant] to give the title compound (0.025 g, 55%). $^1$H NMR (500 MHz, DMSO-d$_6$, δ in ppm) 11.22 (s, 1H), 7.34 (dd, J=9.0, 4.5 Hz, 1H), 7.14 (t, J=9.0 Hz, 1H), 6.70 (s, 1H), 3.09 (t, J=11.0 Hz, 1H), 2.94-2.89 (m, 1H), 2.10 (t, 6.5 Hz, 1H), 2.00-1.92 (m, 3H).

Example 15

5,6-Dichloro-2-fluoro-1-(trifluoromethyl)-2,3,4,9-tetrahydro-1H-carbazol-1-ol

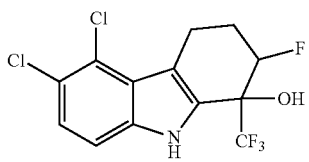 [SMILES: OC1(C(F)(F)F)c2[nH]c3ccc(Cl)c(Cl)c3c2CCC1F]

Intermediate 15a 5,6-Dichloro-2-fluoro-9-tosyl-2,3,4,9-tetrahydro-1H-carbazol-1-one

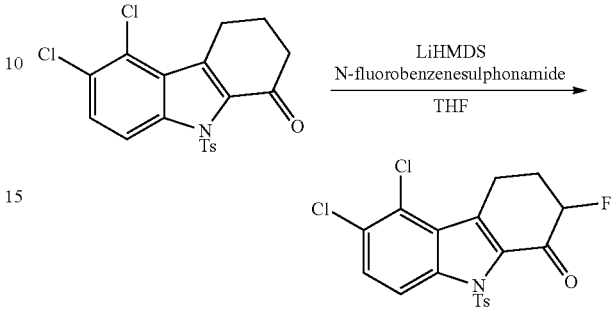

To a solution of 5,6-dichloro-9-tosyl-2,3,4,9-tetrahydro-1H-carbazol-1-one (300 mg, 0.7 mmol) in anhydrous THF (10 mL), cooled to −78° C., LiHMDS (1.47 mL, 1.4 mmol, 1M solution in THF) was added slowly. The reaction mixture was slowly warmed to 0° C. and stirred for an additional 30 min. while maintaining the temperature at 0° C. The reaction mixture was then cooled to −78° C. and N-fluoro benzene sulfonamide (0.22 g, 0.9 mmol), dissolved in THF (3 mL), was added dropwise. The reaction mixture was slowly warmed to 0° C. and stirred for 15 min during which time the reaction was complete. The reaction was quenched with saturated NH$_4$Cl and extracted with EtOAc (3×25 mL). The combined organic extracts were dried over Na$_2$SO$_4$ and concentrated under reduced pressure to give the crude compound which was purified by column chromatography [EtOAc-hexane (1:9) as eluant] to give the title compound (100 mg, 32%). $^1$H NMR (500 MHz, CDCl$_3$, δ in ppm) 8.27 (d, J=9.5 Hz, 1H), 8.07 (d, J=8.5 Hz, 2H), 7.59 (d, J=9.5 Hz, 1H), 7.35 (d, J=8.5 Hz, 2H), 5.30-5.13 (m, 1H), 3.71-3.66 (m, 1H), 3.35-3.28 (m, 1H), 2.58-2.55 (m, 1H), 2.43 (s, 3H), 2.40-2.38 (m, 1H)

Intermediate 15b 5,6-Dichloro-2-fluoro-9-tosyl-1-(trifluoromethyl)-1-(trimethylsilyloxy)-2,3,4,9-tetrahydro-1H-carbazole

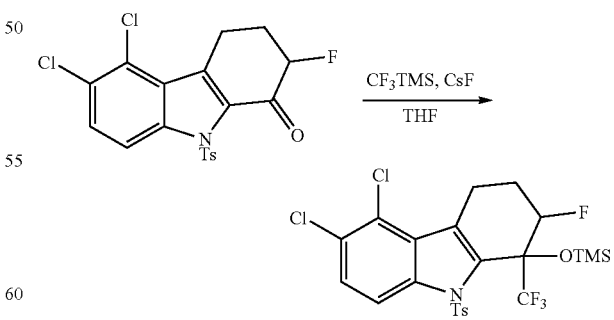

5,6-Dichloro-2-fluoro-9-tosyl-2,3,4,9-tetrahydro-1H-carbazol-1-one (120 mg, 0.2 mmol) was dissolved in anhydrous THF (10 mL), cooled to 0° C. and CF$_3$TMS (0.44 mL, 2.8 mmol) followed by CsF (0.08 g, 0.5 mmol) were added. The reaction mixture was stirred at 0° C. for 30 min, quenched with saturated NH₄Cl (20 mL) and extracted with EtOAc (3×20 mL). The combined organic extracts were dried over Na₂SO₄ and the solvent was removed under reduced pressure to give crude compound. The crude residue was quickly purified by chromatography [EtOAc-hexane (1:49) as eluant] to give the title compound (100 mg, 63%) which was used immediately in the next step without any spectroscopic analysis.

Example 15

5,6-Dichloro-2-fluoro-4-(trifluoromethyl)-2,3,4,9-tetrahydro-1H-carbazol-1-ol

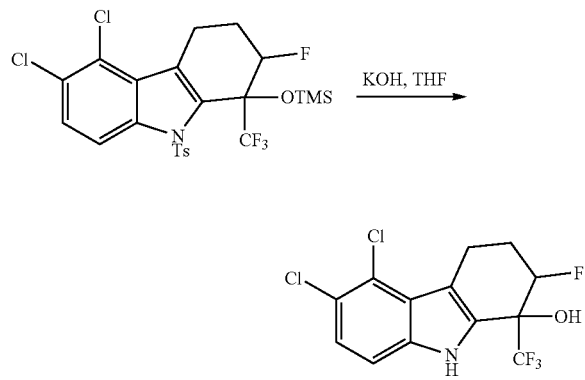

To a solution of 5,6-dichloro-2-fluoro-9-tosyl-1-(trifluoromethyl)-1-(trimethylsilyloxy)-2,3,4,9-tetrahydro-1H-carbazole (120 g, 0.24 mmol) dissolved in THF (10 mL), KOH (135 mg, 2.4 mmol) in H₂O (10 mL) was added. The reaction mixture was heated to 60° C. for 6 h, then diluted with water (25 mL) and extracted with EtOAc (2×25 mL). The combined organic extracts were dried over Na₂SO₄ and the solvent was then removed in vacuo to give the crude compound which was purified by column chromatography [EtOAc-hexane (1:19) as eluant] to give the title compound (50 mg, 61%). ¹H NMR (500 MHz, DMSO-d₆, δ in ppm) 11.51 (s, 1H), 7.41 (d, J=9.0 Hz, 1H), 7.32-7.30 (d, J=9.0 Hz, 1H), 7.22 (s, 1H), 5.21-5.09 (m, 1H), 3.17-3.09 (m, 1H), 3.08-3.03 (m, 1H), 2.36-2.29 (m, 1H), 2.18-2.10 (m, 1H).

Example 16

7-Chloro-6-fluoro-1-(trifluoromethyl)-2,3,4,9-tetrahydro-1H-carbazol-1-ol

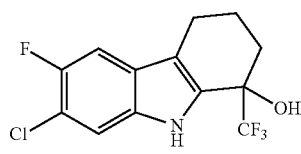 [SMILES: OC1(C(F)(F)F)CCCc2c1[nH]c1cc(Cl)c(F)cc21]

Intermediate 16a

7-Chloro-6-fluoro-2,3,4,9-tetrahydro-1H-carbazol-1-one and 5-chloro-6-fluoro-2,3,4,9-tetrahydro-1H-carbazol-1-one

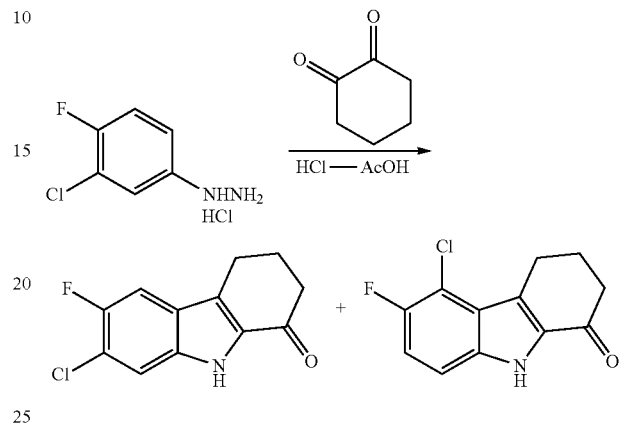

(3-Chloro-4-fluorophenyl)hydrazine hydrochloride (1.5 g, 7.6 mmol) was dissolved in MeOH (12.5 mL), heated to 60° C., and 1,2-cyclo hexadione (0.85 g, 7.6 mmol) in AcOH-conc. HCl (3:1, 16 mL) was added. The reaction mixture was stirred at 60° C. for 24 h, cooled to room temperature and the volatiles were removed in vacuo. The residue was basified with saturated NaHCO₃ solution and extracted with EtOAc (4×40 mL) to give the crude compound which was purified by silica gel chromatography [EtOAc-hexane (3:17) as eluant] to give the title compound (1 g, 55%) as a mixture of regioisomers which was used directly in the next step without any purification.

Intermediate 16b tert-Butyl 7-chloro-6-fluoro-1-oxo-3,4-dihydro-1H-carbazole-9(2H)-carboxylate and tert-butyl 5-chloro-6-fluoro-1-oxo-3,4-dihydro-1H-carbazole-9(2H)-carboxylate

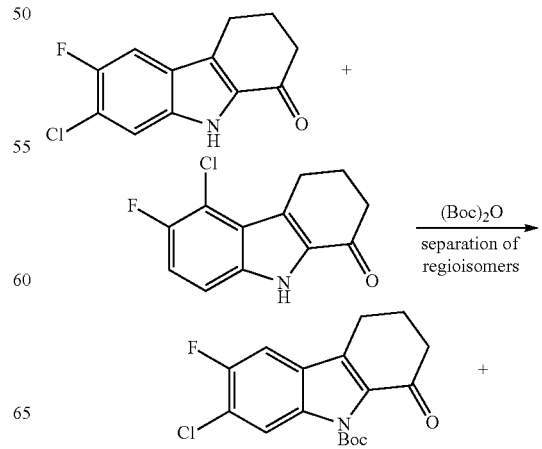

-continued

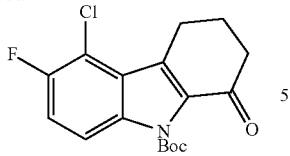

The mixture of 7-chloro-6-fluoro-2,3,4,9-tetrahydro-1H-carbazol-1-one and 5-chloro-6-fluoro-2,3,4,9-tetrahydro-1H-carbazol-1-one (0.1 g, 0.4 mmol) were dissolved in THF (10 mL), cooled to 0° C., and DMAP (0.07 g, 0.6 mmol) followed by Boc anhydride (0.11 g, 0.5 mmol) were added. The reaction was continued at 0° C. for 5 h, diluted with water (10 mL) and extracted with EtOAc (3×50 mL). The combined organic extracts were dried over Na$_2$SO$_4$, concentrated in vacuo and the crude residue was purified by chromatography using EtOAc-hexane (1:49) as eluant to give tert-butyl 5-chloro-6-fluoro-1-oxo-3,4-dihydro-1H-carbazole-9(2H)-carboxylate (0.004 g) followed by EtOAc-hexane (1:19) as eluant to give tert-butyl 7-chloro-6-fluoro-1-oxo-3,4-dihydro-1H-carbazole-9(2H)-carboxylate (0.005 g). $^1$H NMR (500 MHz, CDCl$_3$, δ in ppm) (tert-Butyl 5-chloro-6-fluoro-1-oxo-3,4-dihydro-1H-carbazole-9(2H)-carboxylate) 7.94 (dd, J=4.0 Hz, 1H), 7.26 (d, J=9.5 Hz, 1H), 3.33 (t, J=6.0 Hz, 2H), 2.66 (t, J=6.0 Hz, 2H), 2.27 (m, 2H), 1.6 (s, 9H). $^1$H NMR (500 MHz, CDCl$_3$, δ in ppm) (tert-Butyl 7-chloro-6-fluoro-1-oxo-3,4-dihydro-1H-carbazole-9(2H)-carboxylate) 8.18 (d, J=7.0 Hz, 1H), 7.32 (d, J=8.5 Hz, 1H), 2.91 (t, J=6.0 Hz, 2H), 2.68 (t, J=6.5 Hz, 2H), 2.28 (m, 2H), 1.62 (s, 9H).

Intermediate 16c

7-Chloro-6-fluoro-2,3,4,9-tetrahydro-1H-carbazol-1-one

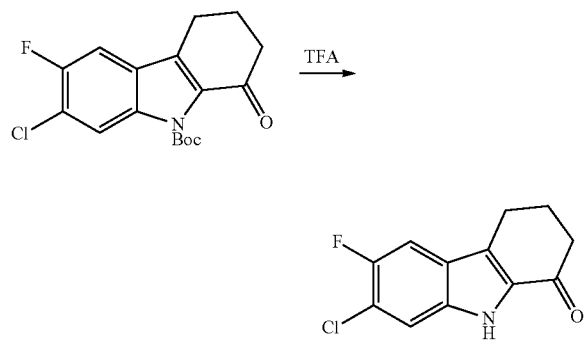

tert-Butyl 7-chloro-6-fluoro-1-oxo-3,4-dihydro-1H-carbazole-9(2H)-carboxylate (0.55 g, 1.6 mmol) was dissolved in DCM (10 mL), cooled to 0° C., and TFA (1 mL) was added slowly. The reaction mixture was brought to room temperature and stirred for 5 h, neutralized with saturated NaHCO$_3$ (10 mL) and extracted with DCM (3×10 mL). The combined organic extracts were dried over Na$_2$SO$_4$ and concentrated under reduced pressure to obtain the title compound (0.35 mg, 92%) which was used in the next step with out any purification. $^1$H NMR (200 MHz, DMSO-d$_6$, δ in ppm) 11.84 (bs, 1H), 7.76 (d, J=9.8 Hz, 1H), 7.52 (d, J=6.2 Hz, 1H), 2.95 (t, J=6.0 Hz, 2H), 2.60 (t, J=5.8 Hz, 2H), 2.20 (m, 2H).

Intermediate 16d

7-Chloro-6-fluoro-9-tosyl-2,3,4,9-tetrahydro-1H-carbazol-1-one

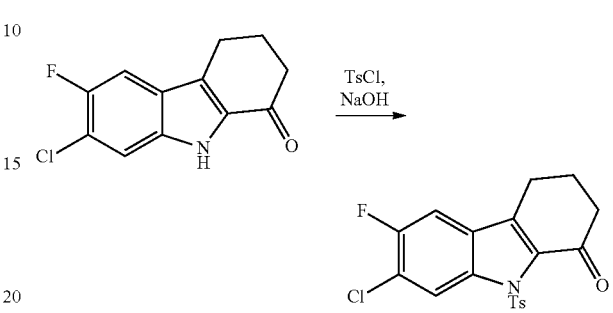

To a solution of 7-chloro-6-fluoro-2,3,4,9-tetrahydro-1H-carbazol-1-one (0.35 g, 1.4 mmol) in DCM (10 mL), cooled to 0° C., 5N NaOH (1 mL), a catalytic amount of benzene triethyl ammonium chloride (0.020 g), followed by p-TsCl (1.1 g, 5.9 mmol) were added. The reaction mixture was stirred at room temperature for 40 h, diluted with water (10 mL) and extracted with DCM (4×40 mL). The combined organic extracts were dried over Na$_2$SO$_4$ and concentrated under reduced pressure to give the crude compound which was washed with hexane (2×5 mL) to afford the title compound (0.43 g, 75%). $^1$H NMR (200 MHz, CDCl$_3$, δ in ppm) 8.49 (d, J=6.4 Hz, 1H), 8.03 (d, J=8.6 Hz, 2H), 7.37-7.26 (m, 3H), 2.91 (t, J=6.0 Hz, 2H), 2.64 (t, J=6.0 Hz, 2H), 2.42 (s, 3H), 2.24-2.14 (m, 2H).

Intermediate 16e

7-Chloro-6-fluoro-9-tosyl-1-(trifluoromethyl)-1-(trimethylsilyloxy)-2,3,4,9-tetrahydro-1H-carbazole

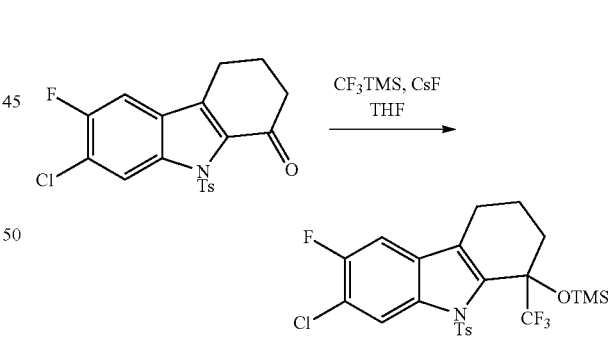

To a solution of 7-chloro-6-fluoro-9-tosyl-2,3,4,9-tetrahydro-1H-carbazol-1-one (0.1 g, 0.25 mmol) in THF (5 mL), cooled to 0° C., CF$_3$TMS (0.36 g, 2.5 mmol) followed by CsF (0.019 g, 0.12 mmol) were added. The reaction mixture was slowly warmed to room temperature and stirred for 1 h, quenched with saturated NH$_4$Cl (10 mL) and extracted with EtOAc (4×20 mL). The combined organic extracts were dried over Na$_2$SO$_4$ and concentrated under reduced pressure to provide the crude compound which was passed through a short silica pad [EtOAc-hexane (1:19) as eluant] to furnish the title compound (0.12 g, 92%) which was used immediately in the next step.

Example 16

7-Chloro-6-fluoro-1-(trifluoromethyl)-2,3,4,9-tetrahydro-1H-carbazol-1-ol

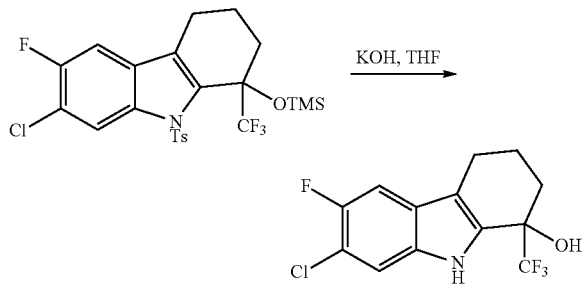

7-Chloro-6-fluoro-9-tosyl-1-(trifluoromethyl)-1-(trimethylsilyloxy)-2,3,4,9-tetrahydro-1H-carbazole (0.12 g, 0.22 mmol) was dissolved in THF (5 mL) and KOH (0.064 g, 1.0 mmol), in H$_2$O (2 mL), was added. The reaction mixture was stirred at room temperature for 30 min., followed by the addition of EtOH (2 mL) and then heated to 60° C. for 8 h, diluted with water (10 mL) and extracted with EtOAc (2×10 mL). The combined organic extracts were dried over Na$_2$SO$_4$ and concentrated under reduced pressure to give the crude compound which was purified by column chromatography [EtOAc-hexane (1:9) as eluant] to afford the title compound as an off-white solid (0.030 g, 37%). $^1$H NMR (500 MHz, DMSO-d$_6$, δ in ppm) 11.01 (s, 1H), 7.50-7.47 (m, 2H), 6.68 (s, 1H), 2.72-2.68 (m, 1H), 2.62-2.57 (m, 1H), 2.12-2.2.08 (m, 1H), 2.01-1.98 (m, 1H), 1.92-1.90 (m, 2H).

Example 17

8-Chloro-6-fluoro-1-(trifluoromethyl)-2,3,4,9-tetrahydro-1H-carbazol-1-ol

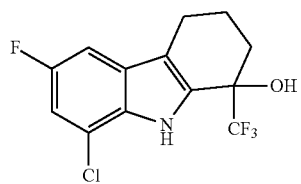 [SMILES: OC1(C(F)(F)F)CCCc2c1[nH]c1c(Cl)cc(F)cc21]

Intermediate 17a

8-Chloro-6-fluoro-2,3,4,9-tetrahydro-1H-carbazol-1-one

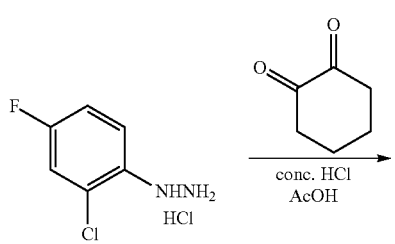

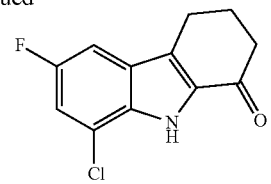

To 2-chloro-4-fluoro phenyl hydrazine hydrochloride (0.3 g, 1.5 mmol) in MeOH (2.5 mL), a solution of 1,2-cyclohexadione (0.17 g, 1.5 mmol) in AcOH (2.5 mL) and conc. HCl (1 mL) were added. The resulting mixture was stirred at 60° C. for 12 h, then cooled to room temperature and MeOH was removed in vacuo. Water (25 mL) was added and the reaction mixture was basified with NaHCO$_3$ (pH 8). The crude residue was extracted with EtOAc (2×30 mL). The combined organic extracts were washed with water (50 mL), dried over Na$_2$SO$_4$ and concentrated in vacuo to give the crude material which was purified by silica gel chromatography [EtOAc-hexane (1:19) as eluant] to afford the title compound (0.2 g, 55%). $^1$H NMR (200 MHz, CDCl$_3$, δ in ppm) 8.84 (bs, 1H), 7.26-7.17 (m, 2H), 2.99-2.93 (t, J=6.0 Hz, 2H), 2.70-2.64 (q, J=7.4, 5.8 Hz, 2H), 2.34-2.21 (m, 2H).

Intermediate 17b

8-Chloro-6-fluoro-1-(trifluoromethyl)-1-(trimethylsilyloxy)-2,3,4,9-tetrahydro-1H-carbazole

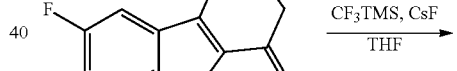

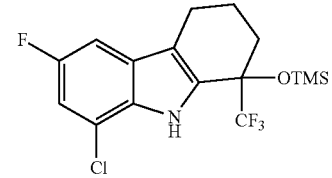

8-Chloro-6-fluoro-2,3,4,9-tetrahydro-1H-carbazol-1-one (0.075 g, 0.316 mmol) was dissolved in dry THF (5 mL), cooled to 0° C., and CsF (0.144 g, 0.94 mmol) followed by CF$_3$TMS (0.5 mL, 3.16 mmol) were added. The resulting mixture was warmed to room temperature and then stirred for 20 min., saturated NH$_4$Cl (25 mL) was added followed by extracted with EtOAc (2×25 mL). The combined organic extracts were dried over Na$_2$SO$_4$, concentrated under reduced pressure and the crude residue (0.1 g) was used immediate in the next step without purification.

Example 17

8-Chloro-6-fluoro-1-(trifluoromethyl)-2,3,4,9-tetrahydro-1H-carbazol-1-ol

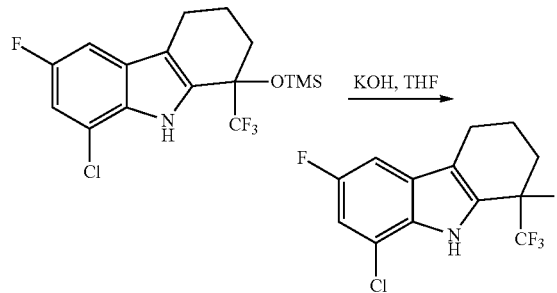

8-Chloro-6-fluoro-1-(trifluoromethyl)-1-(trimethylsilyloxy)-2,3,4,9-tetrahydro-1H-carbazole (0.1 g, 0.26 mmol) was dissolved in THF (10 mL) and KOH (0.073 g, 1.3 mmol), in water (2 mL), was added. The reaction mixture was stirred at room temperature for 2 h, diluted with water (25 mL) and extracted with EtOAc (2×25 mL). The combined organic extracts were dried over Na$_2$SO$_4$, concentrated in vacuo to give the crude compound which was purified by silica gel chromatography [EtOAc-hexane (1:4) as eluant] to provide the title compound (0.02 g, 24%) (HPLC 96%). $^1$H NMR (500 MHz, CDCl$_3$, δ in ppm) 8.27 (bs, 1H), 7.12-7.11 (d, J=9.0 Hz, 1H), 7.08-7.0 (d, J=8.5 Hz, 1H), 2.82-2.77 (m, 1H), 2.71-2.65 (m, 1H), 2.49 (s, 1H), 2.29-2.23 (m, 1H), 2.12-2.09 (m, 1H), 2.05-2.02 (m, 2H).

Example 18

8-Chloro-6-fluoro-1,2-bis(trifluoromethyl)-2,3,4,9-tetrahydro-1H-carbazol-1-ol

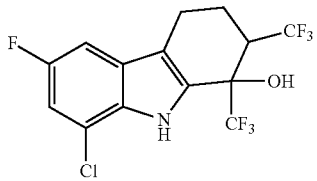 [SMILES: OC1(C(F)(F)F)c2[nH]c3c(Cl)cc(F)cc3c2CCC1C(F)(F)F]

Intermediate 18a

8-Chloro-6-fluoro-1,2-bis(trifluoromethyl)-1-(trimethylsilyloxy)-2,3,4,9-tetrahydro-1H-carbazole

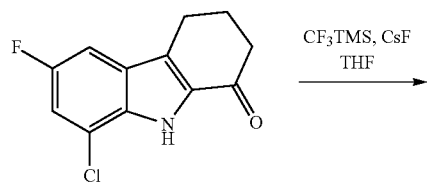

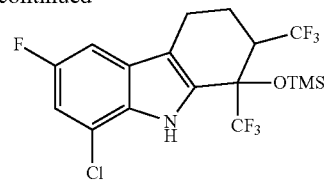

8-Chloro-6-fluoro-2,3,4,9-tetrahydro-1H-carbazol-1-one (intermediate 17a) (0.2 g, 0.84 mmol) was dissolved in dry THF (10 mL), cooled to 0° C., and CsF (0.128 g, 0.84 mmol) followed by CF$_3$TMS (1.33 mL, 8.4 mmol) were added. The resulting mixture was brought to room temperature and then stirred for an additional 2 h, saturated NH$_4$Cl (20 mL) was added and extracted with EtOAc (2×25 mL). The combined organic extracts were dried over Na$_2$SO$_4$, concentrated in vacuo to provide the crude compound which was purified by silica gel chromatography [EtOAc-hexane (1:19) as eluant] to give the title compound (0.2 g, 53%). $^1$H NMR (500 MHz, CDCl$_3$, δ in ppm) 8.39 (bs, 1H), 7.25-7.24 (d, J=9.5 Hz, 1H), 7.13-7.09 (m, 1H), 3.68-3.64 (t, J=10 Hz, 1H), 2.52-2.33 (m, 2H), 2.22-2.09 (m, 2H).

Example 18

8-Chloro-6-fluoro-1,2-bis(trifluoromethyl)-2,3,4,9-tetrahydro-1H-carbazol-1-ol

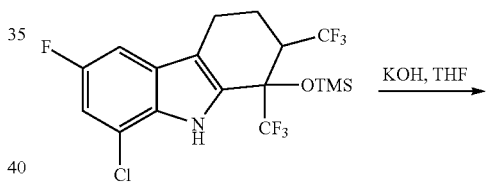

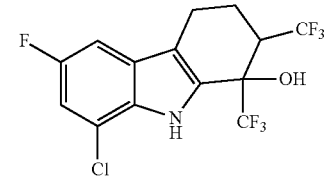

8-Chloro-6-fluoro-1,2-bis(trifluoromethyl)-1-(trimethylsilyloxy)-2,3,4,9-tetrahydro-1H-carbazole (0.2 g, 0.44 mmol) was dissolved in THF (10 mL) and KOH (0.125 g, 2.2 mmol), water (2 mL), was added. The reaction mixture was stirred at room temperature for 2 h, diluted with water (25 mL) and extracted with EtOAc (2×25 mL). The combined organic extracts were dried over Na$_2$SO$_4$, concentrated in vacuo and purified by column chromatography [EtOAc-hexane (1:19) as eluant] to obtain the title compound (0.070 g, 42%) (HPLC 99%). $^1$H NMR (500 MHz, CDCl$_3$, δ in ppm) 8.49 (br s, 1H), 7.26-7.23 (d, J=11.0 Hz, 1H), 7.14-7.11 (dd, J=8.5, 2.0 Hz, 1H), 3.71-3.67 (m, 1H), 2.60-2.57 (m, 1H), 5.54 (s, 1H), 2.40-2.37 (m, 1H), 2.30-2.24 (m, 1H), 2.10-2.07 (m, 1H).

Example 19

6,7-Dichloro-2,2-difluoro-1-(trifluoromethyl)-2,3,4,9-tetrahydro-1H-carbazol-1-ol

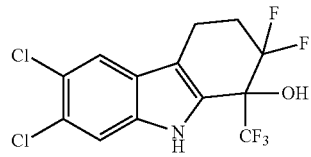 [SMILES: OC1(C(F)(F)F)c2[nH]c3cc(Cl)c(Cl)cc3c2CCC1(F)F]

Intermediate 19a 6,7-Dichloro-2,2-difluoro-9-tosyl-2,3,4,9-tetrahydro-1H-carbazol-1-one

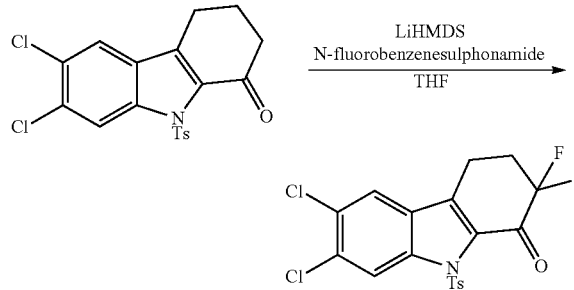

To a solution of 6,7-dichloro-9-tosyl-2,3,4,9-tetrahydro-1H-carbazol-1-one (intermediate 3a) (0.35 g, 0.8 mmol) in dry THF (10 mL), cooled to −78° C., LiHMDS (2.5 mL, 2.6 mmol, 1M solution in THF) was added and the reaction mixture was slowly warmed to 0° C. and stirred for an additional 30 min. The reaction mixture was cooled to −78° C. and N-fluoro benzene sulfonamide (0.61 g, 2.6 mmol) was added. The reaction mixture was slowly warmed to room temperature, stirred for 1 h, quenched with saturated NH₄Cl and extracted with EtOAc (3×20 mL). The combined organic extracts were dried over Na₂SO₄ and concentrated under reduced pressure to give the crude compound which was purified by column chromatography [EtOAc-hexane (1:9) as eluant] to give the title compound (0.20 g, 54%). ¹H NMR (500 MHz, CDCl₃, in ppm) 8.57 (s, 1H), 8.05 (d, J=8.0 Hz, 2H), 7.73 (s, 1H), 7.35 (d, J=8.5 Hz, 2H), 3.12 (t, J=6.0 Hz, 2H), 2.63-2.57 (m, 2H), 2.43 (s, 3H).

Intermediate 19b 6,7-Dichloro-2,2-difluoro-9-tosyl-1-(trifluoromethyl)-1-(trimethylsilyloxy)-2,3,4,9-tetrahydro-1H-carbazole

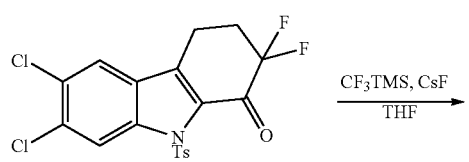

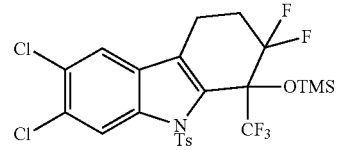

6,7-Dichloro-2,2-difluoro-9-tosyl-2,3,4,9-tetrahydro-1H-carbazol-1-one (0.12 g, 0.2 mmol) was dissolved in dry THF (10 mL), cooled to 0° C., and CF₃TMS (0.46 mL, 2.9 mmol) followed by CsF (0.13 g, 0.9 mmol) were added. The reaction mixture was stirred at 0° C. for 2 h, quenched with saturated NH₄Cl (20 mL), then extracted with EtOAc (3×10 mL). The combined organic extracts were dried over Na₂SO₄ and concentrated under reduced pressure to provide the crude title compound (0.060 g) which was used immediately in the next step without any purification.

Example 19c 6,7-Dichloro-2,2-difluoro-1-(trifluoromethyl)-2,3,4,9-tetrahydro-1H-carbazol-1-ol

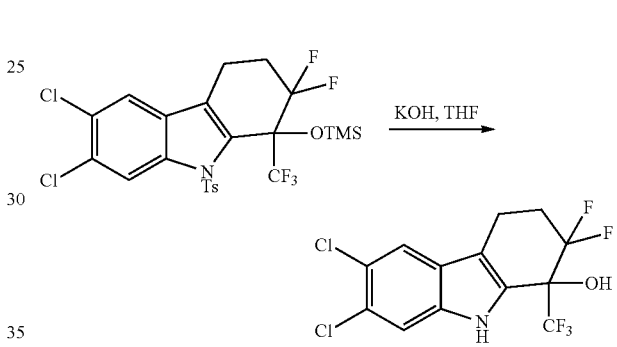

To a solution of 6,7-dichloro-2,2-difluoro-9-tosyl-1-(trifluoromethyl)-1-(trimethylsilyloxy)-2,3,4,9-tetrahydro-1H-carbazole (0.090 g, 0.2 mmol) in THF (5 mL), cooled to 0° C., KOH (0.064 g, 1.0 mmol) in H₂O (2 mL), was added and the reaction mixture was slowly cooled to room temperature and stirred for an additional 30 min EtOH (2 mL) was added to the reaction mixture and stirred at 80° C. for 4 h, diluted with water (20 mL) and extracted with EtOAc (3×30 mL). The combined organic extracts were dried over Na₂SO₄ and concentrated under reduced pressure to give the crude compound which was purified by column chromatography [EtOAc-hexane (3:17) as eluant] to give the title compound (0.025 g, 31%). ¹H NMR (500 MHz, CDCl₃, in ppm) 8.26 (bs, 1H), 7.63 (s, 1H), 7.52 (s, 1H), 3.31 (d, J=3.5 Hz, 1H), 2.97-2.94 (m, 2H), 2.61-2.52 (m, 2H).

Example 20

6,8-Dichloro-2,2-difluoro-1-(trifluoromethyl)-2,3,4,9-tetrahydro-1H-carbazol-1-ol

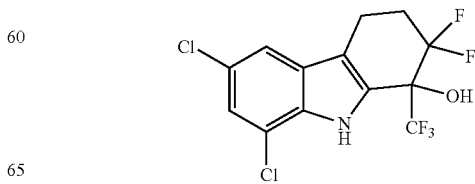

Intermediate 20a 6,8-Dichloro-2,2-difluoro-2,3,4,9-tetrahydro-1H-carbazol-1-one

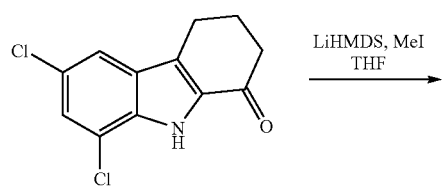

6,8-Dichloro-2,3,4,9-tetrahydro-1H-carbazol-1-one (0.5 g, 1.9 mmol) was dissolved in dry THF (10 mL), cooled to −78° C., and LiHMDS (8.0 mL, 7.9 mmol, 1M solution in THF) was added. The reaction mixture was slowly cooled to 0° C., stirred for 30 min. and then cooled to −78° C. N-fluoro benzene sulfonamide (1.4 g, 5.9 mmol) in THF (3 mL) was added dropwise while maintaining the temperature at −78° C. The reaction mixture was warmed to room temperature and stirred for an additional 8 h, cooled to 0° C., quenched with saturated NH$_4$Cl (10 mL) solution and extracted with EtOAc (2×50 mL). The combined organic extracts were dried over Na$_2$SO$_4$ concentrated under reduced pressure to give the crude residue which was purified by column chromatography [EtOAc-hexane (1:19) as eluant] to furnish the title compound (0.15 g, 33%). $^1$H NMR (500 MHz, CDCl$_3$, δ in ppm) 8.99 (br s, 1H), 7.58 (s, 1H), 7.45 (d, J=1.5 Hz, 1H), 3.19 (t, J=12.0 Hz, 2H), 2.73-2.65 (m, 2H).

Intermediate 20b 6,8-Dichloro-2,2-difluoro-(trifluoromethyl)-1-(trimethylsilyloxy)-2,3,4,9-tetrahydro-1H-carbazole

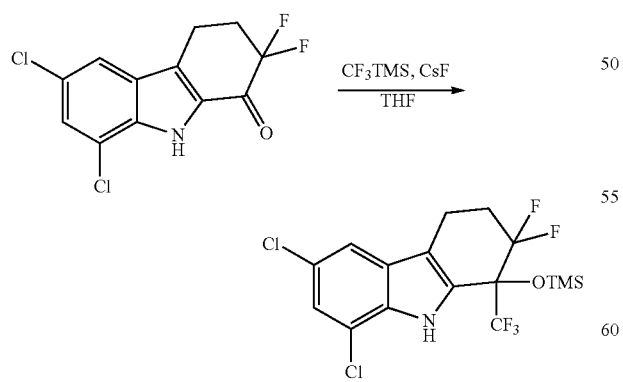

6,8-Dichloro-2,2-difluoro-2,3,4,9-tetrahydro-1H-carbazol-1-one (0.15 g, 0.28 mmol) was dissolved in dry THF (10 mL), cooled to 0° C., and CsF (0.24 g, 1.5 mmol) followed by CF$_3$TMS (0.9 mL, 5.1 mmol) was added while maintaining the temperature at 0° C. The reaction was quenched with saturated NH$_4$Cl, extracted with EtOAc (2×50 mL) and the combined organic extracts were dried over Na$_2$SO$_4$ and concentrated in vacuo to give the crude title compound (0.12 g) which was used immediately in the next step without any purification.

Example 20

6,8-Dichloro-2,2-difluoro-1-(trifluoromethyl)-2,3,4,9-tetrahydro-1H-carbazol-1-ol

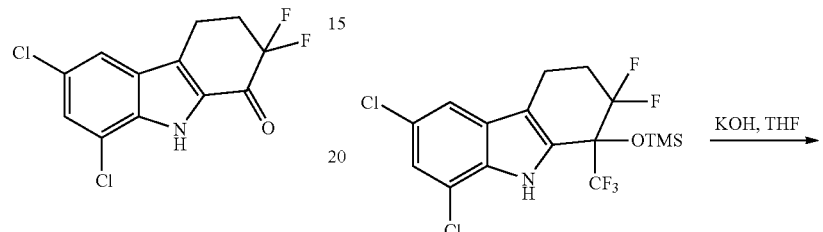

6,8-Dichloro-2,2-difluoro-1-(trifluoromethyl)-1-(trimethylsilyloxy)-2,3,4,9-tetrahydro-1H-carbazole (0.12 g, 0.27 mmol) was dissolved in THF (5 mL) and KOH (0.055 g, 1.1 mmol) in water (5 mL) was added. The reaction mixture was stirred at room temperature for 2 h, diluted with water (10 mL) and extracted with EtOAc (2×50 mL). The combined organic extracts were dried over Na$_2$SO$_4$, concentrated under reduced pressure to give the crude material which was purified by column chromatography [EtOAc-hexane (1:9) as eluant] to furnish the title compound. (0.012 g, 12%). $^1$H NMR (500 MHz, CDCl$_3$, δ in ppm) 8.41 (br s, 1H), 7.44 (s, 1H), 7.3 (s, 1H), 3.35 (br s, 1H), 2.97 (t, J=12.0 Hz, 2H), 2.61-2.54 (m, 2H).

Example 21

5,6,8-Trichloro-1-(trifluoromethyl)-2,3,4,9-tetrahydro-1H-carbazol-1-ol

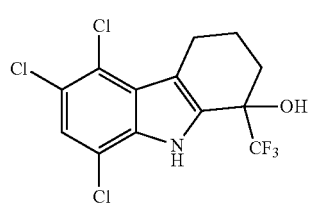 [SMILES: OC1(C(F)(F)F)CCCc2c1[nH]c1c(Cl)cc(Cl)c(Cl)c21]

Intermediate 21a 2-(2-(2,4,5-Trichlorophenyl)hydrazono)cyclohexanone

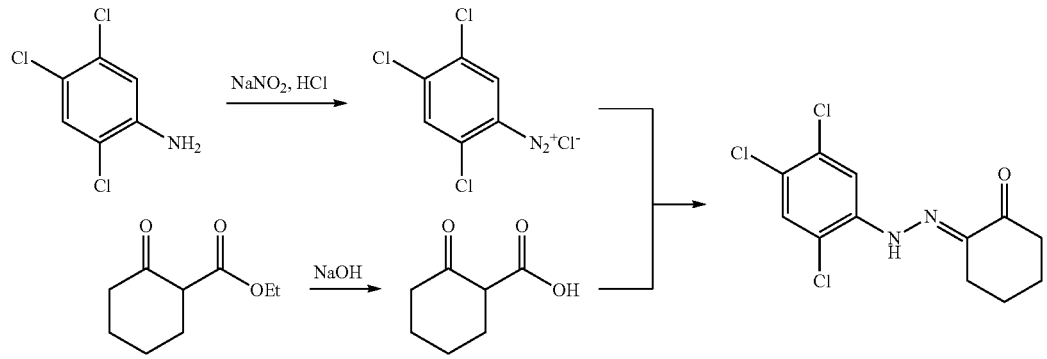

To a solution of 2,4,5-trichloroaniline (2.48 g, 12.6 mmol) in H$_2$O (5 mL), cooled to 0° C., conc. HCl (7.5 mL) was added, and then stirred for 20 min. NaNO$_2$ (0.87 g, 12.0 mmol) dissolved in water (5 mL), was added slowly and the reaction was continued at 0° C. for 1 h, filtered and the filtrate was used further. In another setup, ethyl 2-oxocyclohexanecarboxylate (2.0 g, 12.0 mmol) was added to 5N NaOH (0.56 g) and stirred for 16 h. The reaction mixture was cooled to 0° C., conc. HCl (1.2 mL) was added slowly, stirred for another 45 min. to obtain 2-oxocyclohexanecarboxylic acid which was added to the filtrate (prepared above) at 0° C. The resulting yellow solid precipitate was filtered, air dried to give the title compound (1.7 g, 44%) which was used in the next step without any spectroscopic analysis.

Intermediate 21b 5,6,8-Trichloro-2,3,4,9-tetrahydro-1H-carbazol-1-one

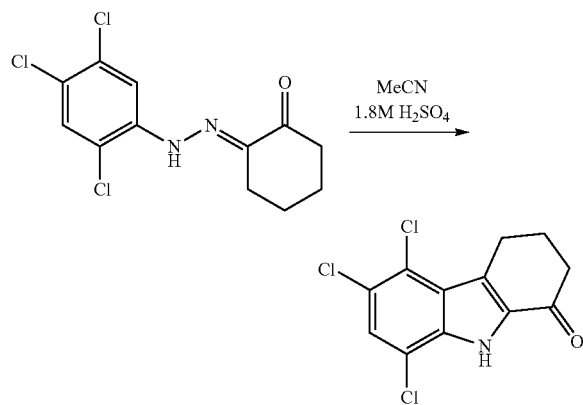

2-(2-(2,4,5-Trichlorophenyl)hydrazono)cyclohexanone (0.3 g, 0.98 mmol) was dissolved in MeCN (6 mL) and H$_2$SO$_4$ (0.1 mL, 1.8 M solution) was added. The reaction mixture was heated to 80° C. for 4 h and slowly cooled to room temperature. Saturated NaHCO$_3$ was added to the reaction mixture until pH 5-6 was obtained and then extracted with EtOAc (3×20 mL). The combined organic extracts were dried over Na$_2$SO$_4$ and concentrated in vacuo to obtain the crude compound which was purified by silica gel chromatography [EtOAc-hexane (1:4) as eluant] to furnish the title compound as a brown solid (0.1 g, 35%). $^1$H NMR (200 MHz, DMSO-d$_6$, δ in ppm) 12.55 (bs, 1H), 7.68 (s, 1H), 3.27 (t, J=5.6 Hz, 2H), 2.63 (t, J=6.0 Hz, 2H), 2.19 (m, 2H).

Example 21

5,6,8-Trichloro-(trifluoromethyl)-2,3,4,9-tetrahydro-1H-carbazol-1-ol

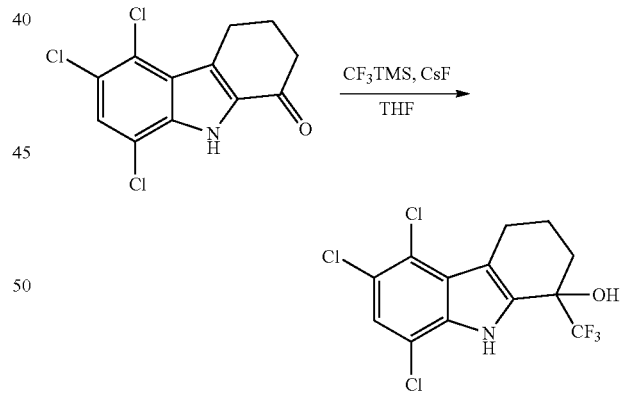

To a solution of 5,6,8-trichloro-2,3,4,9-tetrahydro-1H-carbazol-1-one (0.1 g, 0.3 mmol) in anhydrous THF (5 mL), cooled to 0° C., CF$_3$TMS (0.5 mL) followed by CsF (0.026 g, 0.17 mmol) were added. The reaction mixture was stirred at 0° C. for 1 h, cooled to room temperature and stirred for an additional 16 h, quenched with saturated NH$_4$Cl (20 mL) and extracted with EtOAc (3×10 mL). The combined organic extracts were dried over Na$_2$SO$_4$ and concentrated under reduced pressure to give the crude compound which was purified by column chromatography [EtOAc-hexane (3:17) as eluant] to afford the title compound as a yellow solid (0.042 g, 32%). $^1$H NMR (500 MHz, DMSO-d$_6$, δ in ppm) 11.42 (s, 1H), 7.52 (s, 1H), 6.69 (s, 1H), 3.02 (m, 2H), 2.21 (m, 1H), 1.96 (m, 3H).

Example 22

5,7-Dichloro-3-(trifluoromethyl)-1,2,3,4-tetrahydrocyclopenta[b]indol-3-ol

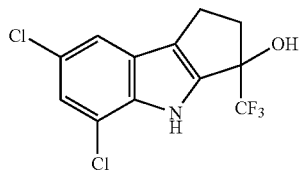 [SMILES: OC1(C(F)(F)F)CCc2c1[nH]c1c(Cl)cc(Cl)cc21]

Intermediate 22a 2-(2-(2,4-Dichlorophenyl)hydrazono)cyclopentanone

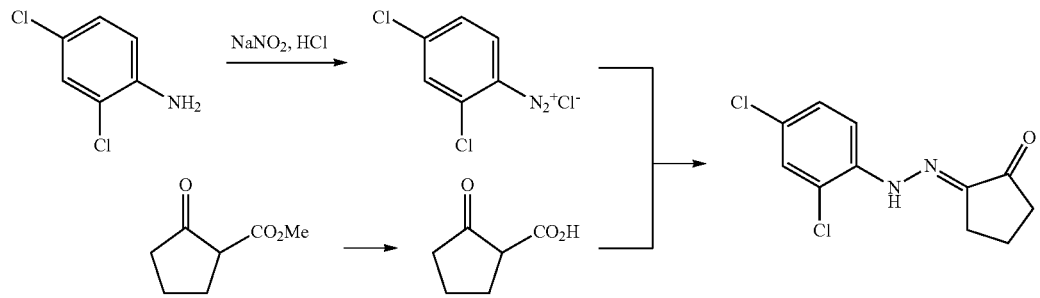

To 2,4-dichloroaniline (2.7 g, 16.6 mmol) in H$_2$O (10 mL), cooled to 0° C., conc. HCl (7 mL) was added and stirred for 20 min. NaNO$_2$ (1.29 g, 18.6 mmol), dissolved in water (10 mL) was added slowly to the reaction mixture and stirred for 30 min. while maintaining the temperature at 0° C. The reaction mixture was filtered and the filtrate was used further.

In another setup, methyl 2-oxocyclopentanecarboxylate (2.5 g, 17.5 mmol) in 5N NaOH (0.75 g, 18.8 mmol) was stirred for 16 h, cooled to 0° C., acidified with conc. HCl (1.1 mL) and added slowly to the diazonium salt prepared above. The reaction mixture was stirred at 0° C. for 10 min. during which time a yellow solid precipitated. The solid was filtered, air dried to give the title compound (2.2 g, 52%). $^1$H NMR (200 MHz, CDCl$_3$, δ in ppm) 13.11 (bs, 1H), 7.66 (d, J=9.0 Hz, 1H), 7.32 (d, J=2.0 Hz, 1H), 7.23 (dd, J=8.8, 2.2 Hz, 1H), 2.83 (t, J=7.2 Hz, 2H), 2.55 (t, 7.8 Hz, 2H), 2.19 (m, 2H).

Intermediate 22b 5,7-dichloro-1,2-dihydrocyclopenta[b]indol-3(4H)-one

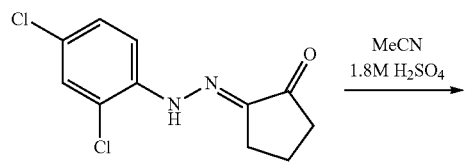

To a solution of 2-(2-(2,4-dichlorophenyl)hydrazono)cyclopentanone (2.2 g, 8.59 mmol) in MeCN (10 mL), H$_2$SO$_4$ (1.4 mL, 1.8M solution) was added and the mixture stirred at 80° C. for 16 h. The reaction mixture was cooled to room temperature, basified with saturated NaHCO$_3$ and extracted with EtOAc (3×30 mL). The combined organic extracts were dried over Na$_2$SO$_4$ and concentrated in vacuo to give the crude title compound as an off-white solid (800 mg) which was used in the next step without purification.

Intermediate 22c (5,7-Dichloro-3-oxo-2,3-dihydrocyclopenta[b]indol-4(1H)-yl)methyl pivalate

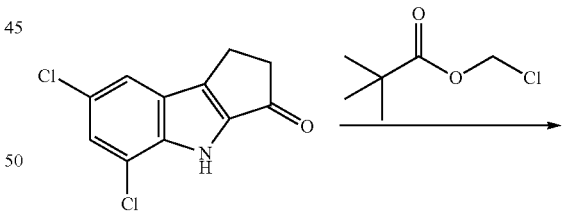

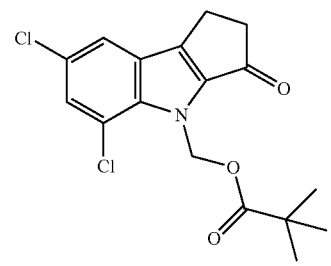

To a solution of 5,7-dichloro-1,2-dihydrocyclopenta[b]indol-3(4H)-one (0.1 g, 0.41 mmol) in anhydrous DMF (5 mL), $K_2CO_3$ (80 mg, 0.62 mmol) was added followed by chloro methyl pivalate (0.07 mL, 0.51 mmol) and the resulting mixture stirred at room temperature for 3 h. The reaction mixture was diluted with water (10 mL) and extracted with EtOAc (3×10 mL). The combined organic extracts were dried over $Na_2SO_4$ and concentrated under reduced pressure to give the crude compound which was purified by silica gel chromatography [EtOAc-hexane (3:17) as eluant] to provide the title compound as a yellow solid (0.10 g, 68%). $^1$H NMR (500 MHz, $CDCl_3$, δ in ppm) 7.61 (s, 1H), 7.41 (s, 1H), 6.56 (s, 2H), 3.04 (s, 4H), 1.14 (s, 9H).

Intermediate 22d (5,7-Dichloro-3-(trifluoromethyl)-3-(trimethylsilyloxy)-2,3-dihydrocyclopenta[b]indol-4(1H)-yl)methyl pivalate

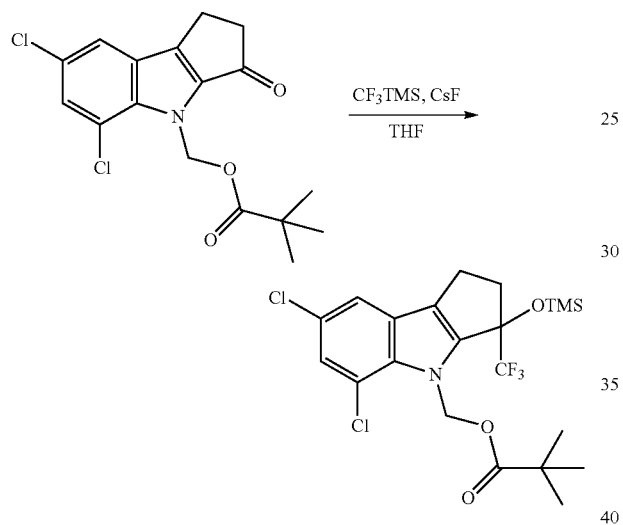

(5,7-Dichloro-3-oxo-2,3-dihydrocyclopenta[b]indol-4(1H)-yl)methyl pivalate (0.30 g, 0.8 mmol) was dissolved in dry THF (10 mL), cooled to 0° C. and $CF_3TMS$ (1.4 mL, 8.0 mmol) followed by CsF (0.13 g, 0.8 mmol) were added. The reaction mixture was stirred at 0° C. for 15 min., quenched with saturated $NH_4Cl$ and extracted with EtOAc (2×20 mL). The combined organic extracts were dried over $Na_2SO_4$ and concentrated in vacuo to give the crude title compound which was quickly passed through a short silica gel pad and used immediately in the next step.

Example 22

5,7-Dichloro-3-(trifluoromethyl)-1,2,3,4-tetrahydrocyclopenta[b]indol-3-ol

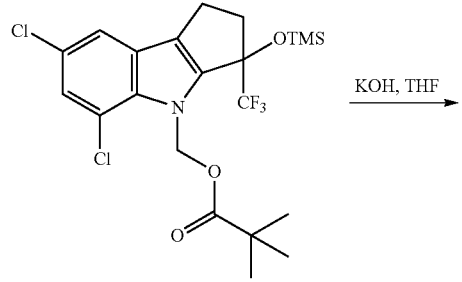

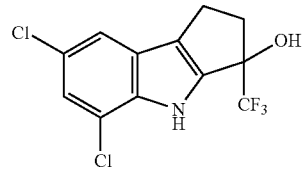

To (5,7-Dichloro-3-(trifluoromethyl)-3-(trimethylsilyloxy)-2,3-dihydrocyclopenta[b]indol-4(1H)-yl)methyl pivalate (0.32 g, 0.6 mmol) in THF (6.0 mL), cooled to 0° C., KOH (0.18 g, 3.2 mmol), in $H_2O$ (6.0 mL) was added. The reaction mixture was slowly warmed to room temperature and stirred for 16 h, diluted with water (10 mL) and extracted with $CH_2Cl_2$ (3×10 mL). The combined organic extracts were dried over $Na_2SO_4$ and concentrated under reduced pressure to give the crude compound which was purified by silica gel chromatography [EtOAc-hexane (3:17) as eluant] to afford the title compound as a white solid (0.80 g, 40%). $^1$H NMR (500 MHz, DMSO-$d_6$, δ in ppm) 11.75 (s, 1H), 7.55 (s, 1H), 7.30 (d, 1.5 Hz, 1H), 6.83 (s, 1H), 2.93-2.88 (m, 2H), 2.78-2.74 (m, 1H), 2.53-2.50 (m, 1H).

Example 23

5,6-Dichloro-2-methyl-1-(trifluoromethyl)-2,3,4,9-tetrahydro-1H-carbazol-1-ol

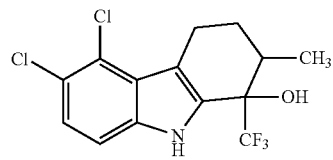 [SMILES: CC1CCc2c([nH]c3ccc(Cl)c(Cl)c23)C1(O)C(F)(F)F]

Intermediate 23a 5,6-Dichloro-2-methyl-9-tosyl-2,3,4,9-tetrahydro-1H-carbazol-1-one

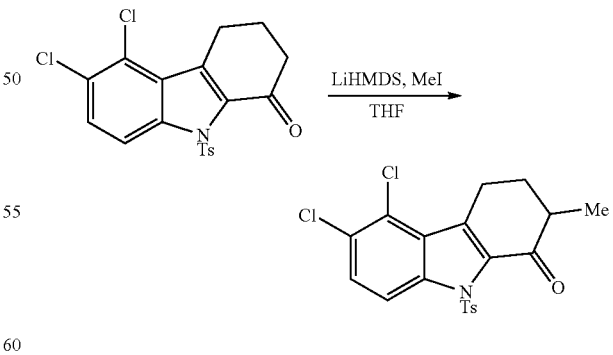

5,6-Dichloro-9-tosyl-2,3,4,9-tetrahydro-1H-carbazol-1-one (intermediate 5b) (0.15 g, 0.036 mmol) was dissolved in dry THF, cooled to −78° C. and LiHMDS (0.8 mL, 0.88 mmol, 1M solution in THF) was added dropwise. The reaction mixture was slowly warmed to 0° C. and stirred for an additional 30 min. The reaction mixture was cooled to −78° C. and MeI (0.05 ml, 0.88 mmol) was added slowly, and the reaction mixture was slowly, warmed to room temperature and stirred for 4 h. The reaction was cooled to 0° C. and quenched with saturated NH₄Cl (10 mL) and extracted with EtOAc (2×50 ml). The combined organic extracts were dried over Na₂SO₄ and concentrated under reduced pressure. The crude material obtained was purified by column chromatography using [EtOAc-hexane (1:9) as eluant] to afford the title compound (0.05 g, 32%). ¹H NMR (500 MHz, CDCl₃, δ in ppm) 8.22 (d, J=8.5 Hz, 1H), 8.02 (d, J=8.5 Hz, 2H), 7.54 (d, J=9 Hz, 1H), 7.34 (d, J=8.5 Hz, 2H), 3.55-3.49 (m, 1H), 3.22-3.15 (m, 1H), 2.68-2.64 (m, 1H), 2.42 (s, 3H), 2.27-2.22 (m, 1H), 1.95-1.87 (m, 1H), 1.25-1.17 (m, 3H).

m/z=422 (M+1)

Intermediate 23b 5,6-Dichloro-2-methyl-1-(trifluoromethyl)-1-(trimethylsilyloxy)-2,3,4,9-tetrahydro-1H-carbazole

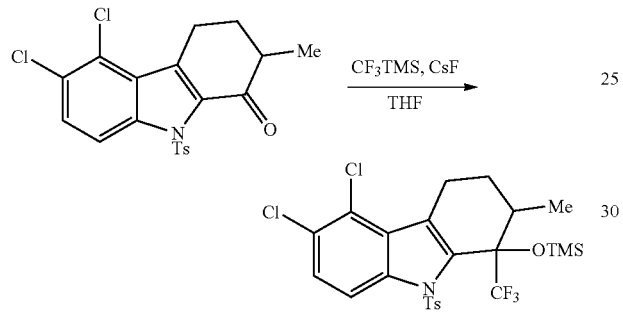

5,6-Dichloro-2-methyl-9-tosyl-2,3,4,9-tetrahydro-1H-carbazol-1-one (0.15 g, 0.35 mmol) was dissolved in dry THF (10 mL), cooled to 0° C. and CsF (0.16 g, 1.06 mmol) followed by CF₃TMS (0.6 mL, 3.5 mmol) was added. The reaction mixture was stirred at 0° C. for 1 h, quenched with sat. NH₄Cl (10 mL) and extracted into EtOAc (2×50 ml). The combined organic extracts were dried (Na₂SO₄) and concentrated under reduced pressure to give crude product which was used in the next step without purification (0.15 g).

Example 23

5,6-Dichloro-2-methyl-1-(trifluoromethyl)-2,3,4,9-tetrahydro-1H-carbazol-1-ol

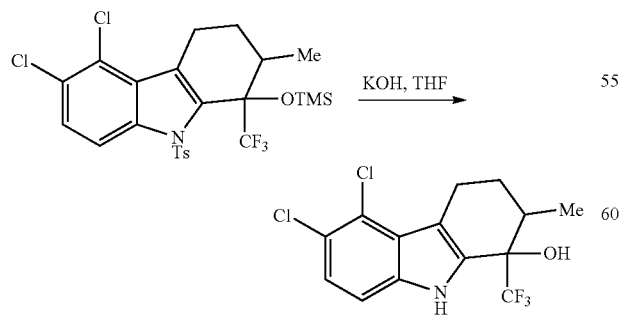

5,6-Dichloro-2-methyl-1-(trifluoromethyl)-1-(trimethylsilyloxy)-2,3,4,9-tetrahydro-1H-carbazole (0.15 g, 0.3 mmol) was dissolved in THF (5 mL) and a solution of KOH (0.068 g, 1.2 mmol) in water (5 mL) was added followed by EtOH (2 mL). The reaction mixture was heated at 60° C. for 6 h, diluted with water (10 mL) and extracted into EtOAc (2×50 mL). The combined organic extracts were dried over Na₂SO₄ and concentrated under reduced pressure to give the crude residue which was purified by column chromatography [EtOAc-hexane (1:4) as eluant] to provide the title compound (0.02 g, 20%). ¹H NMR (500 MHz, CDCl₃, δ in ppm) (mixture of two diastereomers) 8.35 (br s, 1H), 8.28 (br s, 1H), 7.26 (d, J=8.5 Hz, 2H), 7.19 (d, J=8 Hz, 2H), 3.26-2.98 (m, 4H), 2.51 (s, 1H), 2.46-2.42 (m, 1H), 2.35 (s, 1H), 2.26 (m, 1H), 2.12-1.97 (m, 3H), 1.84-1.78 (m, 1H), 1.21-1.18 (m, 5H).

Example 24

5,6,7-Trichloro-1-(trifluoromethyl)-2,3,4,9-tetrahydro-1H-carbazol-1-ol

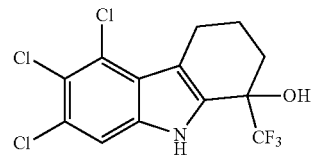 [SMILES: OC1(C(F)(F)F)CCCc2c1[nH]c1cc(Cl)c(Cl)c(Cl)c21]

Intermediate 24a

2-Oxocyclohexanecarboxylic acid

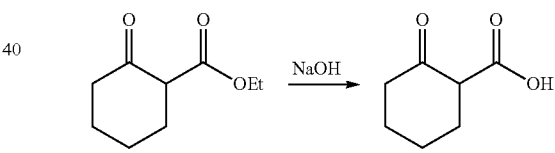

Ethyl 2-oxocyclohexanecarboxylate (2 g, 11.7 mmol) was dissolved in water (2 mL), cooled to 0° C. and 5N aqueous .NaOH (5 mL) was added, cooled to room temperature and stirred for 12 h. The reaction mixture was cooled to 0° C., acidified with conc. (pH=2) and used in the next step without any purification.

Intermediate 24b 2-(2-(3,4,5-Trichlorophenyl)hydrazono)cyclohexanone

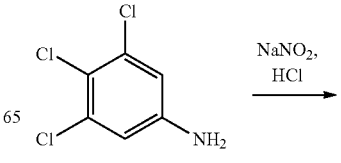

-continued

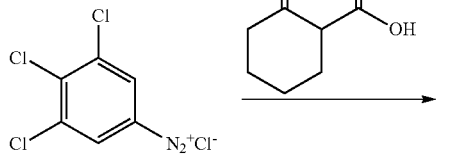

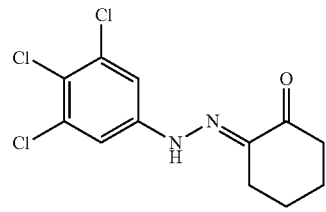

3,4,5-Trichloroaniline (1.6 g, 11.2 mmol) was dissolved in water (4 mL), cooled to 0° C., conc. HCl (1.5 ml) followed by a solution of NaNO$_2$ (0.7 g, 11.2 mmol) in water (4 mL), was added dropwise and the resulting mixture was stirred for 30 min. followed by the addition of a solution of 2-oxocyclohexanecarboxylic acid. The reaction mixture was warmed to room temperature and stirred for 1 h during which time a solid precipitated out which was filtered and air dried to give the title compound (1.0 g, 29%). $^1$H NMR (500 MHz, CDCl$_3$, δ in ppm) 13.5 (bs, 1H), 7.26 (s, 2H), 2.70 (s, 2H), 2.53 (s, 2H), 1.87 (s, 4H).

Intermediate 24c 5,6,7-Trichloro-2,3,4,9-tetrahydro-1H-carbazol-1-one

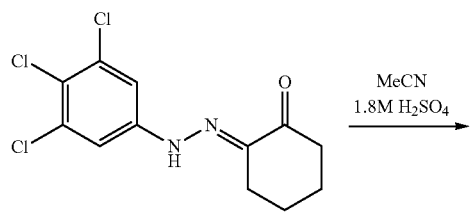

2-(2-(3,4,5-Trichlorophenyl)hydrazono)cyclohexanone (1 g, 3.2 mmol) was dissolved in MeCN (10 mL) and aqueous H$_2$SO$_4$ (0.5 mL, 1.8M solution) was added. The reaction mixture was heated to 80° C. for 6 h, basified with saturated Na$_2$CO$_3$ and extracted with EtOAc (2×100 mL). The combined organic extracts were dried over Na$_2$SO$_4$ and concentrated under reduced pressure to give the crude material which was purified by silica gel column chromatography [EtOAc-hexane (1:9) as eluant] to give the title compound (0.15 g, 16%). $^1$H NMR (500 MHz, DMSO-d$_6$, δ in ppm) 12.3 (bs, 1H), 7.58 (s, 1H), 3.24 (t, J=12.0 Hz, 2H), 2.59 (t, J=13.0 Hz, 2H), 2.19 (m, 2H).

Intermediate 24d 5,6,7-Trichloro-1-(trifluoromethyl)-1-(trimethylsilyloxy)-2,3,4,9-tetrahydro-1H-carbazole

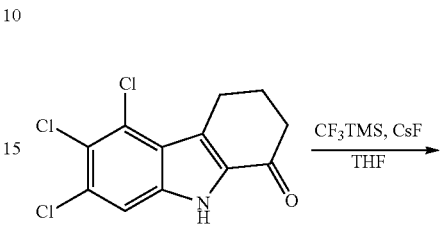

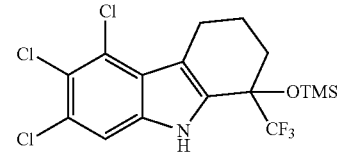

5,6,7-Trichloro-2,3,4,9-tetrahydro-1H-carbazol-1-one (0.15 g, 0.52 mmol) was dissolved in dry THF (5 mL), cooled to 0° C., and CsF (0.217 g, 1.43 mmol) followed by CF$_3$TMS (0.7 mL, 4.7 mmol) were added. The reaction mixture was warmed to room temperature and stirred for 1 h, quenched with saturated NH$_4$Cl and extracted with EtOAc (3×20 mL). The combined organic extracts were dried over Na$_2$SO$_4$ and concentrated under vacuum to give the crude title compound (0.11 g) which was used in the next step without any purification.

Example 24

5,6,7-Trichloro-1-(trifluoromethyl)-2,3,4,9-tetrahydro-1H-carbazol-1-ol

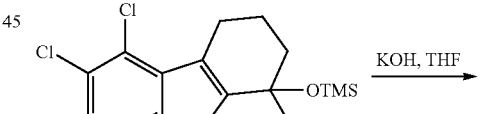

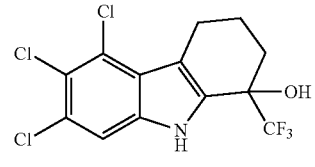

5,6,7-Trichloro-1-(trifluoromethyl)-1-(trimethylsilyloxy)-2,3,4,9-tetrahydro-1H-carbazole (0.11 g, 0.25 mmol) was dissolved in THF (5 mL) and a solution of KOH (0.050 g, 1 mmol) in water (5 mL) was added. The reaction mixture was stirred at room temperature for 1 h, diluted with water (10 mL) and extracted with EtOAc (2×50 mL). The combined organic extracts were dried over Na$_2$SO$_4$, concentrated under reduced pressure. The crude residue was purified by silica gel column chromatography [EtOAc-hexane (1:9) as eluant] to furnish the title compound (0.09 g, 44%). $^1$H NMR (500

MHz, CDCl$_3$, δ in ppm) 8.28 (bs, 1H), 7.42 (s, 1H), 3.29-3.23 (m, 1H), 3.02-2.95 (m, 1H), 2.44 (s, 1H), 2.26-2.22 (m, 1H), 2.09-1.98 (m, 3H).

Example 25

7,8-Dichloro-1-(trifluoromethyl)-2,3,4,9-tetrahydro-1H-carbazol-1-ol

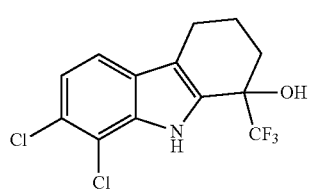 [SMILES: OC1(C(F)(F)F)CCCc2c1[nH]c1c(Cl)c(Cl)ccc21]

Intermediate 25a

2-(2-(2,3-Dichlorophenyl)hydrazono)cyclohexanone

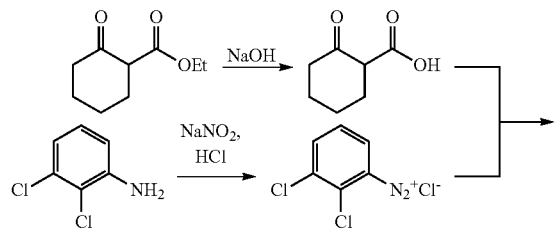

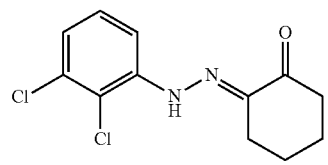

To ethyl 2-oxocyclohexanecarboxylate (2.0 g, 0.01 mmol), 5N NaOH (0.56 g, 0.014 mmol) dissolved in water (3.0 mL) was added at room temperature and stirred for 16 h. The reaction mixture was cooled to 0° C., conc. HCl (1.2 mL) was added and stirred for 45 min. to give 2-oxocyclohexanecarboxylic acid. In another setup, 2,3-dichloroaniline (1.8 g, 11.0 mmol), dissolved in H$_2$O (10 mL) was cooled to 0° C., conc. HCl (6 mL) was added slowly and stirred for 20 min. NaNO$_2$ (0.77 g, 11.0 mmol) in water (5.0 mL) was added and stirred at 0° C. for 30 min., filtered, the filtrate was cooled to 0° C. and 2-oxocyclohexanecarboxylic acid (prepared above) (1.6 g, 11.6 mmol) was added dropwise. The reaction mixture was warmed to room temperature and stirred for 30 min. during which time a yellow solid was precipitated. The solid was filtered and air dried to give the title compound as a yellow solid (1.7 g, 56%). $^1$H NMR (200 MHz, CDCl$_3$, δ in ppm) 13.87 (bs, 1H), 7.65 (dd, J=8.4, 1.8 Hz, 1H), 7.26-7.04 (m, 2H), 2.77-2.71 (m, 2H), 2.61-2.54 (m, 2H), 1.91-1.85 (m, 4H).

Intermediate 25b

7,8-Dichloro-2,3,4,9-tetrahydro-1H-carbazol-1-one

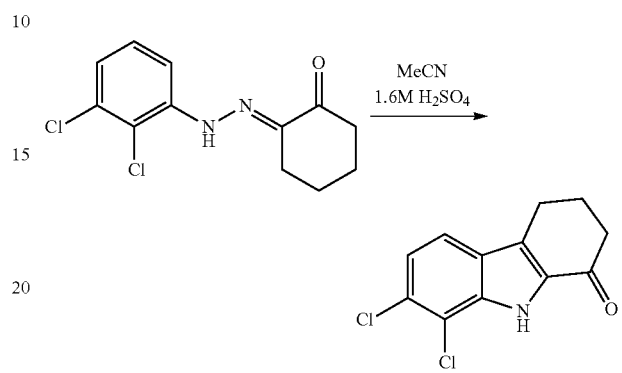

To a solution of 2-(2-(2,3-dichlorophenyl)hydrazono)cyclohexanone (1.6 g, 5.9 mmol) in MeCN (10 mL), H$_2$SO$_4$ (0.6 mL, 0.01 mmol, 1.6M solution) was added and the reaction mixture was stirred at 80° C. for 16 h, cooled to room temperature, basified with NaHCO$_3$ and extracted with EtOAc (2×20 mL). The combined organic extracts were dried over Na$_2$SO$_4$ and concentrated in vacuo to give the crude compound which was purified by silica gel chromatography [EtOAc-hexane (1:4) as eluant] to provide the title compound as a solid (0.90 g, 60%). $^1$H NMR (200 MHz, DMSO-d$_6$, δ in ppm) 12.13 (bs, 1H), 7.72 (d, J=8.8 Hz, 1H), 7.31 (d, J=8.8 Hz, 1H), 2.99 (t, J=8.4 Hz, 2H), 2.62-2.2.56 (m, 2H), 2.21-2.12 (m, 2H).

Example 25

7,8-Dichloro-1-(trifluoromethyl)-2,3,4,9-tetrahydro-1H-carbazol-1-ol

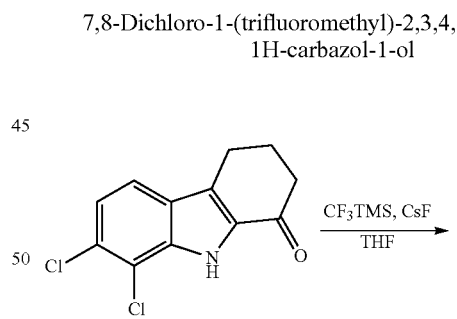

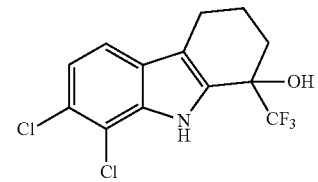

7,8-Dichloro-2,3,4,9-tetrahydro-1H-carbazol-1-one (0.2 g, 0.78 mmol) was dissolved in anhydrous THF (5 mL), cooled to 0° C., and CF$_3$TMS (1.2 mL, 8.7 mmol) followed by CsF (0.36 mg, 2.3 mmol) were added and stirred for 30 min. at 0° C. The reaction mixture was slowly warmed to room temperature and stirred for an additional 2 h, quenched with saturated NH$_4$Cl and extracted with EtOAc (3×20 mL). The combined organic extracts were dried over Na$_2$SO$_4$ and concentrated in vacuo to give the crude compound which was purified by column chromatography [EtOAc-hexane (1:4) as eluant] to provide the title compound as a yellow syrup (0.05 g, 19%). $^1$H NMR (500 MHz, CDCl$_3$, δ in ppm) 8.32 (bs, 1H), 7.38 (d, J=8.5 Hz, 1H), 7.21 (d, J=8.5 Hz, 1H), 2.85-2.81 (m, 1H), 2.73-2.70 (m, 1H), 2.68 (s, 1H), 2.29-2.24 (m, 1H), 2.13-2.11 (m, 2H), 2.03-2.01 (m, 1H).

Example 26

6,7-Dichloro-2-methyl-4-(trifluoromethyl)-2,3,4,9-tetrahydro-1H-carbazol-1-ol

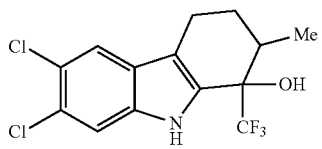 [SMILES: CC1CCc2c([nH]c3cc(Cl)c(Cl)cc23)C1(O)C(F)(F)F]

Intermediate 26a 6,7-Dichloro-2-methyl-9-tosyl-2,3,4,9-tetrahydro-1H-carbazol-1-one

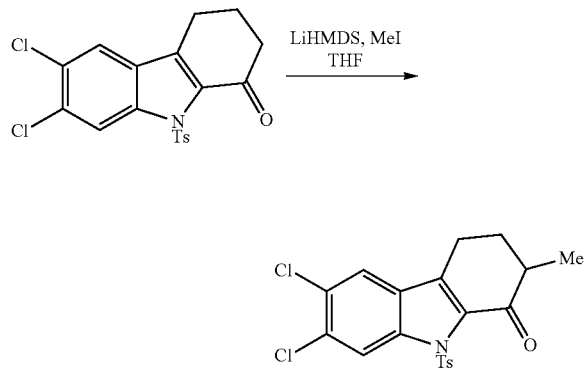

6,7-Dichloro-9-tosyl-2,3,4,9-tetrahydro-1H-carbazol-1-one 0.1 g, 0.024 mmol) was dissolved in dry THF, cooled to −78° C. and LiHMDS (0.6 mL, 0.61 mmol) was added dropwise. The reaction mixture was slowly warmed to 0° C. and stirred for an additional 30 min. The reaction mixture was cooled to −78° C. and MeI (0.040 mL, 0.61 mmol) was added slowly, warmed to room temperature and stirred for 4 h. Saturated NH$_4$Cl (10 mL) was added to the reaction mixture and extracted with EtOAc (2×50 mL). The combined organic extracts were dried over Na$_2$SO$_4$ and concentrated under reduced pressure. The crude residue was purified by column chromatography [EtOAc-hexane (1:9) as eluant] to obtain the title compound (0.04 g, 40%). $^1$H NMR (500 MHz, CDCl$_3$, δ in ppm) 8.49 (s, 1H), 8.03 (d, J=8.0 Hz, 2H), 7.67 (s, 1H), 7.32 (d, J=8.0 Hz, 2H), 2.98-2.85 (m, 2H), 2.71-2.66 (m, 1H), 2.43 (s, 3H), 2.27-2.23 (m, 1H), 1.96-1.89 (m, 1H), 1.25-1.17 (m, 3H).

Intermediate 26b 6,7-Dichloro-2-methyl-9-tosyl-4-(trifluoromethyl)-1-(trimethylsilyloxy)-2,3,4,9-tetrahydro-1H-carbazole

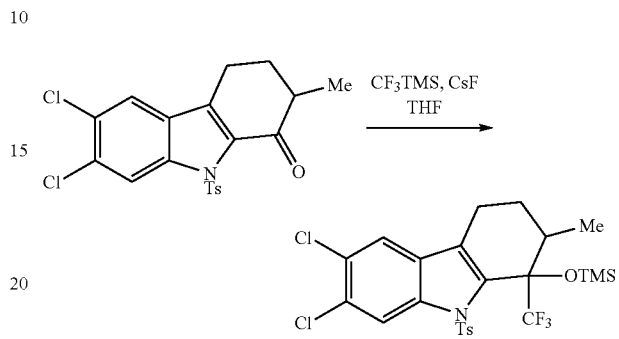

6,7-Dichloro-2-methyl-9-tosyl-2,3,4,9-tetrahydro-1H-carbazol-1-one (0.12 g, 0.28 mmol) was dissolved in dry THF (10 mL), cooled to 0° C. and CsF (0.13 g, 0.85 mmol) followed by CF$_3$TMS (0.45 mL, 2.8 mmol) were added. The reaction mixture was stirred at 0° C. for 1 h, quenched with saturated NH$_4$Cl and extracted with EtOAc (3×20 mL). The combined organic extracts were dried over Na$_2$SO$_4$ and concentrated in vacuo to give the crude title compound (0.11 g) which was used in the next step without purification.

Example 26

6,7-Dichloro-2-methyl-1-(trifluoromethyl)-2,3,4,9-tetrahydro-1H-carbazol-1-ol

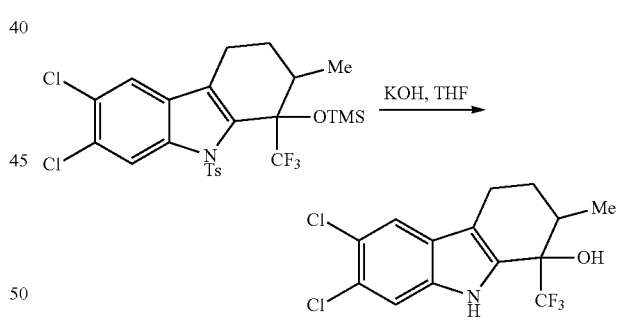

6,7-Dichloro-2-methyl-9-tosyl-1-(trifluoromethyl)-1-(trimethylsilyloxy)-2,3,4,9-tetrahydro-1H-carbazole (0.13 g, 0.26 mmol) was dissolved in THF (10 mL) and KOH (0.070 g, 1 mmol) in water (10 mL) was added followed by EtOH (3 mL). The reaction mixture was heated to 60° C. for 4 h, diluted with water (10 mL) and extracted with EtOAc (2×50 mL). The combined organic extracts were dried over Na$_2$SO$_4$ and concentrated under reduced pressure. The crude material was purified by column chromatography [EtOAc-hexane (1:4) as eluant] to give the title compound (0.025 g, 28%) $^1$H NMR (500 MHz, CDCl$_3$, δ in ppm) (mixture of two diastereomers) 8.22 (br s, 1H), 8.15 (bs, 1H), 7.60 (s, 1H), 7.47 (s, 1H), 2.82-2.63 (m, 2H), 2.51 (s, 1H), 2.46-2.43 (m, 1H), 2.33 (s, 1H), 2.28 (s, 1H), 2.14-2.10 (m, 2H), 2.03-1.98 (m, 1H), 1.82-1.79 (m, 1H), 1.22-1.20 (m, 3H).

Example 27

6,7-Dichloro-3-(trifluoromethyl)-1,2,3,4-tetrahydro-cyclopenta[b]indol-3-ol

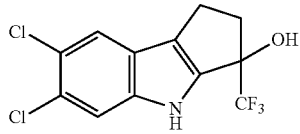 [SMILES: OC1(C(F)(F)F)CCc2c1[nH]c1cc(Cl)c(Cl)cc21]

Intermediate 27a 2-(2-(3,4-Dichlorophenyl)hydrazono)cyclopentanone

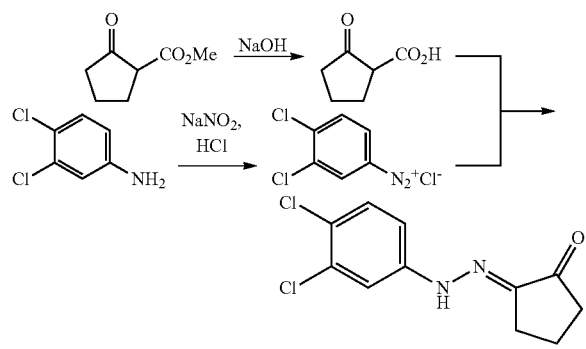

To methyl 2-oxocyclopentanecarboxylate (5 g, 35.1 mmol) in H₂O (7.5 mL), NaOH (1.5 g) was added. The reaction mixture was stirred at room temperature for 40 h, then cooled to 0° C. and conc. HCl (3 mL) was added, then stirred for an additional 30 min. at 0° C. to give 2-oxocyclopentanecarboxylic acid (4.5 g, crude). In another set up, 3,4-dichloroaniline (5.5 g, 33.9 mmol) was dissolved in H₂O (22 mL), cooled to 0° C. and conc. HCl (8.3 mL) was added and stirred for 20 min. while maintaining the temperature at 0° C. NaNO₂ (2.3 g, 33.9 mmol) in water was added to the reaction mixture and stirred at 0° C. for another 30 min. The reaction mixture was filtered and to the filtrate 2-oxocyclopentanecarboxylic acid (4.5 g, crude) (prepared above) was added slowly. The reaction mixture was slowly warmed to room temperature and stirred for 1 h during which time a solid precipitated out which was filtered to provide the title compound as a yellow solid (5 g, 58%). ¹H NMR (200 MHz, CDCl₃, δ in ppm) 7.59 (bs, 1H), 7.40-7.30 (m, 2H), 7.09-6.94 (m, 1H), 2.80 (t, J=7.4 Hz, 1H), 2.68 (t, J=7.4 Hz, 1H), 2.55-2.45 (m, 2H), 2.24-2.06 (m, 2H).

Intermediate 27b 6,7-Dichloro-1,2-dihydrocyclopenta[b]indol-3(4H)-one and 7,8-dichloro-1,2-dihydrocyclopenta[b]indol-3(4H)-one

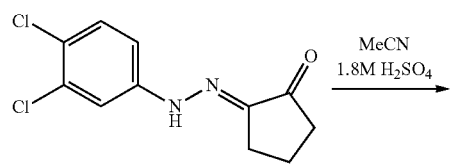

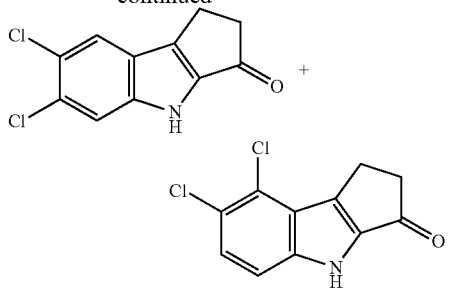

2-(2-(3,4-Dichlorophenyl)hydrazono)cyclopentanone (1 g, 3.9 mmol) was dissolved in MeCN (9 mL) and H₂SO₄ (1.14 g, 11.7 mmol, 1.8M solution in H₂O) was added slowly then heated to 80° C. for 12 h. After the reaction was complete, the reaction mixture was cooled to room temperature, diluted with water (50 mL), basified with saturated aqueous NaHCO₃ (pH-8) and extracted with EtOAc (3×50 mL). The combined organic extracts were dried over Na₂SO₄ and concentrated in vacuo to give the crude compound which was purified by silica gel chromatography [EtOAc-hexane (1:9) as eluant] to provide title compound as a mixture of regioisomers (1:3) (200 mg, 21%). ¹H NMR (200 MHz, DMSO-d₆, δ in ppm) (mixture of regioisomers) 12.19 (bs, ¾H), 11.99 (bs, ¼H), 8.08 (s, ¼H), 7.66 (s, ¼H), 7.51 (d, J=8.8 Hz, ¾H), 7.43 (d, J=8.8 Hz, ¾H), 3.22-3.17 (m, 3/2H), 3.04-2.99 (m, ½H), 2.93-2.89 (m, 2H).

Intermediate 27c tert-Butyl 6,7-dichloro-3-oxo-2,3-dihydrocyclopenta[b]indole-4(1H)-carboxylate and tert-butyl 7,8-dichloro-3-oxo-2,3-dihydrocyclopenta[b]indole-4(1H)-carboxylate

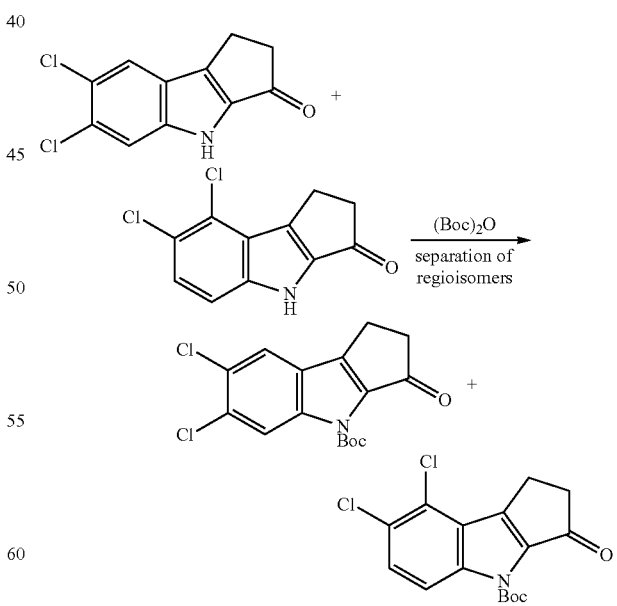

A mixture of 6,7-dichloro-1,2-dihydrocyclopenta[b]indol-3(4H)-one and 7,8-dichloro-1,2-dihydrocyclopenta[b]indol-3(4H)-one (0.2 g, 0.8 mmol) were dissolved in THF (5 mL), cooled to 0° C. and DMAP (0.14 g, 1.2 mmol) followed by Boc anhydride (0.21 mL, 0.9 mmol) were added. The reaction mixture was stirred at 0° C. for 1 h, diluted with water (50 mL) and extracted with EtOAc (3×20 mL). The combined organic extracts were dried over Na₂SO₄ and concentrated in vacuo to give the crude compound. The mixture of regioisomers were separate by column chromatography using EtOAc-hexane (1:49) as eluant to provide tert-butyl 7,8-dichloro-3-oxo-2,3-dihydrocyclopenta[b]indole-4(1H)-carboxylate (120 mg) followed by EtOAc-hexane (1:19) as eluant to give tert-Butyl 6,7-dichloro-3-oxo-2,3-dihydrocyclopenta[b]indole-4(1H)-carboxylate both as off-white solids (80 mg, combined yield of 71%). ¹H NMR (200 MHz, CDCl₃, δ in ppm) (tert-butyl 7,8-dichloro-3-oxo-2,3-dihydrocyclopenta[b]indole-4(1H)-carboxylate) 8.19 (d, J=9.0 Hz, 1H), 7.52 (d, J=9.0 Hz, 1H), 3.28-3.24 (m, 2H), 3.04-2.99 (m, 2H), 8.14 (s, 9H). ¹H NMR (200 MHz, CDCl₃, δ in ppm) (tert-butyl 6,7-dichloro-3-oxo-2,3-dihydrocyclopenta[b]indole-4(1H)-carboxylate) 8.49 (s, 1H), 7.75 (s, 1H), 3.02-3.02 (m, 4H), 1.69 (s, 9H).

Intermediate 27d 6,7-Dichloro-1,2-dihydrocyclopenta[b]indol-3(4H)-one

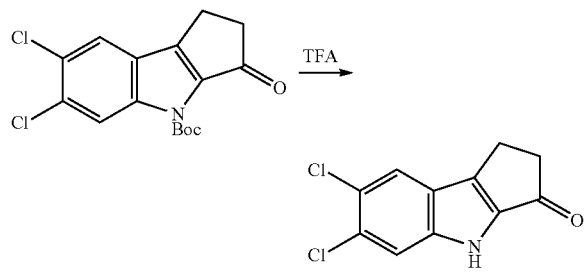

To a solution of tert-butyl 6,7-dichloro-3-oxo-2,3-dihydrocyclopenta[b]indole-4(1H)-carboxylate (0.34 g, 1.0 mmol) in CH₂Cl₂ (10 mL), cooled to 0° C., TFA (1 mL) was added. The reaction mixture was slowly warmed to room temperature and stirred for 90 min., quenched with saturated NaHCO₃ (pH-8) and extracted with DCM (3×100 mL). The combined organic extracts were dried over Na₂SO₄ and concentrated in vacuo to give the crude compound which was purified by washing with 5% EtOAc-hexane (3×20 mL) to provide the title compound (200 mg, 83%). ¹H NMR (500 MHz, DMSO-d₆, δ in ppm) 11.96 (s, 1H), 8.06 (s, 1H), 7.65 (s, 1H), 3.03 (t, J=3.5 Hz, 2H), 2.92 (t, J=4.0 Hz, 2H).

Intermediate 27e 6,7-Dichloro-4-tosyl-1,2-dihydrocyclopenta[b]indol-3(4H)-one

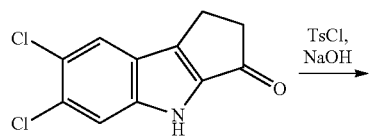

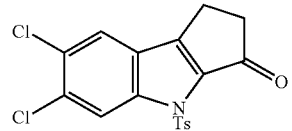

To a solution of 6,7-dichloro-1,2-dihydrocyclopenta[b]indol-3(4H)-one (0.25 g, 1.0 mmol) in DCM (30 mL), cooled to 0° C., 5N NaOH (3 mL) followed by benzyl triethyl ammonium chloride (50 mg) were added. The reaction mixture was stirred at 0° C. for 10 min and p-TsCl (0.59 g, 3.1 mmol) was added. The reaction mixture was warmed to room temperature, stirred for 5 h, diluted with water (20 mL) and extracted with DCM (3×30 mL). The combined organic extracts were dried over Na₂SO₄ and concentrated in vacuo to give the crude compound which was purified by washing with 50% EtOAc-hexane (2×20 mL) to provide the title compound (330 mg, 80%). ¹H NMR (500 MHz, CDCl₃, δ in ppm) 8.50 (s, 1H), 8.03 (d, J=8.0 Hz, 2H), 7.73 (s, 1H), 7.29 (d, J=8.5 Hz, 2H), 3.00 (m, 2H), 2.96 (m, 2H), 2.38 (s, 3H).

Intermediate 27f 6,7-Dichloro-4-tosyl-3-(trifluoromethyl)-3-(trimethylsilyloxy)-1,2,3,4-tetrahydrocyclopenta[b]indole

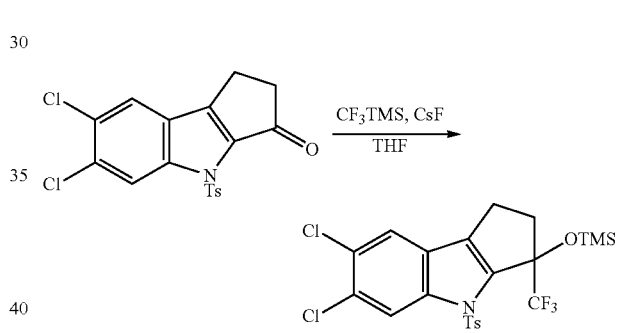

To a suspension of 6,7-dichloro-4-tosyl-1,2-dihydrocyclopenta[b]indol-3(4H)-one (0.15 g, 0.3 mmol) in anhydrous THF (10 mL), cooled to 0° C., CF₃TMS (0.6 mL, 3.8 mmol) and CsF (0.11 g, 0.7 mmol) were added. The reaction mixture was stirred at 0° C. for 20 min., quenched with saturated NH₄Cl (20 mL) and extracted with EtOAc (3×10 mL). The combined organic extracts were dried over Na₂SO₄ and concentrated in vacuo to provide the crude compound (200 mg, crude) which was used immediately in the next step without purification.

Example 27

6,7-Dichloro-3-(trifluoromethyl)-1,2,3,4-tetrahydrocyclopenta[b]indol-3-ol

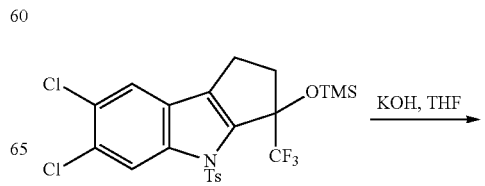

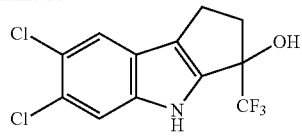

6,7-Dichloro-4-tosyl-3-(trifluoromethyl)-3-(trimethylsilyloxy)-1,2,3,4-tetrahydrocyclopenta[b]indole (0.2 g, 0.37 mmol) was dissolved in THF (10 mL) and KOH (104 mg, 1.8 mmol), in H$_2$O (10 mL), was added and the resulting mixture was refluxed for 18 h. The reaction mixture was diluted with water (10 mL) and extracted with EtOAc (3×20 mL). The combined organic extracts were dried over Na$_2$SO$_4$ and concentrated in vacuo to give the crude compound which was purified by column chromatography [EtOAc-hexane (3:17) as eluant] to afford the title compound (58 mg, 52%). $^1$H NMR (500 MHz, CDCl$_3$, δ in ppm) 8.05 (bs, 1H), 7.62 (s, 1H), 7.49 (s, 1H), 3.12-3.07 (m, 1H), 3.04-2.99 (m, 1H), 2.91-2.86 (m, 1H), 2.57-2.55 (m, 1H), 2.51 (s, 1H).

Example 28

6-Chloro-8-fluoro-1-(trifluoromethyl)-2,3,4,9-tetrahydro-1H-carbazol-1-ol

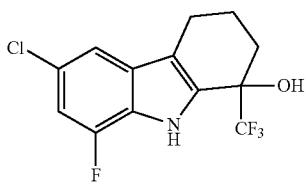

Intermediate 28a 2-(2-(4-Chloro-2-fluorophenyl)hydrazono)cyclohexanone

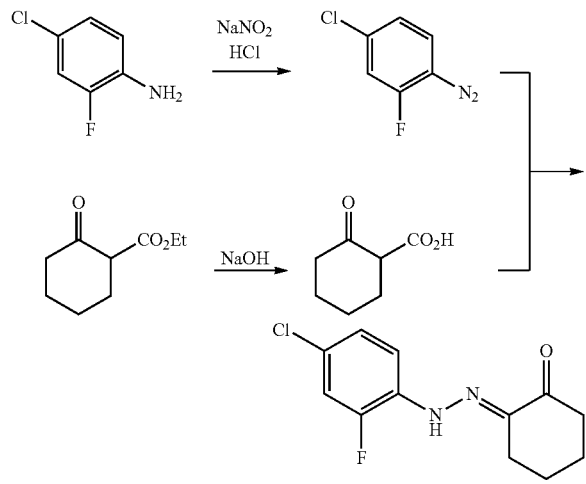

To 4-chloro-2-fluoroaniline (2.7 g, 19.0 mmol) in H$_2$O (12 mL), cooled to 0° C., conc. HCl (4.5 mL) was added and stirred for 10 min. NaNO$_2$ (1.3 g, 18.8 mmol), dissolved in water (13 mL), was added slowly to the reaction mixture and stirred at 0° C. for an additional 30 min., the solids were filtered to give the diazonium salt. In another set up, to ethyl 2-oxocyclohexanecarboxylate (3 g, 19.3 mmol) in H$_2$O (10 mL), 5N NaOH (5 mL) was added. The reaction mixture was stirred at room temperature for 24 h and washed with EtOAc (15 mL). The aqueous layer was separated, cooled to 0° C. and conc. HCl (5 mL) was added dropwise to obtain 2-oxocyclohexanecarboxylic acid (2.7 g, crude). 2-oxocyclohexanecarboxylic acid (2.7 g, 19.0 mmol) and diazonium salt (prepared above) were mixed together at 0° C. and the reaction mixture was slowly warmed to room temperature and stirred for 1 h during which time a solid precipitated out which was filtered, washed with hexane (20 mL) and air dried to give the title compound as a yellow solid (2.2 g, 45%). $^1$H NMR (200 MHz, CDCl$_3$, δ in ppm) 13.64 (bs, 1H), 7.684 (t, J=8.8 Hz, 1H), 7.10 (t, J=10.0 Hz, 2H), 2.74-2.67 (m, 2H), 2.56-2.50 (m, 2H), 1.90-1.83 (m, 4H).

Intermediate 28b

6-Chloro-8-fluoro-2,3,4,9-tetrahydro-1H-carbazol-1-one

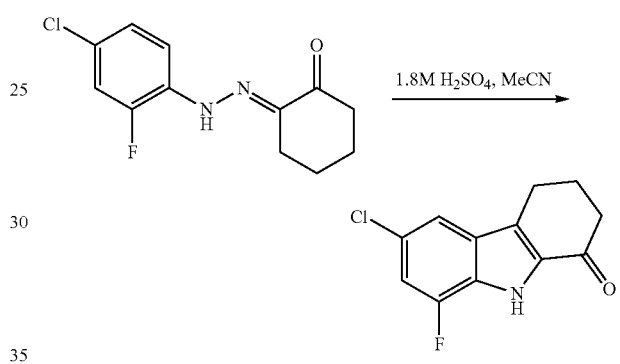

To a solution of 2-(2-(4-chloro-2-fluorophenyl)hydrazono)cyclohexanone (0.5 g, 1.9 mmol) in MeCN (5 mL), H$_2$SO$_4$ (0.31 mL, 5.9 mmol, 1.8M solution) was added slowly and the resulting mixture was heated to 80° C. for 12 h. The reaction mixture was cooled to room temperature, basified with saturated NaHCO$_3$ (pH-8) and extracted with EtOAc (2×30 mL). The combined organic extracts were dried over sodium Na$_2$SO$_4$ and concentrated in vacuo to give the crude compound which was purified by silica gel chromatography [EtOAc-hexane (1:9) as eluant] to provide the title compound (120 mg, 25%). $^1$H NMR (200 MHz, CDCl$_3$, δ in ppm): 8.96 (bs, 1H), 7.43 (d, J=1.0 Hz, 1H), 7.12 (dd, 1H, J=10.2, 1.60 Hz, 1H), 2.99 (t, J=5.8 Hz, 2H), 2.71 (t, J=6.0 Hz, 2H), 2.34-2.21 (m, 2H).

Example 28

6-Chloro-8-fluoro-1-(trifluoromethyl)-2,3,4,9-tetrahydro-1H-carbazol-1-ol

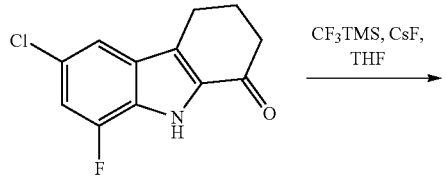

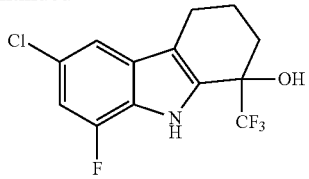 [SMILES: OC1(C(F)(F)F)CCCc2c1[nH]c1c(F)cc(Cl)cc21]

To a solution of 6-chloro-8-fluoro-2,3,4,9-tetrahydro-1H-carbazol-1-one (0.15 g, 0.63 mmol) in anhydrous THF (12 mL), cooled to 0° C., CF$_3$TMS (1 mL, 6.3 mmol) followed by CsF (0.28 g, 1.8 mmol) were added. The reaction mixture was stirred at 0° C. for 6 h, quenched with saturated NH$_4$Cl (10 mL) and extracted with EtOAc (2×15 mL). The combined organic extracts were dried over Na$_2$SO$_4$ and concentrated under reduced pressure to obtain the crude material which was purified by column chromatography [EtOAc-hexanes (3:22) as eluant] to give the title compound (0.016 g, 8%). $^1$H NMR (200 MHz, CDCl$_3$, δ in ppm) 8.35 (bs, 1H), 7.30 (s, 1H), 7.00 (d, J=4.2 Hz, 1H), 2.82-2.79 (m, 1H), 2.70-2.68 (m, 1H), 2.47 (s, 1H), 2.28-2.24 (m, 1H), 2.12-2.10 (m, 2H), 2.03-2.02 (m, 1H).

Example 29

7,8-Dichloro-3-(trifluoromethyl)-1,2,3,4-tetrahydrocyclopenta[b]indol-3-ol

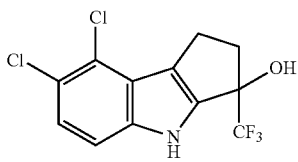 [SMILES: OC1(C(F)(F)F)CCc2c1[nH]c1ccc(Cl)c(Cl)c21]

Intermediate 29a 7,8-Dichloro-1,2-dihydrocyclopenta[b]indol-3(4H)-one

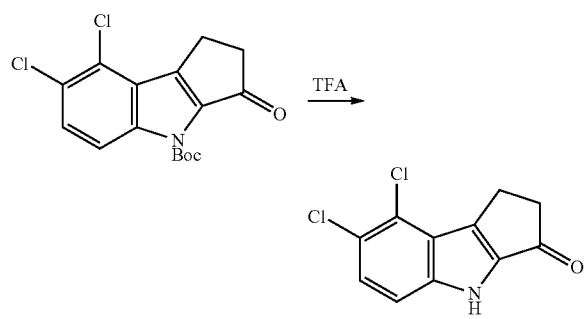

To a solution of tert-butyl 7,8-dichloro-3-oxo-2,3-dihydrocyclopenta[b]indole-4(1H)-carboxylate (intermediate 27c) (0.4 g, 1.1 mmol) in CH$_2$Cl$_2$ (10 mL), cooled to 0° C., TFA (1 mL) mL) was added. The reaction mixture was warmed to room temperature and stirred for 90 min., quenched with saturated NaHCO$_3$ (pH-8) and extracted with CH$_2$Cl$_2$ (3×100 mL). The combined organic extracts were dried over Na$_2$SO$_4$ and concentrated in vacuo to give the crude compound. The crude material was purified by washing with 5% EtOAc-hexane (3×20 mL) to provide the title compound (250 mg, 89%). $^1$H NMR (500 MHz, DMSO-d$_6$, δ in ppm) 12.16 (s, 1H), 7.48 (d, J=15.0 Hz, 1H), 7.42 (d, J=15.0 Hz, 1H), 3.19 (m, 2H), 2.92 (m, 2H).

Intermediate 29b 7,8-Dichloro-4-tosyl-1,2-dihydrocyclopenta[b]indol-3(4H)-one

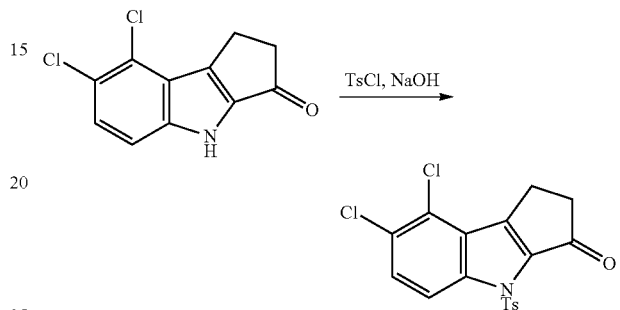

7,8-Dichloro-1,2-dihydrocyclopenta[b]indol-3(4H)-one (0.25 g, 1.0 mmol) was dissolved in DCM (30 mL), cooled to 0° C. and 5N NaOH (3 mL) followed by benzyl triethyl ammonium chloride (50 mg) were added. The reaction mixture was stirred at 0° C. for 10 min. and p-TsCl (0.59 g, 3.1 mmol) was added and stirred for 5 h at room temperature. The reaction mixture was diluted with water (50 mL) and extracted with CH$_2$Cl$_2$ (3×50 mL). The combined organic extracts were dried over Na$_2$SO$_4$ and concentrated in vacuo to give the crude compound which was purified by washing with 50% EtOAc-hexane (2×20 mL) and 50% DCM-hexane (3×20 mL) to provide the title compound (250 mg, 61%). $^1$H NMR (500 MHz, CDCl$_3$, δ in ppm) 8.22 (d, J=9.0 Hz, 1H), 8.02 (d, J=8.5 Hz, 2H), 7.57 (d, J=9.5 Hz, 1H), 7.28 (d, J=10.5 Hz, 2H), 3.22-3.21 (m, 2H), 2.99-2.97 (m, 2H), 2.38 (s, 3H).

Intermediate 29c 7,8-Dichloro-4-tosyl-3-(trifluoromethyl)-3-(trimethylsilyloxy)-1,2,3,4-tetrahydrocyclopenta[b]indole

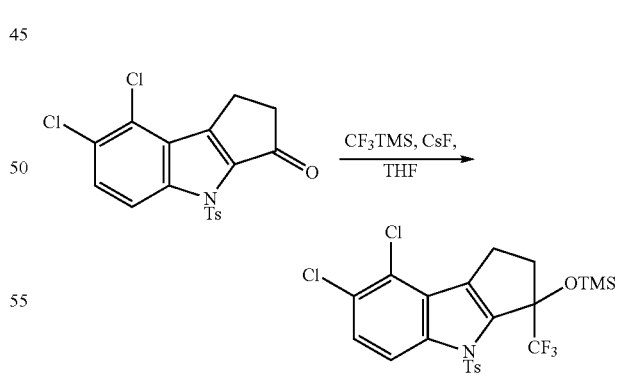

To a solution of 7,8-dichloro-4-tosyl-1,2-dihydrocyclopenta[b]indol-3(4H)-one (0.15 g, 0.3 mmol) in anhydrous THF (10 mL), cooled to 0° C., CF$_3$TMS (0.6 mL, 3.8 mmol) followed by CsF (0.11 g, 0.7 mmol) were added. The reaction mixture was stirred at 0° C. for 1 h, quenched with saturated NH$_4$Cl (20 mL) and extracted with EtOAc (3×20 mL). The combined organic extracts were dried over Na$_2$SO$_4$ and concentrated in vacuo to provide the crude compound (200 mg) which was used in the next step without purification.

Example 29

7,8-Dichloro-3-(trifluoromethyl)-1,2,3,4-tetrahydrocyclopenta[b]indol-3-ol

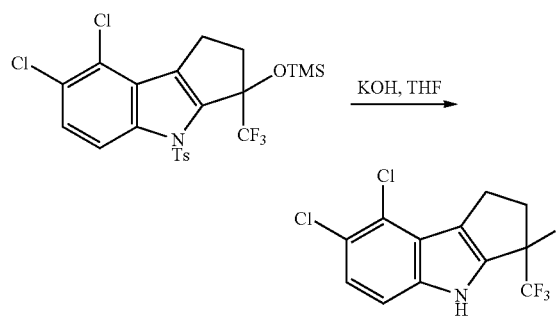

To 7,8-dichloro-4-tosyl-3-(trifluoromethyl)-3-(trimethylsilyloxy)-1,2,3,4-tetrahydrocyclopenta[b]indole (0.2 g, 0.3 mmol) in THF (10 mL), KOH (104 mg, 1.8 mmol) in H$_2$O (10 mL) was added and the resulting mixture was refluxed for 18 h. The reaction mixture was diluted with water (20 mL) and extracted with EtOAc (3×10 mL). The combined organic extracts were dried over Na$_2$SO$_4$ and concentrated in vacuo to give the crude compound which was purified by column chromatography (10% EtOAc-hexane) to afford the title compound as a white solid (58 mg, 53%). $^1$H NMR (500 MHz, DMSO-d$_6$, δ in ppm) 11.70 (s, 1H), 7.35 (d, 8.5 Hz, 1H), 7.28 (d, J=9.0 Hz, 1H), 6.90 (s, 1H), 3.12-3.07 (m, 1H), 2.97-2.88 (m, 2H), 2.88-2.50 (m, 1H).

Example 30

1-Hydroxy-1,8-bis(trifluoromethyl)-2,3,4,9-tetrahydro-1H-carbazole-6-carbonitrile

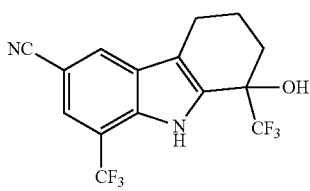 [SMILES: N#Cc1cc(C(F)(F)F)c2[nH]c3c(c2c1)CCCC3(O)C(F)(F)F]

Intermediate 30a

2-Oxocyclohexanecarboxylic acid

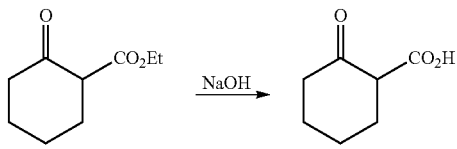 [SMILES: CCOC(=O)C1CCCCC1=O ; "NaOH" ; O=C(O)C1CCCCC1=O]

To ethyl 2-oxocyclohexanecarboxylate (3 g, 19.2 mmol) in H$_2$O (10 mL), 5N NaOH (4.5 mL) was added. The reaction mixture was stirred at room temperature for 12 h. The reaction mixture was washed with EtOAc (3×20 mL), the aqueous layer was cooled to 0° C., acidified with conc. HCl (5 mL) (pH-2) to give the crude acid (2.46 g) which was used in the next step without purification.

Intermediate 30b (2-(2-(4-Bromo-2-(trifluoromethyl)phenyl)hydrazono)cyclohexanone

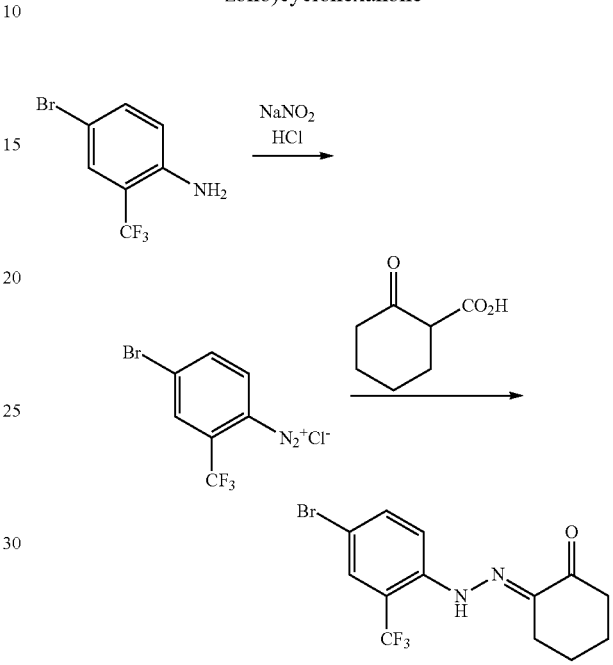

To 4-bromo-2-(trifluoromethyl)aniline (4.61 g, 19.21 mmol) in H$_2$O (24 mL), conc. HCl (4 mL) was added and stirred at 0° C. for 10 min. NaNO$_2$ (1.32 g, 19.21 mmol), dissolved in water (10 mL), was added to the reaction mixture and allowed to stir at 0° C. for 30 min. The solid obtained was filtered, the filtrate was cooled to 0° C. and 2-oxocyclohexanecarboxylic acid (2.46 g, 19.21 mmol) was added while maintaining the temperature at 0° C. The reaction mixture was slowly warmed to room temperature and stirred for an additional 1 h. The solid obtained was filtered and air dried to afford the title compound (2 g, 30%). $^1$H NMR (200 MHz, CDCl$_3$, δ in ppm) 14.05 (br s, 1H), 7.80-7.75 (d, J=8.8 Hz, 1H), 7.64-7.54 (m, 2H), 2.76-2.69 (m, 2H), 2.60-2.53 (m, 2H), 1.91-1.84 (m, 4H).

Intermediate 30c

6-Bromo-8-(trifluoromethyl)-2,3,4,9-tetrahydro-1H-carbazol-1-one

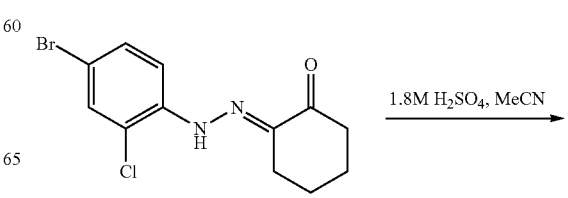

-continued

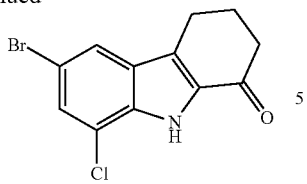

2-(2-(4-Bromo-2-(trifluoromethyl)phenyl)hydrazono)cyclohexanone (2 g, 5.73 mmol) was dissolved in MeCN (18 mL) and H$_2$SO$_4$ (1.68 g, 17.19 mmol) was added. The reaction mixture was heated to 80° C. for 32 h, cooled to room temperature, basified with saturated aqueous NaHCO$_3$ (pH-8) and extracted with EtOAc (2×30 mL). The combined organic extracts were dried over Na$_2$SO$_4$ and concentrated in vacuo to give the crude compound which was purified by silica gel chromatography [EtOAc-hexane (19:1) as eluant] to provide the title compound as a pale green solid (750 mg, 39%). $^1$H NMR (200 MHz, CDCl$_3$, δ in ppm) 9.0 (bs, 1H), 7.9 (s, 1H), 7.72 (d, 1H, J=0.8 Hz), 2.96 (t, J=12.0 Hz, 2H), 2.66 (t, J=12.8 Hz, 2H), 2.33-2.27 (m, 2H).

Intermediate 30d

1-Oxo-8-(trifluoromethyl)-2,3,4,9-tetrahydro-1H-carbazole-6-carbonitrile

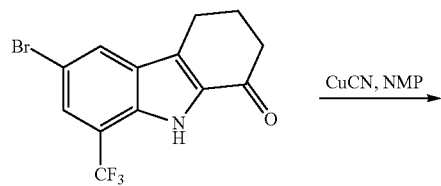

6-Bromo-8-(trifluoromethyl)-2,3,4,9-tetrahydro-1H-carbazol-1-one (600 mg, 1.8 mmol) and CuCN (480 mg, 5.4 mmol) were mixed together in NMP (6 mL) and stirred at 210° C. under N$_2$ atmosphere for 15 h. The reaction mixture was cooled to room temperature, diluted with water (20 mL) and filtered through a pad of Celite®. The aqueous layer was extracted with EtOAc (3×50 mL). The combined organic extracts were dried over Na$_2$SO$_4$ and concentrated in vacuo to obtain the crude material which was purified by washing with 10% EtOAc-hexane to afford the title compound as a pale brown solid (400 mg, 80%). $^1$H NMR (200 MHz, CDCl$_3$, δ in ppm) 9.26 (bs, 1H), 8.22 (s, 1H), 7.86-7.90 (m, 1H), 3.09 (t, J=12.0 Hz, 2H), 2.77-2.70 (m, 2H), 2.40-2.31 (m, 2H). IR cm−1 2240 (CN)

Intermediate 30e 1,8-bis(Trifluoromethyl)-1-(trimethylsilyloxy)-2,3,4,9-tetrahydro-1H-carbazole-6-carbonitrile

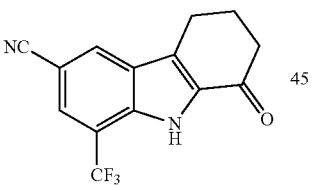

1-Oxo-8-(trifluoromethyl)-2,3,4,9-tetrahydro-1H-carbazole-6-carbonitrile (0.1 g, 0.35 mmol) was dissolved in anhydrous THF (5 mL), cooled to 0° C. and CF$_3$TMS (0.56 mL, 3.5 mmol) followed by CsF (0.2 g, 0.7 mmol) were added. The reaction mixture was stirred at 0° C. for 1 h, quenched with saturated aqueous NH$_4$Cl (20 mL) and extracted with EtOAc (3×10 mL). The combined organic extracts were dried over Na$_2$SO$_4$ and concentrated in vacuo to give the crude residue which was purified by silica gel chromatography [EtOAc-hexane (9:1) as eluant] to give the title compound (100 mg, 60%) which was used immediately in the next step without purification.

Example 30

1-Hydroxy-1,8-bis(trifluoromethyl)-2,3,4,9-tetrahydro-1H-carbazole-6-carbonitrile

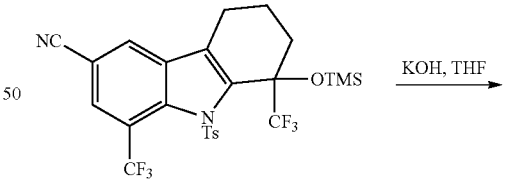

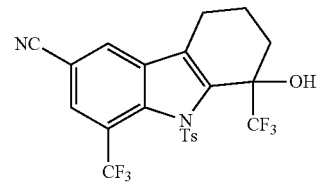

1,8-bis(Trifluoromethyl)-1-(trimethylsilyloxy)-2,3,4,9-tetrahydro-1H-carbazole-6-carbonitrile (100 mg, 0.23 mmol) was dissolved in THF (5 mL) and KOH (66 mg, 1.19 mmol), in H$_2$O (5 mL), was added. The reaction mixture was stirred at room temperature for 1 h, diluted with water (10 mL) and extracted with EtOAc (3×20 mL). The combined organic extracts were dried over Na$_2$SO$_4$ and concentrated in vacuo to give the crude compound which was purified by column chromatography [EtOAc-hexane (17:3) as eluant] to afford the title compound as a white solid (30 mg, 36.58%). $^1$H NMR (500 MHz, CDCl$_3$, δ in ppm) 8.75 (br s, 1H), 8.067 (s, 1H), 7.75 (s, 1H), 2.91-2.86 (m, 1H), 2.80-2.74 (m, 1H), 2.55 (s, 1H), 2.37-2.32 (m, 1H), 2.16-2.05 (m, 3H).

Example 31

6-Bromo-9H-carbazol-1-ol

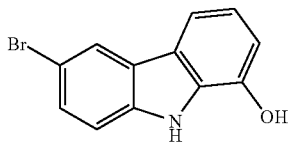 [SMILES: Oc1cccc2c1[nH]c1ccc(Br)cc12]

Intermediate 31a

6-Bromo-2,3,4,9-tetrahydro-1H-carbazol-1-one

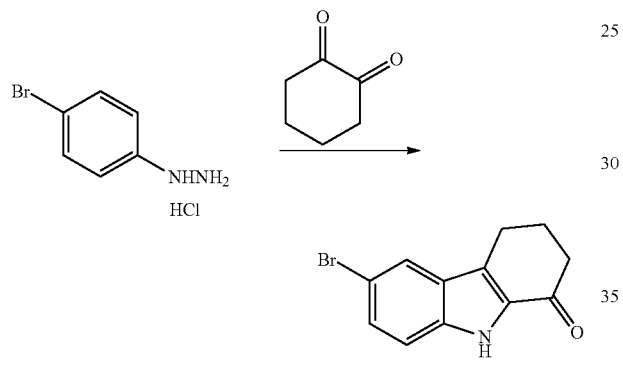

4-Bromophenyl hydrazine hydrochloride (0.3 g, 1.3 mmol) in MeOH (3 mL) was heated to 60° C. and 1,2-cyclohexanedione (0.16 g, 1.4 mmol), dissolved in AcOH (4 mL) and conc. HCl (1.5 mL) were added while maintaining the temperature at 60° C. After the addition was completed, the reaction mixture was cooled to room temperature and stirred for 12 h during time a solid precipitated out. The mixture was basified with aq NaHCO$_3$ and extracted with EtOAc (3×25 mL). The combined organic extracts were washed with water, dried over Na$_2$SO$_4$ and concentrated in vacuo to give the crude product which was purified by column chromatography to give the title compound as a pale yellow solid (0.080 g, 22%). $^1$H NMR (500 MHz, CDCl$_3$, δ in ppm) 8.8 (bs, 1H), 7.8 (s, 1H), 7.43 (dd, J=10.0, 2.0 Hz, 1H), 7.24 (d, J=9.5 Hz, 1H), 2.98 (t, J=8.0 Hz, 2H), 2.63 (t, 8.0 Hz, 2H), 2.24 (m, 2H).

Intermediate 31b 2,6-Dibromo-2,3,4,9-tetrahydro-1H-carbazol-1-one

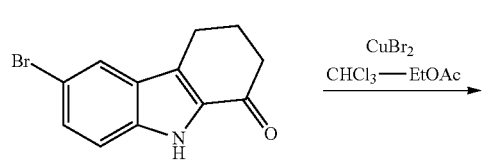

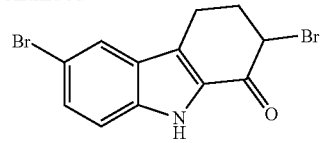

CuBr$_2$ (0.50 g, 2.26 mmol) in EtOAc (3 mL) was heated to 60° C. and 6-bromo-2,3,4,9-tetrahydro-1H-carbazol-1-one (0.3 g, 1.14 mmol) dissolved in CHCl$_3$ (5 mL) was added slowly while maintaining the temperature at 60° C. The reaction mixture was refluxed for 12 h, cooled to room temperature and filtered through a pad of Celite®. The filtrate was concentrated under reduced pressure and purified by column chromatography [EtOAc-hexane (3:17) as eluant] to give the title compound as a light brown solid (0.180 mg, 47%). $^1$H NMR (500 MHz, CDCl$_3$, δ in ppm) 8.9 (bs, 1H), 7.81 (s, 1H), 7.45 (dd, J=9.0, 2.0 Hz, 1H), 7.36 (d, J=8.5 Hz, 1H), 4.8 (s, 1H), 3.21-3.18 (m, 1H), 3.10-3.00 (m, 1H), 2.0 (s, 2H).

Example 31

6-Bromo-9H-carbazol-1-ol

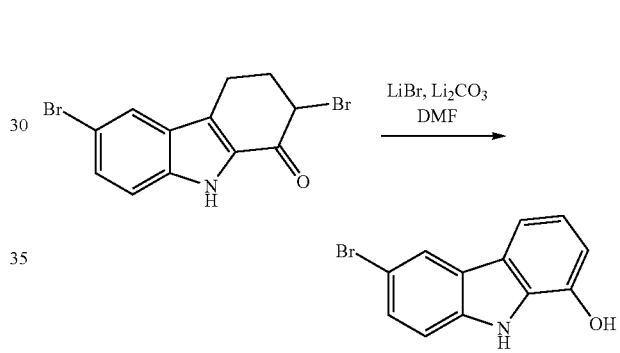

To a solution of 2,6-dibromo-2,3,4,9-tetrahydro-1H-carbazol-1-one (0.35 g, 1.02 mmol) in anhydrous DMF (10 mL), LiBr (0.097 g, 1.11 mmol) followed by Li$_2$CO$_3$ (0.082 g, 1.11 mmol) were added and the resulting mixture was heated at 150° C. for 4 h. The reaction mixture was poured into ice cold water and extracted with EtOAc (2×20 mL). The combined organic extracts were dried over Na$_2$SO$_4$, concentrated in vacuo and purified by column chromatography [EtOAc/hexane (3:17) as eluant] to give the title compound as a brown-colored solid (0.180 g, 69%). $^1$H NMR (500 MHz, CDCl$_3$, δ in ppm) 8.23 (bs, 1H), 8.17 (s, 1H), 7.61 (d, J=8.0 Hz, 1H), 7.50 (d, J=8.5 Hz, 1H), 7.32 (d, J=9.5 Hz, 1H), 7.08 (m, 1H), 6.80 (d, J=7.5 Hz, 1H), 5.01 (bs, 1H).

Example 32

8-Hydroxy-9H-carbazole-3-carbonitrile

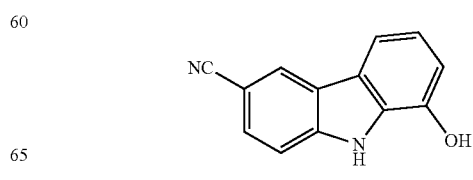

Intermediate 32a

2-Bromo-1-oxo-2,3,4,9-tetrahydro-1H-carbazole-6-carbonitrile

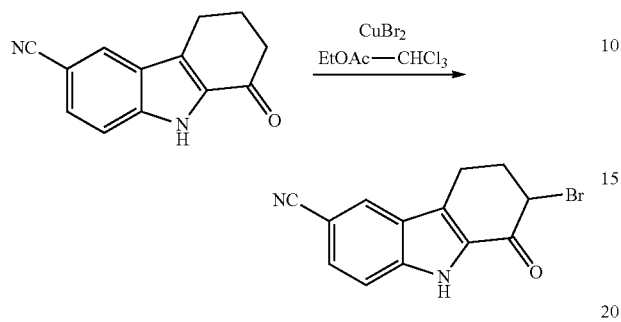

To a solution of CuBr$_2$ (0.38 g, 1.7 mmol) in EtOAc (2 mL), heated to 60° C., 1-oxo-2,3,4,9-tetrahydro-1H-carbazole-6-carbonitrile (intermediate 2a) (0.3 g, 1.4 mmol) dissolved in CHCl$_3$ (4 mL) was added dropwise. The reaction was continued at 60° C. for 12 h and then filtered through a pad of Celite®. The Celite® pad was washed with EtOAc (2×20 mL). The combined organic extracts were concentrated in vacuo to obtain the crude compound which was purified by silica gel chromatography [EtOAc-hexane (3:17) as eluant] to afford the title compound as a brown solid (0.2 g, 50%). $^1$H NMR (500 MHz, CDCl$_3$, δ in ppm) 9.20 (bs, 1H), 8.15 (s, 1H), 7.22 (d, J=12.5 Hz, 1H), 7.18 (d, J=12.5 Hz, 1H), 4.80-4.78 (m, 1H), 3.19-3.22 (m, 1H), 3.07-3.12 (m, 1H), 2.63 (2, 2H).

Example 32

8-Hydroxy-9H-carbazole-3-carbonitrile

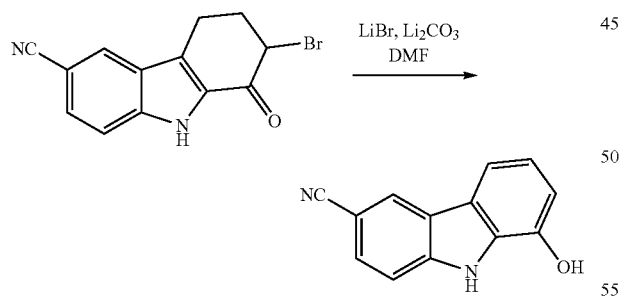

2-Bromo-1-oxo-2,3,4,9-tetrahydro-1H-carbazole-6-carbonitrile (0.1 g, 0.5 mmol) was dissolved in DMF (5 mL) and LiBr (49 mg, 0.5 mmol) followed by Li$_2$CO$_3$ (42 mg, 0.5 mmol) were added. The reaction mixture was heated to 150° C. for 3 h, poured into ice cold water and extracted with EtOAc (3×30 mL). The combined organic extracts were concentrated under reduced pressure to obtain the crude compound which was purified by column chromatography [EtOAc-hexane (3:17) as eluant] to furnish the title compound as a white solid (0.04 g, 40%). $^1$H NMR (500 MHz, CDCl$_3$, δ in ppm) 11.71 (s, 1H), 10.03 (s, 1H), 8.61 (s, 1H), 7.70-7.66 (m, 2H), 7.58 (d, J=8.0 Hz, 1H), 7.05 (d, J=7.5 Hz, 1H), 6.91 (d, J=7.5 Hz, 1H).

Example 33

5,6-Dichloro-9H-carbazol-1-ol

Intermediate 33a

2-Bromo-5,6-dichloro-2,3,4,9-tetrahydro-1H-carbazol-1-one

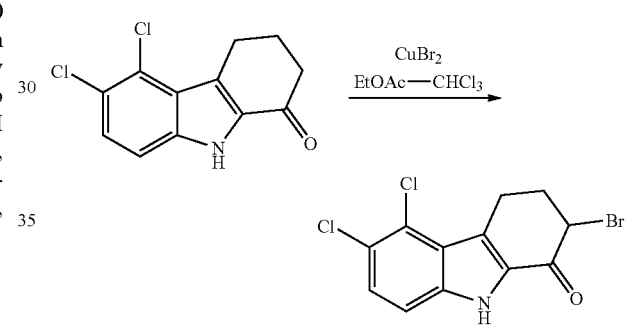

To a suspension of CuBr$_2$ (0.1 g, 0.47 mmol) in EtOAc (2 mL), heated to 60° C., 5,6-dichloro-2,3,4,9-tetrahydro-1H-carbazol-1-one (intermediate 5a) (0.1 g, 0.39 mmol) dissolved in CHCl$_3$ (3 mL) was added slowly. The reaction was continued at 60° C. for an additional 6 h. The reaction mixture was filtered through a Celite® bed and the filtrate was concentrated in vacuo to give the crude compound which was purified by silica gel chromatography [EtOAc-hexane (1:9) as eluant] to provide the title compound as a white solid (0.1 g, 83%). $^1$H NMR (500 MHz, CDCl$_3$, δ in ppm) 8.8 (bs, 1H), 7.80 (d, J=9.0 Hz, 1H), 7.40 (d, J=9.5 Hz, 1H), 4.70 (m, 1H), 3.20-3.0 (m, 2H), 2.68-2.2.60 (m, 2H).

Example 33

5,6-Dichloro-9H-carbazol-1-ol

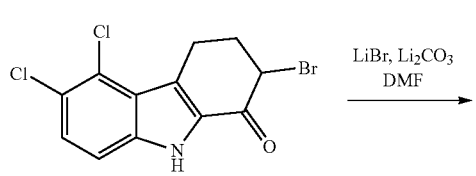

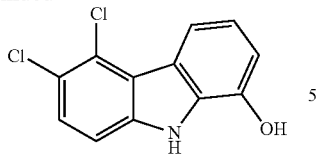

2-Bromo-5,6-dichloro-2,3,4,9-tetrahydro-1H-carbazol-1-one (0.1 g, 0.33 mmol) was dissolved in anhydrous DMF (4 mL) and LiBr (0.031 g, 0.35 mmol) followed by $Li_2CO_3$ (26 mg, 0.35 mmol) were added. The reaction mixture was heated to 150° C. for 30 min, then cooled to room temperature, poured into ice water and extracted with EtOAc (3×20 mL). The combined organic extracts were concentrated in vacuo to obtain the crude compound which was purified by column chromatography [EtOAc-hexane (1:9) as eluant] to give the title compound as an ash solid (0.04 g, 40%). $^1$H NMR (500 MHz, $CDCl_3$, δ in ppm) 8.38 (bs, 1H), 8.20 (d, J=9.0 Hz, 1H), 7.48 (d, J=8.5 Hz, 1H), 7.33 (d, J=9.0 Hz, 1H), 7.16 (m, 1H), 6.91 (d, J=8.0 Hz, 1H), 5.10 (bs, 1H).

Example 34

2-Bromo-6,7-dichloro-9H-carbazol-1-ol

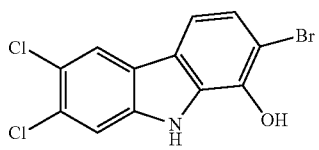 [SMILES: Oc1c(Br)ccc2c1[nH]c1cc(Cl)c(Cl)cc12]

Intermediate 34a 2,2-Bibromo-6,7-dichloro-2,3,4,9-tetrahydro-1H-carbazol-1-one

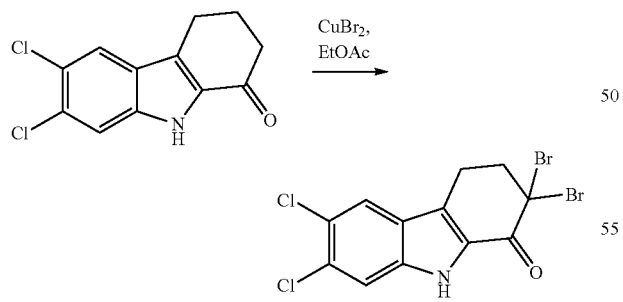

To a solution of 6,7-dichloro-2,3,4,9-tetrahydro-1H-carbazol-1-one (intermediate 1c) (0.2 g, 0.79 mmol) in EtOAc (4 mL), copper bromide (1.2 g, 5.38 mmol) was added. The reaction mixture was heated to 80° C. for 18 h and filtered through Celite®. The Celite® pad was washed with EtOAc (2×10 mL). The combined organic extracts were concentrated under reduced pressure to give the title compound as an off-white solid (0.13 g, 40%). $^1$H NMR (500 MHz, $CDCl_3$, δ in ppm): 8.82 (bs, 1H), 7.76 (s, 1H), 7.58 (s, 1H), 3.22 (t, J=6.0 Hz, 2H), 3.06 (t, J=5.0 Hz, 2H).

Example 34

2-Bromo-6,7-dichloro-9H-carbazol-1-ol

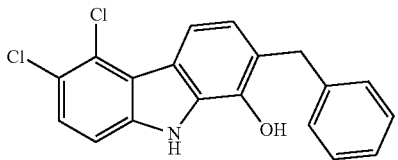 [SMILES: Oc1c(Cc2ccccc2)ccc2c1[nH]c1ccc(Cl)c(Cl)c12]

2,2-Dibromo-6,7-dichloro-2,3,4,9-tetrahydro-1H-carbazol-1-one (0.1 g, 0.24 mmol) was dissolved in DMF (2 mL) and LiBr (0.02 g, 0.26 mmol) followed by $Li_2CO_3$ (0.01 g, 0.25 mmol) were added. The reaction mixture was heated to 110° C. for 2 h, cooled to room temperature and quenched with saturated $NH_4Cl$ (10 mL), extracted with EtOAc (2×15 mL) and the combined organic extracts were concentrated in vacuo to give the crude compound which was purified by silica gel chromatography [EtOAc-hexane (1:9) as eluant] to provide the title compound as light red solid (30 mg, 37%). $^1$H NMR (500 MHz, $CDCl_3$, δ in ppm): 8.28 (bs, 1H), 8.07 (s, 1H), 7.57 (s, 1H), 7.46 (d, J=8.0 Hz, 1H), 7.31 (d, J=8.5 Hz, 1H), 5.72 (s, 1H).

Example 35

2-Benzyl-5,6-dichloro-9H-carbazol-1-ol

Intermediate 35a

2-Benzylidene-5,6-dichloro-2,3,4,9-tetrahydro-1H-carbazol-1-one

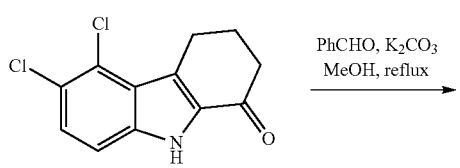

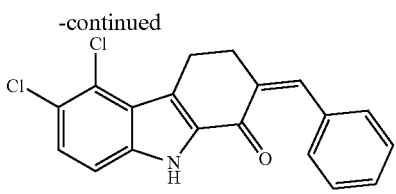

To a solution of 5,6-dichloro-2,3,4,9-tetrahydro-1H-carbazol-1-one (intermediate 5a) (0.8 g, 1.97 mmol) in MeOH (10 mL), KOH (0.055 g, 0.98 mmol) followed by PhCHO (1.0 g, 9.42 mmol) were added. The reaction mixture was heated to 80° C. for 12 h cooled to room temperature during which a solid precipitated out which was filtered and dried in vacuo to give the title compound as a light yellow solid (0.7 g, 70%). $^1$H NMR (500 MHz, CDCl$_3$, δ in ppm) 9.25 (bs, 1H), 7.80 (s, 1H), 7.45-7.42 (m, 4H), 7.39-7.35 (m, 2H), 7.31 (d, J=9.0 Hz, 1H), 3.44 (t, J=6.0 Hz, 2H), 3.28 (t, J=6.0 Hz, 2H).

Intermediate 35b

2-Benzyl-5,6-dichloro-2,3,4,9-tetrahydro-1H-carbazol-1-one

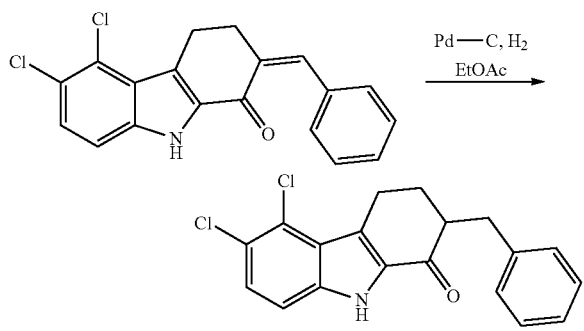

2-Benzylidene-5,6-dichloro-2,3,4,9-tetrahydro-1H-carbazol-1-one (0.7 g, 2.05 mmol) was dissolved in EtOAc (150 mL) and 10% Pd/C (0.070 g) was added under N$_2$ atmosphere. The reaction mixture was stirred under H$_2$ atmosphere at room temperature for 12 h then filtered through a Celite® pad. The Celite® pad was washed with EtOAc (2×20 mL) and the filtrate was concentrated in vacuo to provide the crude material which was purified by silica gel chromatography [EtOAc-hexane (1:9) as eluant] to obtain the title compound as a light green solid (0.43 g, 61%). $^1$H NMR (500 MHz, CDCl$_3$, δ in ppm) 9.03 (bs, 1H), 7.37 (d, J=9.0 Hz, 1H), 7.34-7.30 (m, 3H), 7.25-7.22 (m, 3H), 3.50-3.42 (m, 2H), 3.17-3.10 (m, 1H), 2.87-2.82 (m, 1H), 2.72-2.67 (m, 1H), 2.25-2.21 (m, 1H), 1.97-1.90 (m, 1H).

Intermediate 35c

2-Benzyl-2-bromo-5,6-dichloro-2,3,4,9-tetrahydro-1H-carbazol-1-one

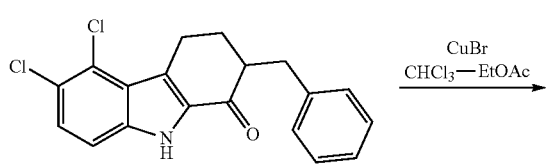

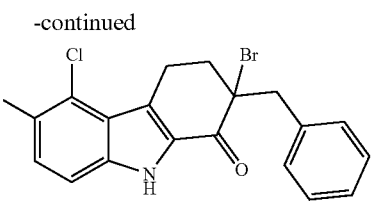

To a solution of CuBr$_2$ (0.3 g, 1.50 mmol) in EtOAc (5 mL), heated to 60° C., benzyl-5,6-dichloro-2,3,4,9-tetrahydro-1H-carbazol-1-one (0.43 g, 1.25 mmol) dissolved in CHCl$_3$ (8 mL) was added. The reaction mixture was stirred at 60° C. for 12 h, filtered through a pad of Celite® and the filtrate was concentrated under reduced pressure to give the crude material which was purified by silica gel chromatography [EtOAc-hexane (1:9) as eluant] to obtain the title compound as a yellow solid (0.48 g, 92%). $^1$H NMR (500 MHz, CDCl$_3$, δ in ppm) 9.0 (bs, 1H), 7.38 (d, J=9.0 Hz, 1H), 7.32-7.28 (m, 4H), 7.27-7.24 (m, 2H), 3.92 (d, J=14.5 Hz, 1H), 3.57 (d, J=14.0 Hz, 1H), 3.53-3.49 (m, 1H), 3.25-3.18 (m, 1H), 2.48-2.43 (m, 1H), 2.30-2.24 (m, 1H).

Example 35

2-Benzyl-5,6-dichloro-9H-carbazol-1-ol

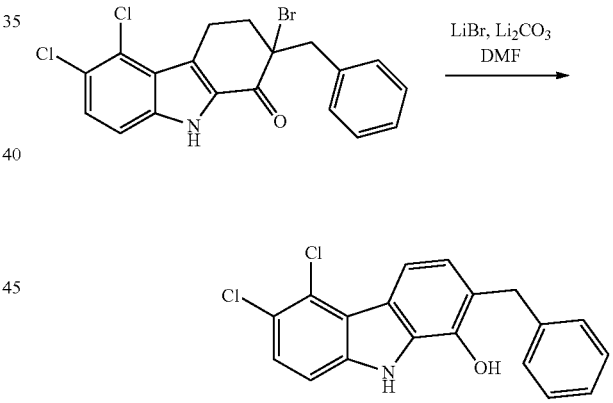

2-Benzyl-2-bromo-5,6-dichloro-2,3,4,9-tetrahydro-1H-carbazol-1-one (0.48 g, 1.14 mmol) was dissolved in DMF (4 mL) and LiBr (0.1 g, 1.25 mmol) followed by Li$_2$CO$_3$ (0.09 g, 1.25 mmol) were added. The reaction mixture was heated to 90° C. for 1 h, then cooled to room temperature, diluted with water and extracted with EtOAc (3×20 mL). The combined organic extracts were dried over Na$_2$SO$_4$ and concentrated in vacuo to give the crude compound which was purified by column chromatography [EtOAc-hexane (3:17) as eluant] to provide the title compound as a light green solid (0.215 g, 56%). $^1$H NMR (500 MHz, DMSO-d6, δ in ppm) 11.31 (s, 1H), 9.22 (s, 1H), 7.88 (d, J=8.5 Hz, 1H), 7.52 (s, 2H), 7.26-7.23 (m, 4H), 7.18-7.20 (m, 1H), 6.97 (d, J=8.0 Hz, 1H), 4.14 (s, 2H).

Example 36

2-Benzyl-6,7-dichloro-9H-carbazol-1-ol

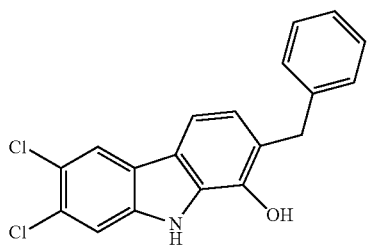 [SMILES: Oc1c(Cc2ccccc2)ccc2c1[nH]c1cc(Cl)c(Cl)cc12]

Intermediate 36a

2-Benzylidene-6,7-dichloro-2,3,4,9-tetrahydro-1H-carbazol-1-one

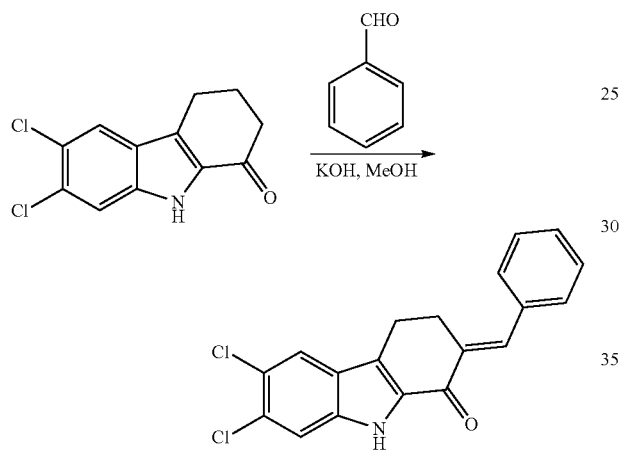

To a solution of 6,7-dichloro-2,3,4,9-tetrahydro-1H-carbazol-1-one (intermediate 1c) (0.8 g, 3.16 mmol) in MeOH (15 mL), KOH (53 mg, 0.94 mmol) followed by PhCHO (2.6 g, 24.5 mmol) were added. The reaction mixture was heated to 70-80° C. for 12 h. The solids were filtered and dried in vacuo to afford the title compound as a light yellow solid (0.75 g, 70%). $^1$H NMR (500 MHz, DMSO-d6, δ in ppm) 12.07 (s, 1H), 8.05 (s, 1H), 7.64 (d, J=13.0 Hz, 2H), 7.54 (d, J=7.0 Hz, 2H), 7.49-7.46 (m, 2H), 7.41 (d, J=7.5 Hz, 1H), 3.21-3.18 (m, 2H), 3.05-3.02 (m, 2H).

Intermediate 36b

2-Benzyl-6,7-dichloro-2,3,4,9-tetrahydro-1H-carbazol-1-one

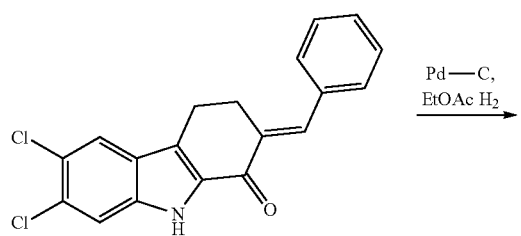

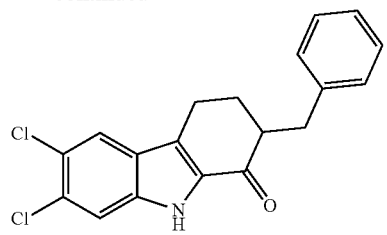

To a solution of 2-benzylidene-6,7-dichloro-2,3,4,9-tetrahydro-1H-carbazol-1-one (0.07 g, 0.20 mmol) in EtOAc (10 mL), 10% Pd/C (10 mg) was added under $N_2$ atmosphere. The reaction mixture was stirred under $H_2$ atmosphere at room temperature for 12 h. The reaction mixture was filtered through a Celite® pad. The Celite® pad was washed with EtOAc (2×20 mL) and the filtrate was concentrated in vacuo to provide the crude material which was purified by silica gel chromatography [EtOAc-hexane (1:9) as eluant] to furnish the title compound as a yellow solid (0.04 g, 57%). $^1$H NMR (500 MHz, CDCl$_3$, δ in ppm) 8.79 (s, 1H), 7.73 (s, 1H), 7.54 (s, 1H), 7.34-7.31 (m, 2H), 7.25-7.22 (m, 3H), 3.48-3.45 (m, 1H), 3.02-2.97 (m, 1H), 2.86-2.81 (m, 2H), 2.80-2.66 (m, 1H), 2.25-2.21 (m, 1H), 1.95-1.92 (m, 1H).

Intermediate 36c

2-Benzyl-2-bromo-6,7-dichloro-2,3,4,9-tetrahydro-1H-carbazol-1-one

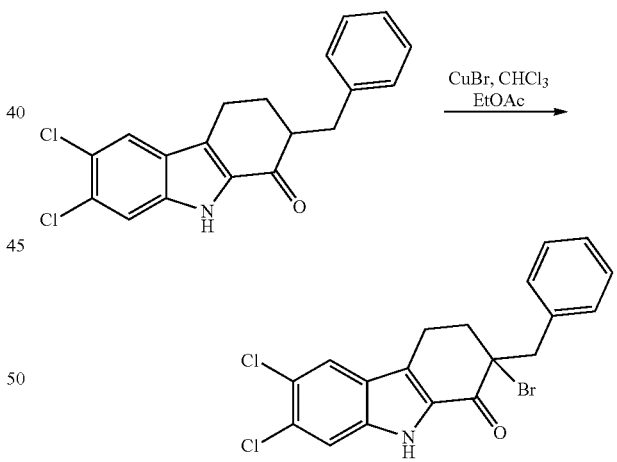

To the suspension of CuBr$_2$ (0.35 g, 1.57 mmol) in EtOAc (5 mL), heated to 60° C., 2-benzyl-6,7-dichloro-2,3,4,9-tetrahydro-1H-carbazol-1-one (0.45 g, 1.31 mmol), dissolved in CHCl$_3$ (8 mL), was added. The reaction was continued at 60° C. for 24 h, the reaction mixture was filtered through a pad of Celite®. The Celite® pad was washed with EtOAc (2×10 mL) and the combined organic extracts were dried (Na$_2$SO$_4$) and concentrated in vacuo to give the crude material which was purified by column chromatography [EtOAc-hexane (1:9) as eluant] to give the title compound as a white solid (0.3 g, 54%). $^1$H NMR (500 MHz, CDCl$_3$, δ in ppm) 8.76 (bs, 1H), 7.72 (s, 1H), 7.53 (s, 1H), 7.31-7.27 (m, 5H), 3.90 (d, J=14.0

Hz, 1H), 3.58 (d, J=14.5 Hz, 1H), 3.03-2.99 (m, 1H), 2.95-2.93 (m, 1H), 2.48-2.44 (m, 1H), 2.30-2.26 (m, 1H).

Example 36

2-Benzyl-6,7-dichloro-9H-carbazol-1-ol

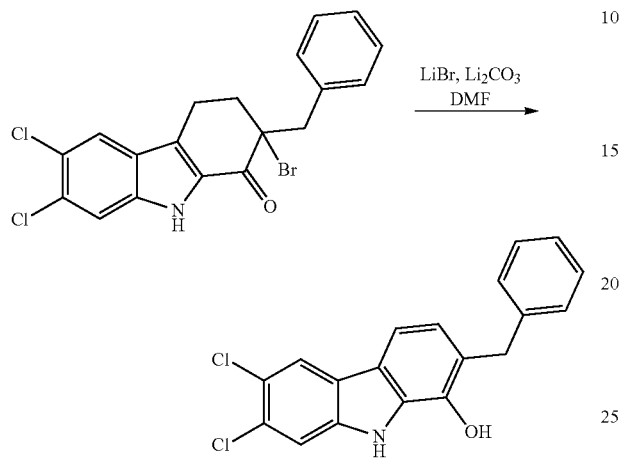

To a stirred solution of 2-benzyl-2-bromo-6,7-dichloro-2,3,4,9-tetrahydro-1H-carbazol-1-one (0.3 g, 0.71 mmol) in anhydrous DMF (5 mL), LiBr (68 mg, 0.78 mmol) followed by $Li_2CO_3$ (52 mg, 0.71 mmol) were added. The reaction mixture was heated to 90° C. for 1 h, cooled to room temperature and diluted with water. The reaction mixture was extracted with EtOAc (3×20 mL) to obtain the crude material which was purified by silica gel chromatography [EtOAc-hexane (3:17) as eluant] to give the title compound as a light brown solid (0.07 g, 30%). $^1$H NMR (500 MHz, DMSO-d6, δ in ppm) 10.98 (s, 1H), 9.18 (s, 1H), 8.29 (s, 1H), 7.74 (s, 1H), 7.59 (d, J=8.0 Hz, 1H), 7.26-7.25 (m, 4H), 7.24-7.23 (m, 1H), 6.92 (d, J=8.0 Hz, 1H), 4.11 (s, 2H).

Example 37

The binding data shown in Table 1 (below) is from the result of a single or multiple determinations based on the same compound. Where multiple data points have been taken, the value reported is the average of the multiple determinations.

TABLE 1

| Compound AR-Binding Affinity | |
|---|---|
| Compound | Binding $IC_{50}$ (nM) |
| Example 1 | >10,000 |
| Example 2 | 9200 |
| Example 3 | 15, 60 |
| Example 4 | 480 |
| Example 5 | 40, 150 |
| Example 6 | 34 |
| Example 7 | >10,000 |
| Example 8 | 34 |
| Example 9a | >1000 |
| Example 9b | 13 |
| Example 10 | 20 |
| Example 11 | 600 |
| Example 12 | 140 |
| Example 13 | 85 |

TABLE 1-continued

| Compound AR-Binding Affinity | |
|---|---|
| Compound | Binding $IC_{50}$ (nM) |
| Example 14 | 520 |
| Example 15 | 70 |
| Example 16 | 20 |
| Example 17 | 90 |
| Example 18 | >10,000 |
| Example 19 | 220 |
| Example 20 | 100 |
| Example 21 | >10,000 |
| Example 22 | 13 |
| Example 23 | 400 |
| Example 24 | 410 |
| Example 25 | 130 |
| Example 26 | >1000 |
| Example 27 | 120 |
| Example 28 | 54 |
| Example 29 | 175 |
| Example 30 | 390 |
| Example 31 | 1420 |
| Example 32 | 4600 |
| Example 33 | 15 |
| Example 34 | 34 |
| Example 35 | >1000 |
| Example 36 | >1000 |

While this invention has been particularly shown and described with references to example embodiments thereof, it will be understood by those skilled in the art that various changes in form and details may be made therein without departing from the scope of the invention encompassed by the appended claims.

What is claimed is:

1. A compound represented by Formula (I):

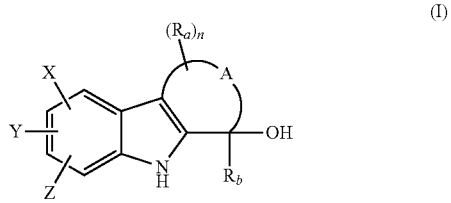

or a pharmaceutically acceptable salt thereof, wherein:

X, Y and Z are independently selected from the group consisting of hydrogen, halogen, CN, $C_{1-4}$ alkyl, $C_{1-3}$ hydroxyalkyl, and $C_{1-3}$ haloalkyl, with the proviso that at least one of X, Y and Z is not hydrogen;

each $R_a$ is independently selected from halogen, $C_{1-4}$ alkyl (wherein said $C_{1-4}$ alkyl is optionally substituted with from 1-2 substituents each independently selected from CN, OH and $OC_{1-3}$ alkyl), and $C_{1-5}$ haloalkyl;

$R_b$ is independently selected from $C_{1-4}$ alkyl (wherein said $C_{1-4}$ alkyl is optionally substituted with from 1-2 substituents each independently selected from the group consisting of CN, OH and OPh (wherein said Ph is optionally substituted with 1-2 substituents each independently selected from the group consisting of halogen, OH, CN and $OC_{1-3}$ alkyl)) and $C_{1-5}$ haloalkyl;

A is a 2-5 membered carbon alkyl linker selected from the group consisting of

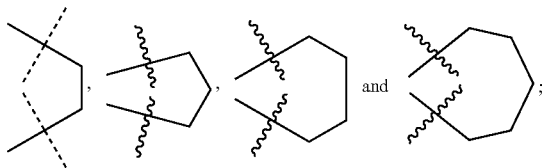

and n is 0, 1, 2 or 3.

2. A compound according to claim 1, wherein X, Y and Z are independently selected from hydrogen, chlorine, fluorine, $CF_3$ and CN; with the proviso that at least one of X, Y and Z is not hydrogen.

3. A compound according to claim 1, wherein each $R_a$ is independently selected from chlorine, fluorine, $CH_3$, $CH_3CH_2$, $CF_3$, and $CF_3CF_2$.

4. A compound according to claim 1, wherein each $R_a$ is independently selected from fluorine, $CH_3$, and $CF_3$.

5. A compound according to claim 1, wherein $R_b$ is $CH_3$, $CH_3CH_2$, $CF_3$, or $CF_3CF_2$.

6. A compound according to claim 1, wherein A is selected from the group of $C_2$-$C_4$ alkyl linkers consisting of:

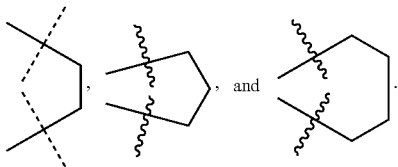

7. A compound according to claim 1, wherein n is 0, 1 or 2.

8. A compound according to claim 1, wherein:
X and Y are hydrogen;
Z is CN;
each $R_a$ is independently selected from fluorine, $CH_3$ and $CF_3$;
$R_b$ is $CH_3$, $CF_3$, or $CF_3CF_2$;
A is selected from the group of $C_2$-$C_4$ alkyl linkers consisting of:

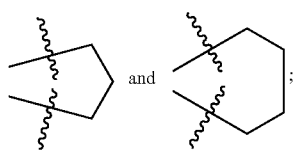 [SMILES: *CCC* ; *CCCC*]

and
n is 0, 1 or 2.

9. A compound according to claim 1, wherein:
X is hydrogen;
Y is $CF_3$;
Z is CN;
each $R_a$ is independently selected from fluorine, $CH_3$ and $CF_3$;
$R_b$ is $CH_3$, $CF_3$, or $CF_3CF_2$;

A is selected from the group of $C_2$-$C_4$ alkyl linkers consisting of:

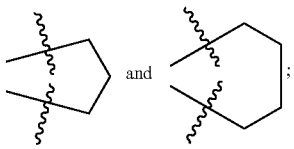 [SMILES: *CCC* ; *CCCC*]

and
n is 0, 1 or 2.

10. A compound according to claim 1, wherein:
X is hydrogen;
Y and Z are chlorine;
each $R_a$ is independently selected from fluorine, $CH_3$ and $CF_3$;
$R_b$ is $CH_3$, $CF_3$, or $CF_3CF_2$;
A is selected from the group of $C_2$-$C_4$ alkyl linkers consisting of:

and
n is 0, 1 or 2.

11. A compound according to claim 1, wherein:
X is hydrogen;
Y is chlorine;
Z is fluorine;
each $R_a$ is independently selected from fluorine, $CH_3$ and $CF_3$;
$R_b$ is $CH_3$, $CF_3$, or $CF_3CF_2$;
A is selected from the group of $C_2$-$C_4$ alkyl linkers consisting of:

and
n is 0, 1 or 2.

12. A compound according to claim 1, wherein:
X, Y and Z are chlorine;
each $R_a$ is independently selected from fluorine, $CH_3$ and $CF_3$;
$R_b$ is $CH_3$, $CF_3$, or $CF_3CF_2$;
A is selected from the group of $C_2$-$C_4$ alkyl linkers consisting of:

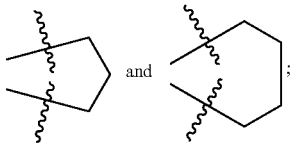 [SMILES: *CCC* ; *CCCC*]

and
n is 0, 1 or 2.

13. A compound according to claim 1, represented by Formula (Ia), (Ib) or (Ic):

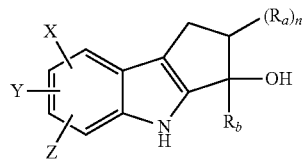
(Ia)

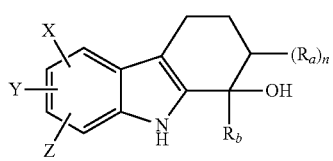
(Ib)

or

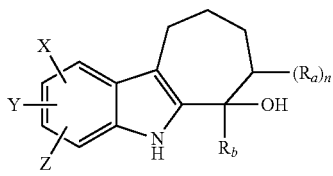
(Ic)

or a pharmaceutically acceptable salt of any of the foregoing, wherein:
X, Y, Z, $R_a$, and $R_b$ are as defined in claim 1; and
n is 0, 1 or 2.

14. A compound selected from the group consisting of:
6,7-Dichloro-1-methyl-2,3,4,9-tetrahydro-1H-carbazol-1-ol, 1-Hydroxy-1-methyl-2,3,4,9-tetrahydro-1H-carbazole-6-carbonitrile, 6,7-Dichloro-1-(trifluoromethyl)-2,3,4,9-tetrahydro-1H-carbazol-1-ol, 1-Hydroxy-1-(trifluoromethyl)-2,3,4,9-tetrahydro-1H-carbazole-6-carbonitrile, 5,6-Dichloro-1(trifluoromethyl)-2,3,4,9-tetrahydro-1H-carbazol-1ol, 6,7-Dichloro-1-(perfluoroethyl)-2,3,4,9-tetrahydro-1H-carbazol-1-ol, 1-Hydroxy-1-(perfluoroethyl)-2,3,4,9-tetrahydro-1H-carbazole-6-carbonitrile, 6,8-Dichloro-1-(trifluoromethyl)-2,3,4,9-tetrahydro-1H-carbazol-1-ol, (S)-6,7-Dichloro-1-(trifluoromethyl)-2,3,4,9-tetrahydro-1H-carbazol-1-ol, (R)-6,7-dichloro-1-(trifluoromethyl)-2,3,4,9-tetrahydro-1H-carbazol-1-ol, (R)-6,8-Dichloro-1 - (trifluoromethyl)-2,3,4,9-tetrahydro-1H-carbazol-1-ol, 2,4-Dichloro-6-(trifluoromethyl)-5,6,7,8,9,10-hexahydrocyclohept[b]indol-6-ol, 6,7-Dichloro-2-fluoro-1-(trifluoromethyl)-2,3,4,9-tetrahydro-1H-carbazol-1-ol, 5,8-Dichloro-1-(trifluoromethyl)-2,3,4,9-tetrahydro-1H-carbazol-1-ol, 5-Chloro-6-fluoro-1-(trifluoromethyl)-2,3,4,9-tetrahydro-1H-carbazol-1-ol, 5,6-Dichloro-2-fluoro-1-(trifluoromethyl)-2,3,4,9-tetrahydro-1H-carbazol-1-ol, 7-Chloro-6-fluoro-1-(trifluoromethyl)-2,3,4,9-tetrahydro-1H-carbazol-1-ol, 8-Chloro-6-fluoro-1-(trifluoromethyl)-2,3,4,9-tetrahydro-1H-carbazol-1-ol, 8-Chloro-6-fluoro-1,2-bis(trifluoromethyl)-2,3,4,9-tetrahydro-1H-carbazol-1-ol, 6,7-Dichloro-2,2-difluoro-1-(trifluoromethyl)-2,3,4,9-tetrahydro-1H-carbazol-1-ol, 6,8-Dichloro-2,2-difluoro-1-(trifluoromethyl)-2,3,4,9-tetrahydro-1H-carbazol-1-ol, 5,6,8-Trichloro-1-(trifluoromethyl)-2,3,4,9-tetrahydro-1H-carbazol-1-ol, 5,7-Dichloro-3-(trifluoromethyl)-1,2,3,4-tetrahydrocyclopenta[b]indol-3-ol, 5,6-Dichloro-2-methyl-1-(trifluoromethyl)-2,3,4,9-tetrahydro-1H-carbazol-1-ol, 5,6,7-Trichloro-1-(trifluoromethyl)-2,3,4,9-tetrahydro-1H-carbazol-1-ol, 7,8-Dichloro-1-(trifluoromethyl)-2,3,4,9-tetrahydro-1H-carbazol-1-ol, 6,7-Dichloro-2-methyl-1-(trifluoromethyl)-2,3,4,9-tetrahydro-1H-carbazol-1-ol, 6,7-Dichloro-3-(trifluoromethyl)-1,2,3,4-tetrahydrocyclopenta[b]indol-3-ol, 6-Chloro-8-fluoro-1-(trifluoromethyl)-2,3,4,9-tetrahydro-1H-carbazol-1-ol, 7,8-Dichloro-3-(trifluoromethyl)-1,2,3,4-tetrahydrocyclopenta[b]indol-3-ol, and 1-Hydroxy-1,8-bis(trifluoromethyl)-2,3,4,9-tetrahydro-1H-carbazole-6-carbonitrile,
or a pharmaceutically acceptable salt of any of the foregoing.

15. A pharmaceutical composition comprising a compound according to claim 1, or a pharmaceutically acceptable salt thereof, and at least one pharmaceutically acceptable excipient.

16. A compound represented by the following structural formula:

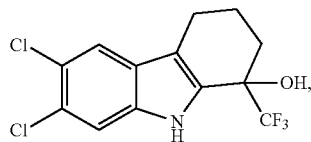 [SMILES: OC1(C(F)(F)F)CCCc2c1[nH]c1cc(Cl)c(Cl)cc21]

or a pharmaceutically acceptable salt thereof.

17. A compound according to claim 1, wherein X, Y and Z are independently selected from the group consisting of hydrogen, halogen, $C_{1-3}$ haloalkyl and CN; with the proviso that at least one of X, Y and Z is not hydrogen.

* * * * *